United States Patent [19]
Lohray et al.

[11] Patent Number: 5,889,032
[45] Date of Patent: Mar. 30, 1999

[54] HETEROCYCLIC COMPOUNDS HAVING ANTIDIABETIC, HYPOLIPIDAEMIC, ANTIHYPERTENSIVE PROPERTIES, PROCESS FOR THEIR PREPARATION AND PHARMACEUTICAL COMPOSITIONS CONTAINING THEM

[75] Inventors: Vidya Bhushan Lohray; Braj Bhushan Lohray; Ashok Channaveerappa Bajji; Sekar Reddy Alla; Rajagopalan Ramanujam; Ranjan Chakrabarti, all of Hyderabad, India

[73] Assignees: Dr. Reddy's Research Foundation, Hyderabad, India; Reddy-Cheminor, Inc., Ridgewood, N.J.

[21] Appl. No.: 851,448

[22] Filed: May 5, 1997

[30] Foreign Application Priority Data

May 6, 1996 [IN] India ............... 821/MAS/96

[51] Int. Cl.$^6$ ............ A61K 31/425; A61K 31/395; C07D 277/34; C07D 417/02
[52] U.S. Cl. ............ 514/369; 514/255; 514/320; 514/342; 514/343; 514/364; 514/376; 514/414; 514/422; 544/369; 544/373; 544/376; 546/196; 546/269.7; 546/276.4; 548/144; 548/183; 548/227; 548/468; 548/525
[58] Field of Search .................. 514/255, 320, 514/342, 343, 364, 369, 376, 414, 422; 544/369, 373, 376; 546/196, 269.7, 276.4; 548/144, 183, 227, 468, 525

[56] References Cited

U.S. PATENT DOCUMENTS

| | | | |
|---|---|---|---|
| 4,342,771 | 8/1982 | Schnur | 424/263 |
| 4,367,234 | 1/1983 | Schnur | 424/272 |
| 4,725,610 | 2/1988 | Meguro | 514/369 |
| 4,873,255 | 10/1989 | Yoshioka | 514/369 |
| 5,002,953 | 3/1991 | Hindley | 513/275 |
| 5,036,079 | 7/1991 | Clark | 514/333 |
| 5,037,842 | 8/1991 | Goldstein | 514/375 |
| 5,130,379 | 7/1992 | Clark | 514/333 |
| 5,153,210 | 10/1992 | Ainsworth | 514/369 |
| 5,296,605 | 3/1994 | De Nanteuil | 546/176 |
| 5,330,999 | 7/1994 | De Nanteuil | 514/369 |
| 5,420,146 | 5/1995 | Malamas | 514/364 |
| 5,468,762 | 11/1995 | Malamas | 514/376 |
| 5,478,851 | 12/1995 | Cantello | 514/369 |
| 5,478,852 | 12/1995 | Olefsky | 514/369 |
| 5,478,853 | 12/1995 | Regnier | 514/369 |
| 5,480,896 | 1/1996 | Malamas | 514/364 |
| 5,498,621 | 3/1996 | Dow | 514/369 |
| 5,521,201 | 5/1996 | Hindley | 514/369 |
| 5,521,202 | 5/1996 | Yano | 514/369 |

FOREIGN PATENT DOCUMENTS

| | | |
|---|---|---|
| 570067 | 3/1985 | Australia . |
| 008203A | 2/1980 | European Pat. Off. . |
| 0139421 | 5/1985 | European Pat. Off. . |
| 155845A | 9/1985 | European Pat. Off. . |
| 0207581 | 1/1987 | European Pat. Off. ...... C07D 417/12 |
| 236624 | 9/1987 | European Pat. Off. . |
| 0306228 | 3/1989 | European Pat. Off. . |
| 0332331 | 9/1989 | European Pat. Off. . |
| 0332332 | 9/1989 | European Pat. Off. . |
| 0337819 | 10/1989 | European Pat. Off. . |
| 0356214 | 2/1990 | European Pat. Off. . |
| 0397453 | 11/1990 | European Pat. Off. . |
| 0415605 | 3/1991 | European Pat. Off. . |
| 0419035 | 3/1991 | European Pat. Off. . |
| 0428312 | 5/1991 | European Pat. Off. . |
| 0439321 | 7/1991 | European Pat. Off. . |
| 0441605 | 8/1991 | European Pat. Off. . |
| 0454501 | 10/1991 | European Pat. Off. . |
| 0528734 | 2/1993 | European Pat. Off. . |
| 0543662 | 5/1993 | European Pat. Off. . |
| 0236624 | 8/1993 | European Pat. Off. ...... C07D 417/38 |
| 590793A | 4/1994 | European Pat. Off. . |
| 0604983 | 7/1994 | European Pat. Off. . |

(List continued on next page.)

OTHER PUBLICATIONS

English Translation of JP-A-0912575, 1997.

Khan, A., et al., "Synthesis and Antibacterial Activity of Some New 2-aryloxymethyl-3-substituted-quinazollin-4 (3H)-ones" Pharmazie vol. 43, No. 12, pp. 864–865, 1998.

Chemical Abstracts, vol. 93, No. 17, Oct. 27, 1980, No. 168217.

Shukla, J.S., et al. "Synthesis of 2-phenoxymethyl-3-(2'-pyridyl/thiazolyl)-4-quinazolones as Possible Antifertility Drugs" Indian Journal Chemical, vol. 17B, No. 6, pp. 651–652, Jun. 1979.

Husain, M.I., et al., "Some New 2-aryloxymethyl-3-.alpha.-substituted carboxymethyl-6,8 substituted 4-quinazolones as Possible Anticonvulsants", Pharmazie, vol. 37, No. 6, 1982, pp. 408–410.

(List continued on next page.)

Primary Examiner—Mukund J. Shah
Assistant Examiner—Brenda Coleman
Attorney, Agent, or Firm—Ladas & Parry

[57] ABSTRACT

The present invention relates to novel antidiabetic compounds, their tautomeric forms, their derivatives, their stereoisomers, their polymorphs, their pharmaceutically acceptable salts, their pharmaceutically acceptable solvates and pharmaceutically acceptable compositions containing them. This invention particularly relates to novel azolidinedione derivatives of the general formula (I), and their pharmaceutically acceptable salts, pharmaceutically acceptable solvates and pharmaceutical compositions containing them.

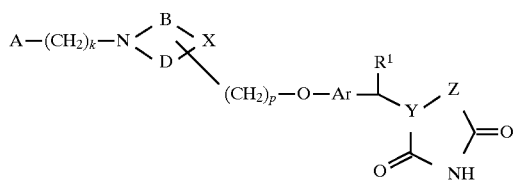

19 Claims, No Drawings

FOREIGN PATENT DOCUMENTS

| | | |
|---|---|---|
| 605228A | 7/1994 | European Pat. Off. . |
| 0612743 | 8/1994 | European Pat. Off. . |
| 0643050 | 3/1995 | European Pat. Off. . |
| 645387A | 3/1995 | European Pat. Off. . |
| 0676398 | 10/1995 | European Pat. Off. . |
| 0678511 | 10/1995 | European Pat. Off. . |
| 0708098 | 4/1996 | European Pat. Off. . |
| 0733631 | 9/1996 | European Pat. Off. . |
| 745600A | 12/1996 | European Pat. Off. . |
| 0783888 | 7/1997 | European Pat. Off. . |
| 0787727 | 8/1997 | European Pat. Off. . |
| 62-175458 | 8/1987 | Japan . |
| 64-52765 | 2/1989 | Japan . |
| 7138258 | 5/1995 | Japan . |
| 2558473 | 11/1996 | Japan . |
| 0912575 | 1/1997 | Japan . |
| 5355524 | 8/1984 | Spain . |
| 9112003 | 8/1991 | WIPO . |
| 9207838 | 5/1992 | WIPO . |
| 9207850 | 5/1992 | WIPO . |
| 9405659 | 3/1994 | WIPO . |
| 9425026 | 11/1994 | WIPO . |
| 9507697 | 3/1995 | WIPO . |
| 9521608 | 8/1995 | WIPO . |
| 9526347 | 10/1995 | WIPO . |
| 9535108 | 12/1995 | WIPO . |
| 9605186 | 2/1996 | WIPO . |
| 9611196 | 4/1996 | WIPO . |
| 9626207 | 8/1996 | WIPO . |

OTHER PUBLICATIONS

G. De Nanteuil, "Euglygaemic and Biological Activities of Novel Thiazolidine–2,4–dione Derivatives" Arzneittel Forschung/Drug Design, vol. 45, No. II, 1995, pp. 1176–1181.

Whitcomb, R.W., "Thiazolidinediones", Expert Opinion on Investigational Drugs, vol.4, No. 12, Dec. 1995, pp. 1299–1309.

Modan, Michaela, et al. "Hyperinsulinemia A Link Between Hypertension Obesity and Glucose Intolerance." The American Society for Clinical Investigation, vol. 75 (Mar. 1985), pp. 809–817.

Kolterman, O. G., et al. "Receptor and Postreceptor Defects Contibute to the Insulin Resistance in Noninsulin–dependent Diabetes Mellitus." The American Society for Clinical Investigation, vol. 68 (Oct. 1981), pp. 957–969.

Ferrannini, E., et al. "Insulin Resistance in Essential Hypertension." The New England Journal of Medicine, vol. 317, No. 6 (Aug. 1987), pp. 350–357.

Shen, D. C., et al. "Resistance to Insulin–Stimulated–Glucose Uptake in Patients with Hypertension." Journal of Clinical Endocrinology and Metabolism, vol. 66, No. 3 (1988), pp. 580–583.

Cantello, Barrie C. C., et al. "(Heterocyclylamino) alkoxy] benzyl]–2,4–thiazolidinediones and Potent Antihyperglycemic Agents." Journal of Medicinal Chemistry, vol. 37, No. 23 (1994), pp. 3977–3985.

Antonucci, T., et al. "Impaired Glucose Tolerance is Normalized by Treatment with the Thiazolidinedione Troglitazone." Diabetes Care, vol. 20, No. 2 (Feb. 1997), pp. 188–193.

Bailey, C. J. "Potential new treatments for type 2 diabetes." Chemistry and Industry, (Jan. 1998), pp. 53–57.

"Hormones and Hormone Antagonists" Goodman & Gilman's The Pharmacological Baisis of Therapeutics, Ninth Edition, Section XIII. pp. 1496–1497, 1996.

Hulin, B., et al. "Hypoglycemic Activity of a Series of a–Alkylthio and a–Alkoxy Carboxylic Acids Related to Ciglitazone." Journal of Medicinal Chemistry, vol. 39, No. 20 (1996), pp. 3897–3907.

Behavioral Brain Research, 75 (1996) pp. 1–11, Messier, et al.

Chemical Pharmaceutical Bulletin, vol. 30, No. 10, 1982 pp. 3580–3600, Taskasi Sohda, et al.

D.A. Clark et al., "Substituted Dihydrobenzeopran . . . ", J. Med. Chem. 1991, 34, 319–325.

R.L. Dow et al., "Benzyloxzolidine–2,4–diones . . . ", J. Med. Chem. 1991, 34, 1538–1544.

S.W. Goldstein et al., "Hydroxyurea Derivatives . . . ", J. Med. Chem. 1993, 36, 2238–2240.

B. Hulin et al., "Novel Thiazolidine . . . ", J. Med. Chem. 1992, vol. 35, No. 10, 1853–1864.

Journal of Medicinal Chemistry, vol. 37, No. 23, 1994, Barrie, CC. Et al., pp. 3977–3985.

T. Sohda et al., "Studies on Antidiabetic . . . ", J. Med. Chem., 1992, vol. 35, No. 14, 2617–2626.

HETEROCYCLIC COMPOUNDS HAVING ANTIDIABETIC, HYPOLIPIDAEMIC, ANTIHYPERTENSIVE PROPERTIES, PROCESS FOR THEIR PREPARATION AND PHARMACEUTICAL COMPOSITIONS CONTAINING THEM

FIELD OF THE INVENTION

The present invention relates to novel antidiabetic compounds, their tautomeric forms, their derivatives, their stereoisomers, their polymorphs, their pharmaceutically acceptable salts, their pharmaceutically acceptable solvates and pharmaceutically acceptable compositions containing them. This invention particularly relates to novel azolidinedione derivatives of the general formula (I), their tautomeric forms, their stereoisomers, their polymorphs and their pharmaceutically acceptable salts, pharmaceutically acceptable solvates and pharmaceutical compositions containing them.

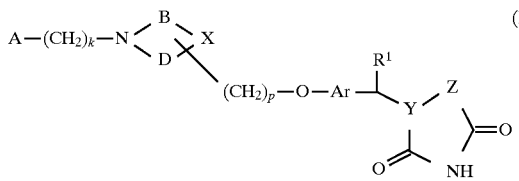

The present invention also relates to a process for the preparation of the above said novel, azolidinedione derivatives, their tautomeric forms, their stereoisomers, their polymorphs, their pharmaceutically acceptable salts, pharma-ceutically acceptable solvates, novel intermediates and pharmaceutical compositions containing them.

The azolidinedione derivatives of the general formula (I) defined above of the present invention are useful for the treatment and/or prophylaxis of diseases or conditions in which insulin resistance is the underlying pathophysiological mechanism. Examples of these diseases and conditions are type II diabetes, impaired glucose tolerance, dyslipidaemia, hypertension, coronary heart disease and other cardiovascular disorders including atherosclerosis. The azolidinedione derivatives of the formula (I) are useful for the treatment of insulin resistance associated with obesity and psoriasis. The azolidinedione derivatives of the formula (I) can also be used to treat diabetic complications and can be used for treatment and/or prophylaxis of other diseases and conditions such as polycystic ovarian syndrome (PCOS), certain renal diseases including diabetic nephropathy, glomerulonephritis, glomerular sclerosis, nephrotic syndrome, hypertensive nephrosclerosis, end-stage renal diseases and microalbuminuria as well as certain eating disorders, as aldose reductase inhibitors and for improving cognitive functions in dementia.

BACKGROUND OF THE INVENTION

Insulin resistance is the diminished ability of insulin to exert its biological action across a broad range of concentrations. In insulin resistance, the body secretes abnormally high amounts of insulin to compensate for this defect; failing which, the plasma glucose concentration inevitably rises and develops into diabetes. Among the developed countries, diabetes mellitus is a common problem and is associated with a variety of abnormalities including obesity, hypertension, hyperlipidemia (J. Clin. Invest., (1985) 75:809–817; N. Engl. J. Med. (1987) 317: 350–357; J. Clin. Endocrinol. Metab., (1988) 66:580–583; J. Clin. Invest., (1975) 68:957–969) and other renal complications (See Patent Application No. WO 95/21608). It is now increasingly being recognized that insulin resistance and relative hyperinsulinemia have a contributory role in obesity, hypertension, atherosclerosis and type 2 diabetes mellitus. The association of insulin resistance with obesity, hypertension and angina has been described as a syndrome having insulin resistance as the central pathogenic link-Syndrome-X. In addition, polycystic ovarian syndrome (Patent Application No. WO 95/07697), psoriasis (Patent Application No. WO 95/35108), dementia (Behavioral Brain Research (1996) 75:1–11) etc. may also have insulin resistance as a central pathogenic feature.

A number of molecular defects have been associated with insulin resistance. These include reduced expression of insulin receptors on the plasma membrane of insulin responsive cells and alterations in the signal transduction pathways that become activated after insulin binds to its receptor including glucose transport and glycogen synthesis.

Since defective insulin action is thought to be more important than failure of insulin secretion in the development of non-insulin dependent diabetes mellitus and other related complications, this raises doubts about the intrinsic suitability of antidiabetic treatment that is based entirely upon stimulation of insulin release. Recently, Takeda has developed a new class of compounds which are the derivatives of 5-(4-alkoxybenzyl)-2,4-thiazolidinediones of the formula (II) (Ref. Chem. Pharm. Bull. 1982, 30, 3580–3600). In the formula (II), V represents substituted or unsubstituted divalent aromatic group and U represents various groups which have been reported in various patent documents.

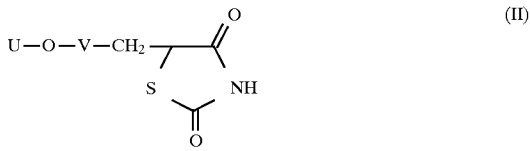

By way of examples, U may represent the following groups:

(i) a group of the formula (IIa) where $R^1$ is hydrogen or hydrocarbon residue or heterocyclic residue which may each be substituted, $R^2$ is hydrogen or a lower alkyl which may be substituted by hydroxy group, X is an oxygen or sulphur atom, Z is a hydroxylated methylene or a carbonyl, m is 0 or 1, n is an integer of 1–3.

These compounds have been disclosed in the European Patent Application No. 0 177 353

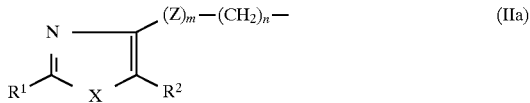

An example of these compounds is shown in formula (IIb)

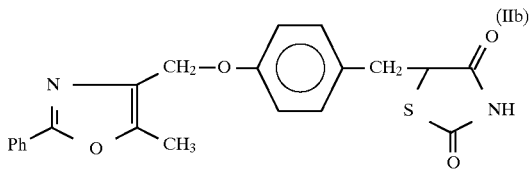

(ii) a group of the formula (IIc) wherein $R^1$ and $R^2$ are the same or different and each represents hydrogen or $C_1$-$C_5$ alkyl, $R^3$ represents hydrogen, acyl group, a ($C_1$–$C_6$) alkoxycarbonyl group or aralkyloxycarbonyl group, $R^4$–$R^5$ are same or different and each represent hydrogen, $C_1$–$C_5$ alkyl or $C_1$–$C_5$ alkoxy or $R^4$, $R^5$ together represent $C_1$–$C_4$ alkenedioxy group, n is 1, 2, or 3, W represents $CH_2$, CO, $CHOR^6$ group in which $R^6$ represents any one of the items or groups defined for $R^3$ and may be the same or different from $R^3$. These compounds are disclosed in the European Patent Application No. 0 139 421.

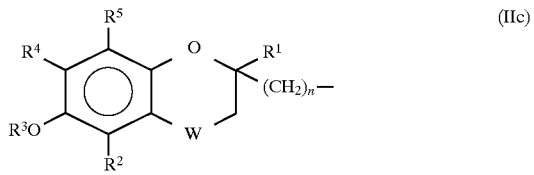

(IIc)

An example of these compounds is shown in (IId)

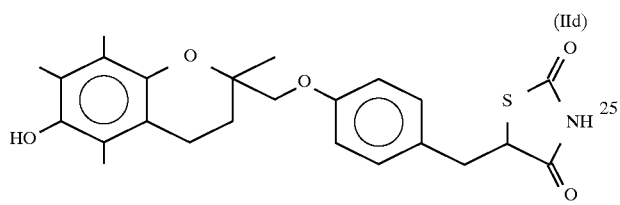

(IId)

iii) A group of formula (IIe) where $A^1$ represents substituted or unsubstituted aromatic heterocyclic group, $R^1$ represents a hydrogen atom, alkyl group, acyl group, an aralkyl group wherein the aryl moiety may be substituted or unsubstituted, or a substituted or unsubstituted aryl group, n represents an integer in the range from 2 to 6. These compounds are disclosed in European Patent No. 0 306 228.

(IIe)

An example of this compound is shown in formula (IIf)

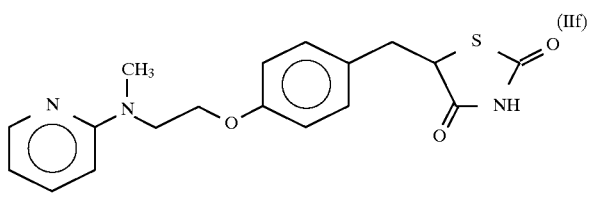

(IIf)

iv) A group of formula (IIg) where Y represents N or $CR^5$, $R^1$, $R^2$, $R^3$, $R^4$ and $R^5$ represents hydrogen, halogen, alkyl and the like and $R^6$ represents hydrogen, alkyl, aryl and the like, n represents an integer of 0 to 3. These compounds are disclosed in European Patent Application No. 0 604 983.

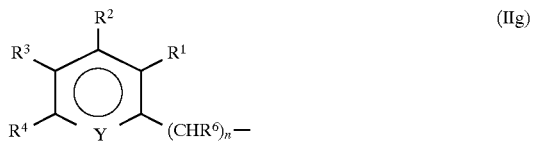

(IIg)

An example of this compound is shown in formula (IIh)

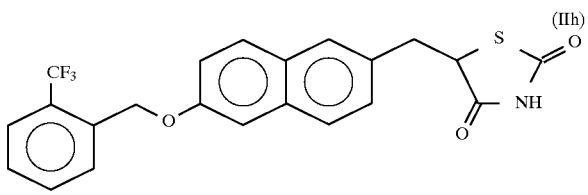

(IIh)

v) A group of formula (IIi a–d) where $R^1$ represents hydrogen atom, halogen, linear or branched ($C_1$–$C_6$) alkyl, ($C_1$–$C_6$)alkoxy, trifluoromethyl or cyano groups and X represents S, O or NR where R=H or ($C_1$–$C_6$) alkyl group. These compounds are disclosed in European Patent Application No. 0 528 734.

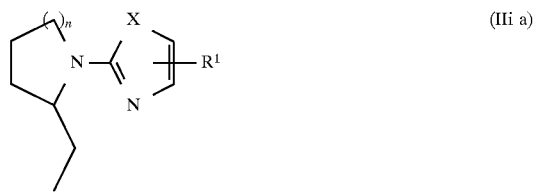

(IIi a)

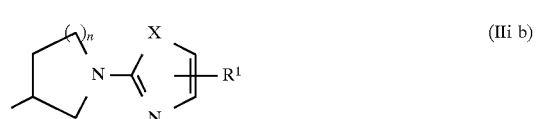

(IIi b)

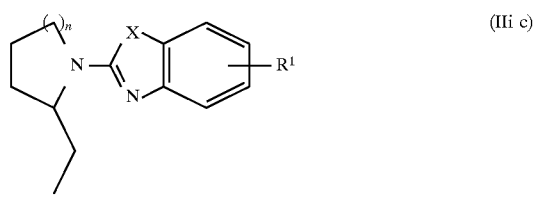

(IIi c)

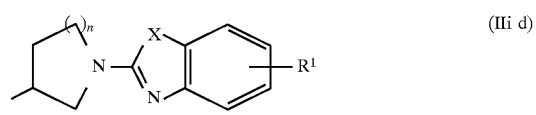

(IIi d)

An example of this class of compound is shown in formula (IIj)

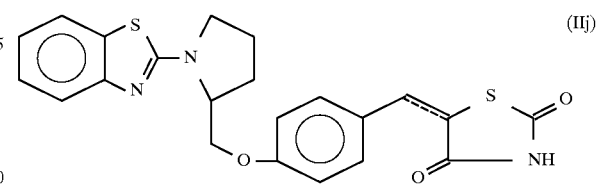

(IIj)

Still another class of antihyperglycemic agents are 5-substituted oxazolidine-2,4-diones and 2-substituted-1,2,4-oxadiazolidine-3,5-diones which can be represented in the formula (IIk),

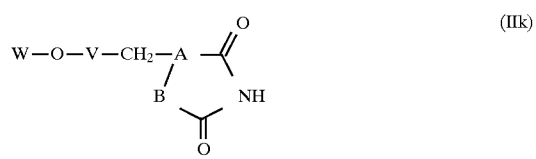

(IIk)

where V represents substituted or unsubstituted divalent aryl or hetero aryl group, W represents various groups which have been reported in various patent documents, A represents nitrogen atom or a CH group and B is an oxygen atom.

By way of examples, W may represent the following groups:

vi) a group of formula (II 1), where R is $(C_1-C_6)$ alkyl groups, cycloalkyl group, furyl, thienyl, substituted or unsubstituted phenyl group, X is hydrogen, methyl, methoxy, chloro or fluoro.

These compounds have been disclosed in the U.S. Pat. No. 5 037 842.

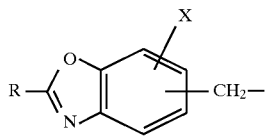

An example of these compounds is shown in formula (IIm).

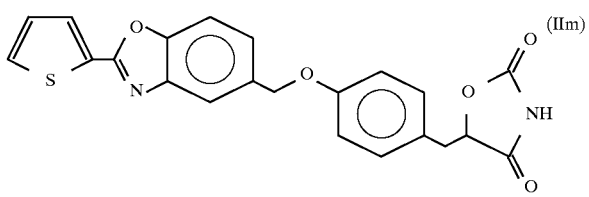

(vii) A group of formula (IIn) wherein $A^1$ represents a substituted or unsubstituted aromatic heterocyclyl group; $R^1$ represents a hydrogen atom, an alkyl group, an acyl group, an aralkyl group, wherein the aryl moiety may be substituted or unsubstituted or a substituted or unsubstituted aryl group, n represents an integer in the range of from 2 to 6. These compounds have been disclosed in the patent application No. WO 92/02520.

An example of these compounds is shown in formula (IIo).

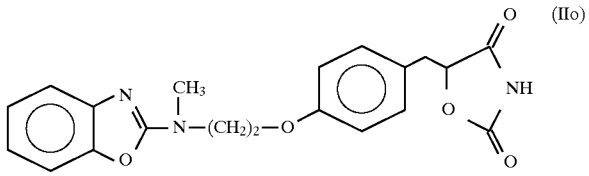

(viii) A group of formulae (IIp) and (IIq), where $R^1$ is hydrogen, $(C_1-C_8)$alkyl, $(C_1-C_8)$alkoxy, trifluoroalkoxy, halogen or trifluoromethyl group, $R^2$ is hydrogen or methyl and X is oxygen or sulfur. These compounds have been described in U.S. Pat. No. 5 480 486.

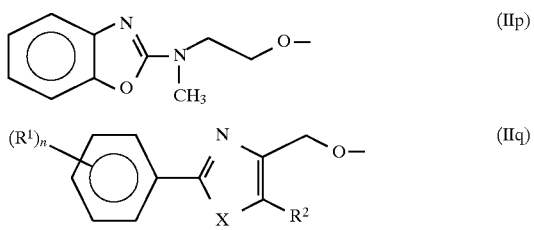

An example of these compounds is shown in formula (IIr)

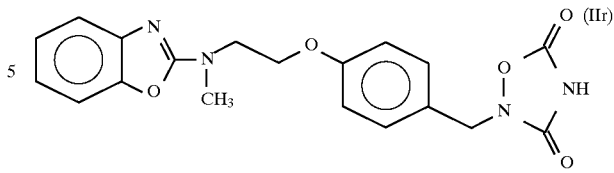

SUMMARY OF THE INVENTION

With an objective of developing new compounds for the treatment of type II diabetes [non-insulin-dependent-diabetes mellitus (NIDDM)] which could be more potent at relatively lower doses and having better efficacy with lower toxicity, we focused our research efforts in a direction of incorporating safety and to have better efficacy, which has resulted in the development of novel azolidinedione derivatives having the general formula (I) as defined above.

The main objective of the present invention is therefore, to provide novel azolidinedione derivatives, their tautomeric forms, their stereoisomers, their polymorphs, their pharmaceutically, acceptable salts, their pharmaceutically acceptable solvates and pharmaceutical compositions containing them, or their mixtures.

Another objective of the present invention is to provide novel azolidinedione derivatives, their tautomeric forms, their stereoisomers, their polymorphs, their pharmaceutically acceptable salts, their pharmaceutically acceptable solvates and pharmaceutical compositions containing them or their mixtures having enhanced activities, no toxic effect or reduced toxic effect.

Yet another objective of the present invention is to produce a process for the preparation of novel azolidinediones of the formula (I) as defined above, their tautomeric forms, their stereoisomers, their polymorphs, their pharmaceutically acceptable salts and their pharmaceutically acceptable solvates.

Still another objective of the present invention is to provide pharmaceutical compositions containing compounds of the general formula (I), their tautomers, their stereoisomers, their polymorphs, their salts, solvates or their mixtures in combination with suitable carriers, solvents, diluents and other media normally employed in preparing such compositions.

Yet another objective of the present invention is to provide a process for the preparation of the novel intermediate of the formula (III)

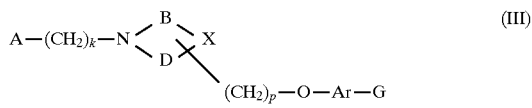

where G represents —CHO, —NO$_2$, —NH$_2$, —CH=NHOH, —CH$_2$NHOH, —CH$_2$N(OH)CONH$_2$ or —CH$_2$CH(J)—COOR, where J represents hydroxy group, or halogen atom such as chlorine, bromine or iodine and R represents H or lower alkyl group such as methyl, ethyl or propyl. A, B, D, X, k, p and Ar are as defined in formula (I).

DETAILED DESCRIPTION OF THE INVENTION

Azolidinedione derivatives of the present invention have the general formula (I)

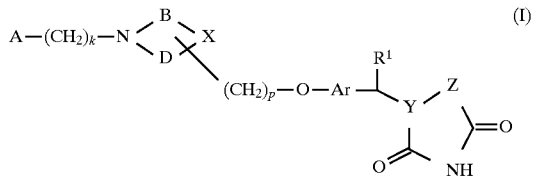

In the above formula (I), A represents substituted or unsubstituted, single or fused, aromatic group or substituted or unsubstituted, single or fused, heterocyclic group with one or more hetero atoms selected from the group of nitrogen, oxygen and sulfur; B and D represent substituted or unsubstituted linking group between N and X which may be saturated or may contain one or more double bonds; X represents either a $CH_2$ group or a hetero atom selected from the group of nitrogen, sulfur or oxygen; Ar represents an optionally substituted divalent single or fused aromatic or heterocyclic group; $R^1$ represents hydrogen atom, hydroxy, alkoxy, halogen or lower alkyl group or forms a bond together with the adjacent group Y. Y represents a nitrogen atom or a group $CR^2$ where $R^2$ represents hydrogen, hydroxy, alkoxy, halogen or lower alkyl group such as methyl, ethyl, propyl and the like or $R^2$ forms a bond together with $R^1$; Z represents an oxygen atom or a sulfur atom when Y is $CR^2$ and Z represents an oxygen atom when Y is a nitrogen atom; k is an integer ranging from 1–4 and p is an integer ranging from 0 to 4. When p is 0 (zero) $(CH_2)_p$ represents a bond.

Suitable aromatic groups represented by A include phenyl, naphthyl, phenanthryl, indenyl, fluorenyl, preferably, phenyl and naphthyl groups. Suitable heterocyclic groups, represented by A include furyl, thienyl, pyrrolyl, oxazolyl, thiazolyl, isoxazolyl, isothiazolyl, pyrazolyl, imidazolyl, pyridyl, pyridonyl, pyrimidyl, pyrimidonyl, pyridazyl, pyrazinyl, dihydrobenzofuranyl, benzofuranyl, benzothienyl, benzopyranyl, indolyl, benzoxazolyl, benzothiazolyl, benzopyrazolyl, purinyl, pthalazinyl, pthalazinonyl, quinoxalinyl, quinoxalonyl, quinazolinyl, quinazolinonyl, azaindolyl, pyridinoimidazolyl, naphthyridinyl, benzimidazolyl, quinolyl, quinalonyl, carbazolyl, phenazinyl, phenoxazinyl, phenothiazinyl, benzoxazinyl, benzoxazinonyl and the like.

Preferred heterocyclic groups represented by A include benzofuranyl, benzopyranyl, indolyl, pyridyl, dihydrobenzofuranyl, pyrimidonyl, quinazolinonyl, and benzoxazinonyl groups.

More preferred heterocyclic groups represented by A include benzofuranyl, benzopyranyl, indolyl, pyridyl, and dihydrobenzofuranyl groups.

One or more of the suitable substituents on the aromatic and heterocyclic group represented by A include hydroxy; amino group; halogen atoms such as chlorine, fluorine, bromine, iodine; substituted or unsubstituted $(C_1-C_{12})$alkyl group, especially, linear or branched $(C_1-C_6)$alkyl group, such as methyl, ethyl, n-propyl, isopropyl, n-butyl, iso-butyl, t-butyl, pentyl, hexyl and the like; cycloalkyl group such as cyclopropyl, cyclobutyl, cyclopentyl, cyclohexyl and the like; cycloalkyloxy group such as cyclopropyloxy, cyclobutyloxy, cyclopentyloxy, cyclohexyloxy and the like; aryl group such as phenyl or naphthyl, the aryl group may be substituted; aralkyl such as benzyl or phenethyl, the aralkyl group may be substituted; heteroaryl group such as pyridyl, thienyl, furyl, pyrrolyl, oxazolyl, thiazolyl, imidazolyl, oxadiazolyl, tetrazolyl, benzopyranyl, benzofuranyl and the like, the heteroaryl group may be substituted; heterocyclyl groups such as aziridinyl, pyrrolidinyl, morpholinyl, piperidinyl, piperazinyl and the like, the heterocyclyl group may be substituted; aryloxy such as phenoxy, naphthyloxy, the aryloxy group may be substituted; alkoxycarbonyl such as methoxycarbonyl or ethoxycarbonyl; aryloxycarbonyl group such as optionally substituted phenoxycarbonyl; arylamino group such as $HNC_6H_5$; amino$(C_1-C_6)$alkyl; hydroxy$(C_1-C_6)$alkyl; $(C_1-C_6)$alkoxy; thio$(C_1C_6)$alkyl; $(C_1-C_6)$ alkylthio; acyl group such as acetyl, propionyl or benzoyl, the acyl group may be substituted; acylamino groups such as $NHCOCH_3$, $NHCOC_2H_5$, $NHCOC_3H_7$, $NHCOC_6H_5$; aralkoxycarbonyl amino group such as $NHCOOCH_2C_6H_5$, alkoxycarbonylamino group such as $NHCOOC_2H_5$, $NHCOOCH_3$ and the like; carboxylic acid or its derivatives such as amides, like $CONH_2$, CONHMe, $CONMe_2$, CONHEt, $CONEt_2$, CONHPh and the like, the carboxylic acid derivatives may be substituted; acyloxy group such as OOCMe, OOCEt, OOCPh and the like which may optionally be substituted; sulfonic acid or its derivatives such as $SO_2NH_2$, $SO_2NHMe$, $SO_2NMe_2$, $SO_2NHCF_3$, $SO_2NHPh$ and the like; the sulfonic acid derivatives may be substituted.

All of the suitable substituents on group A may be substituted or unsubstituted.

When the substituents are further substituted, the substituents selected are from the same groups as those groups that substitute A and may be selected from halogen, hydroxy, or nitro, or optionally substituted groups selected from alkyl, cycloalkyl, alkoxy, cycloalkoxy, aryl, aralkyl, heterocyclyl, heteroaryl, heteroaralkyl, acyl, acyloxy, hydroxyalkyl, amino, acylamino, arylamino, aminoalkyl, aryloxy, alkoxycarbonyl, alkylamino, alkoxyalkyl, alkylthio, thioalkyl groups, carboxylic acid or its derivatives, or sulfonic acid or its derivatives.

Suitable linking group between N and X represented by B may contain 1–4 carbon atoms, 1–2 being preferred and suitable linking group between N and X represented by D may represent either a bond or contain 1–4 carbon atoms, 1–2 being preferred. The compounds according to formula (I) always have a linking group B and a linking group D. The linking group D having no carbon atom means that the linking group D represents a bond. B and D may contain no double bond or contain one to two double bonds, no double bond or one double bond being preferred. The substituents on the B and D include hydroxy; amino groups; halogen such as chlorine bromine, or iodine; optionally substituted linear or branched $(C_1-C_{12})$alkyl, especially $(C_1-C_6)$alkyl group such as methyl, hydroxymethyl, aminomethyl, methoxymethyl, trifluoromethyl, ethyl, isopropyl, hexyl etc; $(C_3-C_6)$cycloalkyl groups such as cyclopropyl, fluorocyclopropyl, cyclobutyl, cyclopentyl, fluorocyclopentyl, cyclohexyl, fluorocyclohexyl and the like; $(C_1-C_6)$alkoxy; $(C_3-C_6)$ cycloalkoxy; aryl such as phenyl; heterocyclic groups such as furyl, thienyl and the like; $(C_2-C_6)$ acyl; $(C_2-C_6)$acyloxy; hydroxy$(C_1-C_6)$alkyl; amino$(C_1-C_6)$alkyl; mono or di$(C_1-C_6)$alkylamino; cyclo $(C_3-C_5)$alkylamino groups; two substituents together with the adjacent carbon atoms to which they are attached may form a substituted or unsubstituted 5–7 membered cyclic structure which may or may not contain one or more hetero atoms selected from N, O, S; Such cyclic structures may or may not contain one or more double bonds. Preferred ring structures include phenyl, naphthyl, pyridyl, thienyl, furyl, oxazolyl, thiazolyl, furyl, isoxazolyl, azepinyl and the like. The substituents on such cyclic structure may be selected from the same group that may substitute the aromatic and heterocyclic group represented by A.

Suitable X includes $CH_2$, O, N or S group, preferably $CH_2$, N or O. Preferred ring structures comprise a nitrogen atom, linking groups represented by B and D, and X are pyrrolidinyl, piperidinyl, piperazinyl, aziridinyl and morpholinyl groups.

It is more preferred that the ring structure comprise a nitrogen atom, linking groups represented by B and D, and X and is a pyrrolidinyl group or a morpholinyl group.

The group represented by Ar includes divalent phenylene, naphthylene, pyridyl, quinolinyl, benzofuranyl, benzoxazolyl, benzothiazolyl, indolyl, indolinyl, azaindolyl, indenyl, pyrazolyl and the like. The substituents on the group represented by Ar include linear or branched optionally halogenated ($C_1$–$C_6$)alkyl and optionally halogenated ($C_1$–$C_3$)alkoxy, halogen, acyl, amino, acylamino, thio, carboxylic and sulfonic acids and their derivatives.

It is more preferred that Ar represents a substituted or unsubstituted divalent phenylene, naphthylene, benzofuranyl, indolyl, indolinyl, quinolinyl, azaindolyl, azaindolinyl, benzothiazolyl or benzoxazolyl group.

It is still more preferred that Ar is represented by divalent phenylene or naphthylene, which may be optionally substituted by methyl, halomethyl, methoxy or halomethoxy groups.

Suitable $R^1$ includes hydrogen; lower alkyl groups such as methyl, ethyl or propyl; hydroxy, ($C_1$–$C_3$)alkoxy; halogen atom such as fluorine, chlorine, bromine, or iodine or $R^1$ together with Y represent a bond.

Suitable Y group may be nitrogen or $CR^2$ where $R^2$ may be a hydrogen atom; hydroxy; ($C_1$–$C_3$)alkoxy; halogen; lower alkyl group or together with $R^1$ forms a bond.

It is preferred that $R^1$ and $R^2$ represent hydrogen atom or $R^1$ and $R^2$ together represent a bond.

Suitable Z group includes a hetero atom selected from O or S, with the provision that when Y is $CR^2$, Z is selected from sulfur or oxygen, and when Y is nitrogen, Z represents oxygen.

Suitable ring structure comprising Y and Z include 2,4-dioxooxazolidin-5-yl; 2,4-dioxothiazolidin-5-yl; and 3,5-dioxo-1,2,4-oxadiazolidin-2-yl groups. Preferred ring structures comprising Y and Z include 2,4-dioxooxazolidin-5-yl and 2,4-dioxothiazolidin-5-yl groups.

It is more preferred that the ring structure comprising Y and Z is a 2,4-dioxothiazolidin-5-yl group.

Suitable k is an integer ranging from 1 to 4, especially 1 to 2 and suitable p is an integer ranging from 0 to 4. It is preferred that p is 1 or 0. When p is zero $(CH_2)p$ represents a bond; the ring structure comprising N, X and the linking groups B and D is directly linked to the oxygen atom.

Pharmaceutically acceptable salts forming part of this invention include salts of the azolidinedione moiety such as alkali metal salts like Li, Na, and K salts, alkaline earth metal salts like Ca and Mg salts, salts of organic bases such as lysine, arginine, guanidine, diethanolamine, choline and the like, ammonium or substituted ammonium salts, salts of carboxy group wherever appropriate, such as aluminum, alkali metal salts, alkaline earth metal salts, ammonium or substituted ammonium salts. Salts may include acid addition salts which are, sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, ketoglutarates and the like. Pharmaceutically acceptable solvates may be hydrates or comprise other solvents of crystallization such as alcohols.

Particularly useful compounds according to the invention include:

5-[4-[N-(6-benzyloxy-2,5,7,8-tetramethylchroman-2-ylmethyl)-(2S)-pyrrolidine-2-methoxy]phenyl methylene]thiazolidine-2,4-dione and its salts;

5-[4-[N-(6-benzyloxy-2,5,7,8-tetramethylchroman-2-ylmethyl)-(2R)-pyrrolidine-2-methoxy]phenyl methylene]thiazolidine-2,4-dione, and its salts;

5-[4-[N-(6-benzyloxy-2,5,7,8-tetramethylchroman-2-ylmethyl)-(2S)-pyrrolidine-2-methoxy]phenyl methyl] thiazolidine-2,4-dione;

5-[4-[N-(6-benzyloxy-2,5,7,8-tetramethylchroman-2-ylmethyl)-(2R)-pyrrolidine-2-methoxy]phenyl methyl] thiazolidine-2,4-dione and its salts;

5-[4-[N-(6-benzyloxy-2,5,7,8-tetramethylchroman-2-ylmethyl)-(2S)-pyrrolidine-2-methoxy]phenyl methyl] thiazolidine-2,4-dione sodium salt;

5-[4-[N-(6-benzyloxy-2,5,7,8-tetramethylchroman-2-ylmethyl)-(2S)-pyrrolidine-2-methoxy]phenyl methyl] thiazolidine-2,4-dione maleic acid salt;

5-[4-[N-(6-benzyloxy-2,5,7,8-tetramethylchroman-2-ylmethyl)-(2S)-pyrrolidine-2-methoxy]phenyl methyl] thiazolidine-2,4-dione hydrochloride salt;

5-[4-[N-(6-hydroxy-2,5,7,8-tetramethylchroman-2-ylmethyl)-(2S)-pyrrolidine-2-methoxy]phenyl methyl] thiazolidine-2,4-dione;

5-[4-[N-(6-hydroxy-2,5,7,8-tetramethylchroman-2-ylmethyl)-(2R)-pyrrolidine-2-methoxy]phenyl methyl] thiazolidine-2,4-dione and its salts;

5-[4-[N-(6-hydroxy-2,5,7,8-tetramethylchroman-2-ylmethyl)-(2S)-pyrrolidine-2-methoxy]phenyl methyl] thiazolidine-2,4-dione sodium salt;

5-[4-[N-(6-hydroxy-2,5,7,8-tetramethylchroman-2-ylmethyl)-(2S)-pyrrolidine-2-methoxy]phenyl methyl] thiazolidine-2,4-dione maleic acid salt;

5-[4-[N-(6-hydroxy-2,5,7,8-tetramethylchroman-2-ylmethyl)-(2S)-pyrrolidine-2-methoxy]phenyl methyl] thiazolidine-2,4-dione hydrochloride salt;

5-[4-[N-[6-hydroxy-2,5,7,8-tetramethylchroman-2-ylmethyl]-(2S)-pyrrolidine-2-methoxy]phenyl methylene]thiazolidine-2,4-dione;

5-[4-[N-(6-hydroxy-2,5,7,8-tetramethylchroman-2-ylmethyl)-(2R)-pyrrolidine-2-methoxy]phenyl methylene]thiazolidine-2,4-dione and its salts;

5-[4-[N-(2,3-dihydro-5-benzyloxy-2,2,4,6,7-pentamethylbenzofuran-3-ylmethyl]-(2S)-pyrrolidine-2-methoxy]phenyl methylene)thiazolidine-2,4-dione;

5-[4-[N-(2,3-dihydro-5-benzyloxy-2,2,4,6,7-pentamethylbenzofuran-3-ylmethyl]-(2R)-pyrrolidine-2-methoxy)phenyl methylene]thiazolidine-2,4-dione and its salts;

5-[4-[N-(2,3-dihydro-5-benzyloxy-2,2,4,6,7-pentamethylbenzofuran-3-ylmethyl]-(2S)-pyrrolidine-2-methoxy)phenyl methylene]thiazolidine-2,4-dione maleic acid salt;

5-[4-[N-[2,3-dihydro-5-benzyloxy-2,2,4,6,7-pentamethylbenzofuran-3-ylmethyl]-(2S)-pyrrolidine-2-methoxy]phenyl methylene]thiazolidine-2,4-dione hydrochloride salt;

5-[4-[N-(2,3-dihydro-5-benzyloxy-2,2,4,6,7-pentamethylbenzofuran- 3-ylmethyl]-(2S)-pyrrolidine-2-methoxy] phenyl methyl)thiazolidine-2,4-dione;

5-[4-[N-(2,3-dihydro-5-benzyloxy-2,2,4,6,7-pentamethylbenzofuran-3-ylmethyl]-(2R)-pyrrolidine-2-methoxy) phenyl methyl]thiazolidine-2,4-dione and its salts;

5-[4-[N-(2,3-dihydro-5-benzyloxy-2,2,4,6,7-pentamethylbenzofuran-3-ylmethyl]-(2S)-pyrrolidine-2-methoxy)phenyl methyl]thiazolidine-2,4-dione maleic acid salt;

5-[4-[N-(2,3-dihydro-5-benzyloxy-2,2,4,6,7-pentamethylbenzofuran-3-ylmethyl]-(2S)-pyrrolidine-2-methoxy)phenyl methyl]thiazolidine-2,4-dione hydrochloride salt;

5-[4-[N-(2,3-dihydro-5-hydroxy-2,2,4,6,7-pentamethylbenzofuran-3-ylmethyl)-(2S)-pyrrolidine-2-methoxy]phenyl methyl]thiazolidine-2,4-dione;

5-[4-[N(2,3-dihydro-5-hydroxy-2,2,4,6,7-pentamethylbenzofuran-3-ylmethyl)-(2R)-pyrrolidine-2-methoxy]phenyl methyl]thiazolidine-2,4-dione and its salts;

5-[4-[N-(2,3-dihydro-5-hydroxy-2,2,4,6,7-pentamethylbenzofuran-3-ylmethyl)-(2S)-pyrrolidine-2-methoxy]phenyl methyl]thiazolidine-2,4-dione hydrochloride salt;

5-[4-[N-(2,3-dihydro-5-hydroxy-2,2,4,6,7-pentamethylbenzofuran-3-ylmethyl)-(2S)-pyrrolidine-2-methoxy]phenyl methylene]thiazolidine-2,4-dione;

5-[4-[N-(2,3-dihydro-5-hydroxy-2,2,4,6,7-pentamethylbenzofuran-3-ylmethyl)-(2R)-pyrrolidine-2-methoxy]phenyl methylene]thiazolidine-2,4-dione and its salts;

5-[4-[N-(5-benzyloxy-2-methylbenzofuran-3-ylmethyl)-(2S)-pyrrolidine-2-methoxyphenyl methylene]thiazolidine-2,4-dione;

5-[4-[N-(5-benzyloxy-2-methylbenzofuran-3-ylmethyl)-(2S)-pyrrolidine-2-methoxy]phenyl methylene]thiazolidine-2,4-dione sodium salt, and 5-[4-[N-(5-benzyloxy-2-methylbenzofuran-3-ylmethyl)-(2S)-pyrrolidine-2-methoxy]phenyl methyl]thiazolidine-2,4-dione.

According to a feature of the present invention, there is provided a process for the preparation of novel intermediate of the general formula (III)

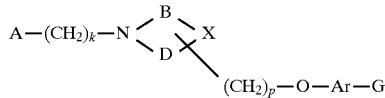

where A, B, D, X, Ar, k and p are as defined in formula (I) and G is as defined above.

In an embodiment of the invention, the novel intermediate of the general formula (III) defined above where G is CHO or NO$_2$ group, can be prepared by reacting the compound of the general formula (IV),

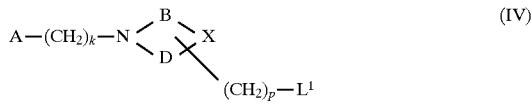 (IV)

wherein, A, B, D, X, k and p are as defined earlier and L$^1$ is a halogen atom such as chlorine, bromine or iodine or a leaving group such as methanesulfonate, trifluoromethanesulfonate, p-toluenesulfonate and the like with a compound of the formula (V)

 (V)

where G is a CHO or a NO$_2$ group and Ar is as defined earlier.

The reaction of compound of formula (IV) with the compound of formula (V) to produce a compound of formula (III) may be carried out in the presence of solvents such as THF, DMF, DMSO, DMB and the like. Mixtures of solvents may be used. An inert atmosphere may be used and may be maintained by using inert gases such as N$_2$, Ar or He. The reaction may be effected in the presence of a base such as K$_2$CO$_3$, Na$_2$CO$_3$, NaH, or mixtures thereof The reaction temperature may range from 20° C. to 150° C., preferably at a temperature in the range of 30° C. to 100° C. The duration of the reaction may range from 1 to 24 hours, preferably from 2 to 6 hours.

In another embodiment of the present invention, the novel intermediate of general formula (III), where G is a CHO or NO$_2$ group, can also be prepared by the reaction of compound of general formula (VI)

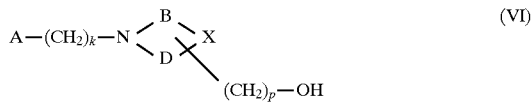 (VI)

where A, B, D, X, k and p are as defined earlier with a compound of general formula (VII)

 (VII)

where G is a CHO or NO$_2$ group and Ar is as defined earlier and L$^2$ represents a halogen atom such as chlorine or fluorine.

The reaction of compound of formula (VI) with a compound of formula (VII) to produce a compound of the formula (III) may be carried out in the presence of solvents such as THF, DMF, DMSO, DME and the like or mixtures thereof. The reaction may be carried out in an inert atmosphere which is maintained by using inert gases such as N$_2$, Ar, or He. The reaction may be effected in the presence of a base such as K$_2$CO$_3$, Na$_2$CO$_3$ or NaH or mixtures thereof. The reaction temperature may range from 20° C. to 120° C., preferably at a temperature in the range of 30° C. to 100° C. The duration of the reaction may range from 1 to 12 hours, preferably from 2 to 6 hours.

The novel intermediate of formula (III) can also be obtained by the reaction of a compound of general formula (VI) defined above with a compound of general formula (V) defined earlier.

The reaction of compound of general formula (VI) with a compound of general formula (V) may be carried out using suitable coupling agents such as dicyclohexyl urea, triarylphosphine/dialkylazadicarboxylate such as PPh$_3$/DEAD and the like. The reaction may be carried out in the presence of solvents such as THF, DME, CH$_2$Cl$_2$, CHCl$_3$, toluene, acetonitrile, carbontetrachloride and the like. The reaction may be carried out in an inert atmosphere which may be maintained by using inert gases such as N$_2$, Ar, or He. The reaction may be effected in the presence of DMAP, HOBT and they may be used in the range of 0.05 to 2 equivalents, preferably 0.25 to 1 equivalents. The reaction temperature may be in the range of 0° C. to 100° C., preferably at a temperature in the range of 20° C. to 80° C. The duration of the reaction may range from 0.5 to 24 hours, preferably from 6 to 12 hours.

In another embodiment of this invention, there is provided a process for the preparation of a compound of general formula (III) where G is a CHO or a NO$_2$ group, and other symbols are as defined earlier which comprises reacting a compound of general formula (VIII)

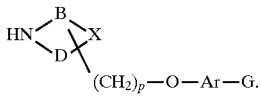

(VIII)

where B, D, X, Ar and p are as defined earlier, with a compound of general formula (IX)

$$A-(CH_2)_k-L^1 \quad (IX)$$

where A, $L^1$ and k are as defined earlier.

The reaction of compound of general formula (VIII) with a compound of general formula (IX) may be carried out neat or in the presence of solvents such as DMF, DMSO, $CH_3CN$, EtOH, or acetone. The reaction may be carried out in the inert atmosphere which may be maintained by using inert gases such as $N_2$, Ar, or He. The reaction may be an inert atmosphere and effected in the presence of base such as $K_2CO_3$, $Na_2CO_3$, KOH, NaOH, NaH and the like or mixtures thereof. The amount of base may range from 1 to 20 equivalents, preferably 1 to 10 equivalents. The reaction may be carried out at a temperature in the range 20° C. to 180° C., preferably at a temperature in the range 50° C. to 150° C. Duration of the reaction may range from 1 to 48 hours, preferably from 1 to 12 hours. The amounts of the compound of general formula (VIII) and (IX) may range from 1 to 20 equivalents, preferably from 1 to 5 equivalents.

The compound of general formula (VIII) in turn can be prepared by reacting a compound of general formula (X)

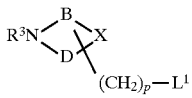

(X)

where B, D, $L^1$, X and p are as defined earlier and $R^3$ is a hydrogen atom or a protecting group, with a compound of general formula (V) followed by removal of N-protecting group using conventional methods.

The reaction of compound of general formula (X) with a compound of general formula (V) may be carried out in the presence of solvents such as THF, DMF, DMSO, DME and the like or mixtures thereof. The inert atmosphere may be maintained by using inert gases such as $N_2$, Ar, or He. The reaction may be effected in the presence of a base such as $K_2CO_3$, $Na_2CO_3$, NaH and the like or mixtures thereof. The reaction temperature may range from 20° C. to 120° C., preferably at a temperature in the range of 30° C. to 80° C. The duration of the reaction may range from 1 to 24 hours, preferably from 2 to 12 hours.

The compound of general formula (VIII) can also be prepared by reacting a compound of general formula (XI)

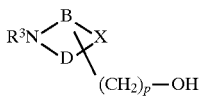

(XI)

where B, D, X, p, and $R^3$ are as defined earlier, with a compound of general formula (V) or with a compound of general formula (VII) defined earlier.

The reaction of compound of general formula (XI) with compound of general formula (V) may be carried out out using suitable coupling agents such as dicyclohexyl urea, triarylphosphine/dialkylazadicarboxylate such as $PPh_3$/DEAD and the like. The reaction may be carried out in the presence of solvents such as THF, DME, $CH_2Cl_2$, $CHCl_3$, toluene, acetonitrile, carbontetrachloride and the like. The reaction may be carried out in an inert atmosphere and it may be maintained by using inert gases such as $N_2$, Ar, or He. The reaction may be effected in the presence of DMAP, HOBT and they may be used in the range of 0.05 to 2 equivalents, preferably 0.25 to 1 equivalents. The reaction temperature may be in the range of 0° C. to 100° C., preferably at a temperature in the range of 20° C. to 80° C. The duration of the reaction may range from 0.5 to 24 hours, preferably from 6 to 12 hours.

The reaction of compound of general formula (XI) with a compound of general formula (VII) to produce a compound of general formula (VIII) may be carried out in the presence of solvents such as THF, DMF, DMSO, DME and the like or mixtures thereof. The reaction may be carried out in an inert atmosphere which is maintained by using inert gases such as $N_2$, Ar, or He. The reaction may be effected in the presence of a base such as $K_2CO_3$, $Na_2CO_3$ or NaH or mixtures thereof. The reaction temperature may range from 20° C. to 120° C., preferably at a temperature in the range of 30° C. to 100° C. The duration of the reaction may range from 1 to 12 hours, preferably from 2 to 6 hours.

The present invention provides a process for the preparation of novel azolidinedione derivatives of general formula (I), their tautomeric forms, their stereoisomers, their polymorphs, their pharmaceutically acceptable salts and their pharmaceutically acceptable solvates wherein $R^1$ and Y together represent a bond and Z represents a sulfur or oxygen atom and all symbols are as defined earlier which comprises:

reacting the compound of general formula (III), where G is a CHO group with 2,4-thiazolidinedione or 2,4-oxazolidinedione to yield a compound of general formula (XII)

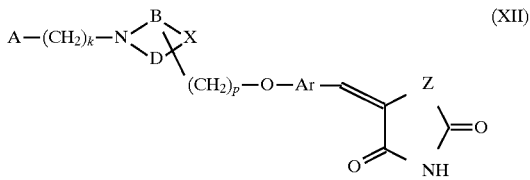

(XII)

where A, B, D, X, Ar, k, p and Z are as defined earlier and removing the water formed during the reaction by conventional methods.

The reaction between the compound of the general formula (III) where G is a CHO group with 2,4-thiazolidinedione or 2,4-oxazolidinedione to yield a compound of general formula (XII) may be carried out neat in the presence of sodium acetate or in the presence of a solvent such as benzene, toluene, methoxyethanol or mixtures thereof. The reaction temperature may range from 80° C. to 140° C. depending upon the solvents employed and in the range from 80° C. to 180° C. when the reaction is carried out neat in the presence of sodium acetate. Suitable catalyst such as piperidinium acetate or benzoate, sodium acetate or mixtures of catalysts may also be employed. Sodium acetate can be used in the presence of solvent, but it is preferred that sodium acetate is used neat. The water produced in the reaction may be removed, for example, by using Dean Stark water separator or by using water absorbing agents like molecular sieves. Oxazolidine-4-oxo-2-thione may be used instead of 2,4-oxazolidinedione. However, the thio group needs to be converted to oxo group by oxidation using agents such as hydrogen peroxide or peroxyacids like mCPBA.

The compound of the general formula (XII) obtained in the manner described above is reduced by known methods to obtain the compound of general formula (XIII)

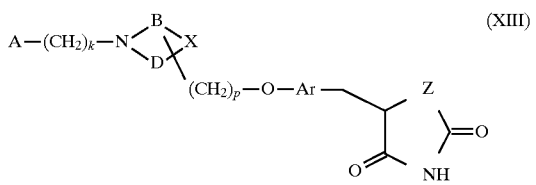

where A, B, D, X, Ar, k, p and Z are as defined earlier. The compound of general formula (XIII) represents the compound of general formula (I), wherein $R^1$ is hydrogen and Y is $CR^2$ where $R^2$ is hydrogen atom and all other symbols are as defined earlier.

The reduction of compound of the formula (XII) to yield a compound of the general formula (XIII) may be carried out in the presence of gaseous hydrogen and a catalyst such as Pd/C, Rh/C, Pt/C, and the like. Mixtures of catalysts may be used. The reaction may also be conducted in the presence of solvents such as dioxane, acetic acid, ethyl acetate and the like. Mixtures of solvents may be used. A pressure between atmospheric pressure and 80 psi may be employed. The catalyst may be 5–10% Pd/C and the amount of catalyst used may range from 50–300% w/w. The reaction may also be carried out by employing metal solvent reduction such as magnesium in methanol or sodium amalgam in methanol. The reaction may also be carried out with alkali metal borohydrides such as $LiBH_4$, $NaBH_4$, $KBH_4$ and the like in the presence of cobalt salt such as $CoCl_2$ and ligands, preferably bidentated ligands such as 2,2'-bipyridyl; 1,10-phenanthroline; bisoximes and the like.

The compound of the general formula (XII) and of general formula (XIII) obtained above may be converted into pharmaceutically acceptable salts, or pharmaceutically acceptable solvates by conventional methods.

In yet another embodiment of the present invention, the compound of the general formula (I) can also be prepared by reacting a compound of the general formula (IV) defined above with a compound of general formula (XIV)

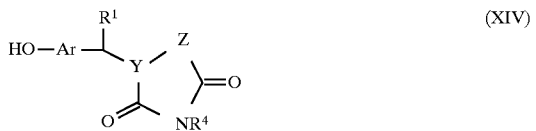

where $R^1$, Y, Z and Ar are as defined earlier and $R^4$ is hydrogen or a nitrogen protecting group which is removed after the reaction.

The reaction of compound of general formula (IV) with a compound of general formula (XIV) to produce a compound of general formula (I) may be carried out in the presence of solvents such as THF, DMF, DMSO, DME and the like or mixtures thereof. The reaction may be carried out in an inert atmosphere which is maintained by using inert gases such as $N_2$, Ar or He. The reaction may be effected in the presence of a base such as alkalis like sodium hydroxide or potassium hydroxide; alkali metal carbonates like sodium carbonate or potassium carbonate; alkali metal hydrides such as sodium hydride; organometallic bases like n-butyl lithium; alkali metal amides like sodamide, or mixtures thereof. Multiple solvents and bases can be used. The amount of base may range from 1 to 5 equivalents, preferably 1 to 3 equivalents. The reaction temperature may be in the range of 0° C. to 120° C., preferably at a temperature in the range of 20° C. to 100° C. The duration of the reaction may range from 0.5 to 24 hours, preferably from 0.5 to 6 hours.

The removal of protecting groups may be carried out by conventional methods which include treatment with acid such as, hydrochloric acid, trifluoroacetic acid or bases such as, KOH, NaOH, $Na_2CO_3$, $NaHCO_3$, $K_2CO_3$ and the like or mixtures thereof. These reagents may be used as aqueous solution or as solutions in alcohols like methanol, ethanol etc. Deprotection can also be effected by gaseous hydrogen in the presence of catalyst such as Pd/carbon or conventional transfer hydrogenation methods when the protecting group is a benzyl or substituted benzyl group.

The compound of general formula (I) can also be obtained by reacting a compound of general formula (VI) with a compound of general formula (XIV).

The reaction of compound of general formula (VI) with a compound of general formula (XIV) to produce a compound of general formula (I) may be carried out using suitable coupling agents such as dicyclohexyl urea, triarylphosphine dialkylazadicarboxylate such as $PPh_3$/DEAD, and the like. The reaction may be carried out in the presence of solvents such as THF, DME, $CH_2Cl_2$, $CHCl_3$, toluene, acetonitrile, carbontetrachloride and the like. An inert atmosphere may be used and the inert atmosphere may be maintained by using inert gases such as $N_2$, Ar, or He. The reaction may be effected in the presence of DMAP-HOBT and they may be used in the range of 0.05 to 2 equivalents, preferably 0.25 to 1 equivalents. The reaction temperature may be in the range of 0° C. to 100° C., preferably at a temperature in the range of 20° C. to 80° C. The duration of the reaction may range from 0.5 to 24 hours, preferably from 6 to 12 hours.

In another embodiment of the present invention, the compound of general formula (I), where A, B, D, X, k, p and Ar are as defined earlier and $R^1$ represents hydrogen, Y represents CH and Z represents a oxygen or a sulfur atom can be prepared by the reaction of compound of general formula (XV)

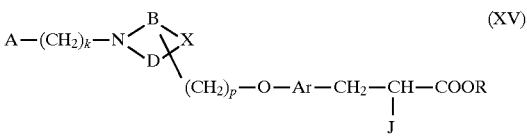

where A, B, D, X, k, p and Ar are as defined earlier, J is a halogen atom like chlorine, bromine or iodine or a hydroxy group and R is a lower alkyl group, with thiourea when J is a halogen atom, or with urea when J is a hydroxy group followed by treatment with an acid.

The reaction of compound of general formula (XV) with thiourea or urea is normally carried out in the presence of alcoholic solvent such as methanol, ethanol, propanol, isobutanol, 2-methoxybutanol, etc or DMSO or sulfolane. The reaction may be conducted at a temperature in the range between 20° C. and the reflux temperature of the solvent used. Bases such as NaOAc, KOAc, NaOMe, NaOEt etc. can be used. The reaction is normally followed by treatment with a mineral acid such as hydrochloric acid at 20° C. to 100° C.

The compound of general formula (XV) where J is hydroxy group is prepared by the reaction of compound of general formula (XV) where J is a halogen atom with aqueous alkali at a temperature ranging from 20° C. to 100° C. followed by reesterification of the hydrolysed acid group during the reaction, by conventional methods.

The compound of general formula (XV) where J is a OH group may also be prepared from compound of formula (XV) where J is a halogen atom by reacting with formamide in the presence of water. The amount of formamide used in the reaction ranges from 0.5 to 1.5 mL and water used ranges from 20 μL to 0.1 mL for one mmol of the halo compound (XV). The reaction is conducted at a temperature ranging from 80° C. to 180° C., preferably from 120° C. to 150° C., over a period ranging from 1 to 8 hours.

The compound of general formula (XV) where J is a halogen atom can be prepared by the diazotization of the amino compound of the general formula (XVI)

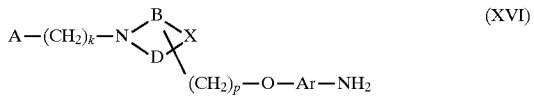

(XVI)

where all symbols are as defined earlier, using alkali metal nitrites followed by treatment with acrylic acid esters in the presence of hydrohalo acids and catalytic amount of copper oxide or copper halide.

The compound of general formula (XVI) can in turn be prepared by the conventional reduction of the novel intermediate (III) where G is $NO_2$ group and other symbols are as defined earlier.

The intermediates of the formula (VI) defined above can be prepared by a process which comprises reacting a compound of general formula (IX) defined earlier with a compound of general formula (XVII)

(XVII)

where B, D, X and p are as defined earlier, and $R^6$ is a hydroxy group or a group, such as carboxylic acid group, ester, amide, ether and the like, which can be converted to hydroxy group by conventional methods.

The reaction of compound of general formula (XVII) with a compound of general formula (IX) to yield a compound of general formula (VI) may be carried out in neat or in the presence of solvents such as DMF, DMSO, $CH_3CN$, EtOH, or acetone. The reaction may be conducted in an inert atmosphere and the inert atmosphere is maintained by using inert gases such as $N_2$, Ar, or He. The reaction may be effected in the presence of base such as $K_2CO_3$, $Na_2CO_3$, KOH, NaOH, NaH and the like. The amount of base may range from 1 to 20 equivalents, preferably 1 to 10 equivalents. The reaction may be carried out at a temperature in the range 20° C. to 180° C., preferably at a temperature in the range 50° C. to 150° C. Duration of the reaction may range from 1 to 48 hours, preferably from 1 to 12 hours. The amounts of the compound of general formula (XVII) and (IX) may range from 1 to 20 equivalents, preferably from 1 to 5 equivalents.

The compound of general formula (VI) where k=1 can also be prepared by reacting the compound of general formula (XVII) defined above in the presence of formaldehyde solution or a source of formyl moiety thereof, with A–H where A may be substituted or unsubstituted single or fused aromatic or heterocycle or their tautomeric forms. Suitable catalyst may be employed.

The reaction of compound of general formula (XVII) with A–H to yield a compound of general formula (VI) where k=1, may be carried out using formaldehyde, paraformaldehyde, $POCl_3$-DMF and the like. The reaction may be carried out in the presence of solvents such as methanol, ethanol, 2-methoxyethanol or neat. These reagents may be used in the range of 1 to 4 equivalents, preferably 1 to 2 equivalents. The reaction may be carried out at a temperature in the range of –10° C. to 100° C., preferably from 0° C. to 90° C. Duration of the reaction may range from 1 to 24 hours, preferably from 2 to 12 hours.

In yet another embodiment of the present invention, the compound of general formula (I), where A, B, D, X, Ar, k and p are as defined earlier and Y is nitrogen atom and Z is oxygen atom can be prepared by a process which comprises: reaction of novel intermediate of formula (III) defined earlier, where G represents a CHO group with $NH_2OH.HCl$ to yield a compound of general formula (III) where G represents CH=NOH group and all symbols are as defined earlier, followed by metal borohydride reduction to yield a compound of general formula (XVIII)

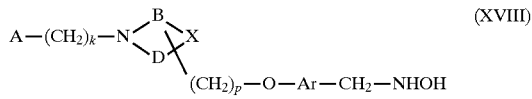

(XVIII)

where all symbols are as defined earlier.

The reaction of compound of general formula (III), where G is CHO group and other symbols are as defined earlier, with hydroxylamine hydrochloride is carried out in solvents such as ethanol, methanol, THF, dioxane and the like following the conventional method to make oximes. 1 to 10 equivalents of $NH_2OH.HCl$ may be used, preferably, 2 to 5 equivalents. Bases such as alkali metal acetates or ammonium acetate may be used. Reaction may be carried out in the presence of water. Temperature in the range of 0° C. to reflux temperature of the solvent may be used. The oxime obtained in the manner described above is reduced using reducing agents such as alkali metal borohydrides like sodium borohydride or sodium cyanoborohydride or borane reagents using conventional conditions to yield the compound of general formula (XVIII).

The compound of general formula (XVIII) in turn is reacted with halocarbonyl isocyanate or alkoxycarbonyl isocyanate to yield a compound of general formula (I) or with KOCN to yield a compound of general formula (III) where G is $CH_2N(OH)CONH_2$, followed by treatment with carbonylating agents such as alkylhaloformate to produce the compound of general formula (I) where A, B, D, X, Ar, p and k are as defined earlier, Y represents nitrogen atom and Z is oxygen atom.

The reaction of compound of general formula (XVIII) with halocarbonyl isocyanate such as chlorocarbonyl isocyanate or alkoxycarbonyl isocyanate such as ethoxycarbonyl isocyanate may be carried out in inert solvents such as THF, dioxane, etc. at a temperature in the range –15° C. to 50° C. The reaction may be carried out for 0.5 to 12 hours depending on the substrates used for the reaction.

Alternatively, the compound of general formula (XVIII) may be treated with excess of KOCN in organic acids such as acetic acid. Water may be used in the reaction. The reaction may be carried out at a temperature in the range of 20° C. to 120° C. The product isolated in the reaction is further treated with alkyl haloformate such as ethyl chloroformate in the presence of 1 to 10 equivalents of alkali such as sodium hydroxide, potassium hydroxide and the like to obtain compound of general formula (I) where all the symbols are as defined earlier and Y represents nitrogen atom and Z represents oxygen atom.

The pharmaceutically acceptable salts are prepared by reacting the compound of formula (I) with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, guanidine and their derivatives etc. may also be used. Alternatively, acid addition salts are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid, salicylic acid, hydroxynaphthoic acid, ascorbic acid, palmitic acid, succinic acid, benzoic acid, benzene sulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid and the like or chiral bases such as brucine, cinchona alkaloids and their derivatives and the like.

Various polymorphs of compound of general formula (I) forming part of this invention may be prepared by crystallization of compound of formula (I) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or slow cooling. The presence of polymorphs may be determined by solid probe NMR spectroscopy, IR spectroscopy, differential scanning calorimetry, powder X-ray data or such other techniques.

The present invention also provides a pharmaceutical composition, containing the compounds of the general formula (I), as defined above, their tautomeric forms, their stereoisomers, their polymorphs, their pharmaceutically acceptable salts, their pharmaceutically acceptable solvates in combination with the usual pharmaceutically employed carriers, diluents and the like, useful for the treatment and/or prophylaxis of diseases in which insulin resistance is the underlying pathophysiological mechanism such as type II diabetes, impaired glucose tolerance, dyslipidaemia, hypertension, coronary heart disease and other cardiovascular disorders including atherosclerosis; insulin resistance associated with obesity and psoriasis, for treating diabetic complications and other diseases such as polycystic ovarian syndrome (PCOS), certain renal diseases including diabetic nephropathy, glomerulonephritis, glomerular sclerosis, nephrotic syndrome, hypertensive nephrosclerosis, end-stage renal diseases and microalbuminuria as well as certain eating disorders, as aldose reductase inhibitors and for improving cognitive functions in dementia.

The pharmaceutical composition may be in the forms normally employed, such as tablets, capsules, powders, syrups, solutions, suspensions and the like, may contain flavorants, sweeteners etc. in suitable solid or liquid carriers or diluents, or in suitable sterile media to form injectable solutions or suspensions. Such compositions typically contain from 1 to 25%, preferably 1 to 15% by weight of active compound, the remainder of the composition being pharmaceutically acceptable carriers, diluents or solvents.

A typical tablet production method is exemplified below:

Tablet Production Example

| a) | 1) Active ingredient | 30 g |
|----|---|---|
| | 2) Lactose | 95 g |
| | 3) Corn starch | 30 g |
| | 4) Carboxy methyl cellulose | 44 g |
| | 5) Magnesium stearate | 1 g |
| | | 200 g for 1000 tablets |

The ingredients 1–3 are uniformly blended with water and granulated after drying under reduced pressure. The ingredients 4 & 5 are mixed well with the granules and compressed by a tabletting machine to prepare 1000 tablets each containing 30 mg of ingredient.

| b) | 1) Active ingredient | 30 g |
|----|---|---|
| | 2) Calcium phosphate | 90 g |
| | 3) Lactose | 40 g |
| | 4) Corn starch | 35 g |
| | 5) Polyvinyl pyrrolidone | 3.5 g |
| | 6) Magnesium stearate | 1.5 g |
| | | 200 g for 1000 tablets |

The ingredients 1–4 are uniformly moistened with an aqueous solution of 5 and granulated after drying under reduced pressure. Ingredient 6 is added and granules are compressed by a tabletting machine to prepare 1000 tablets containing 30 mg of ingredient 1.

The compound of the formula (I) as defined above are clinically administered to mammals, including man, via either oral or parenteral routes. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 200 mg/kg body weight of the subject per day or preferably about 0.10 to about 50 mg/kg body weight per day administered singly or as a divided dose. However, the optimum dosage for the individual subject being treated will be determined by the person responsible for treatment, generally smaller doses being administered initially and thereafter increments made to determine the most suitable dosage.

Suitable pharmaceutically acceptable carriers include solid fillers or diluents and sterile aqueous or organic solutions. The active compound will be present in such pharmaceutical compositions in amounts sufficient to provide the desired dosage in the range as described above. Thus, for oral administration, the compounds can be combined with a suitable solid or liquid carrier or diluent to form capsules, tablets, powders, syrups, solutions, suspensions and the like. The pharmaceutical compositions, may, if desired, contain additional components such as flavorants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or alkali or alkaline earth metal salts of the compounds. The injectable solutions prepared in this manner can then be, administered intravenously, intraperitoneally, subcutaneously, or intramuscularly, with intramuscular administration being preferred in humans.

The invention is explained in detail in the examples given below which are provided by way of illustration only and therefore should not be construed to limit the scope of the invention.

PREPARATION 1

N-[(2RS)-6-Benzyloxy-2,5,7,8-tetramethylchroman-2-ylmethyl]-(2S)-pyrrolidine-2-methanol

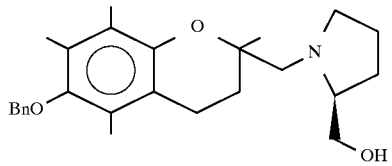

A mixture of (2RS)-6-benzyloxy-2,5,7,8-tetramethylchroman-2-ylmethyl methanesulphgnate (100 g) and L-prolinol (100 g) was heated under nitrogen atmosphere at 120° C. with stirring for 6 h. The mixture was cooled to room temperature and poured into water and the solution was extracted with $CH_2Cl_2$ repeatedly. The combined organic extracts were washed with brine, dried ($Na_2SO_4$) and evaporated to dryness under reduced pressure to give 101 g (100%) of the crude compound which was chromatographed on silica gel using 0.5% methanol in chloroform to afford 75.7 g (75%) of the title compound as a thick liquid.

$[\alpha]_D^{27}$=-9.5 (c, 1.0, $CHCl_3$).

$^1$H NMR ($CDCl_3$, 200 MHz): δ1.19, 1.25 (2S, 3H), 1.55–2.05 (m, 6H), 2.11 (s, 3H), 2.18 (s, 3H), 2.22 (s, 3H), 2.35–3.0 (m, 6H), 3.25–3.75 (m, 3H), 4.7 (s, 2H), 7.2–7.6 (m, 5H).

PREPARATION 2

N-[(3RS)-5-Benzyloxy-2,3-dihydro-2,2,4,6,7-pentamethylbenzofuran-3-ylmethyl]-(2S)-pyrrolidine-2-methanol

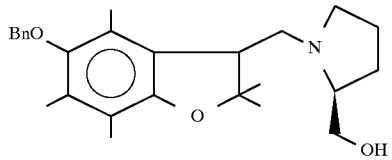

The title compound (1 g, 66%) was prepared as a pale yellow solid from (3RS)-5-benzyloxy-2,3-dihydro-2,2,4,6,7-pentamethylbenzofuran-3-ylmethyl methanesulfonate (1.49 g) and L-prolinol (1.5 g) by an analogous procedure to that described in preparation 1, mp 99°–101° C.

$[\alpha]_D^{26}$=-32.8 (c, 1.0, $CHCl_3$).

$^1$H NMR ($CDCl_3$, 200 MHz): δ1.30, 1.34 (2s, 3H), 1.58, 1.62 (2s, 3H), 1.78 (m, 4H), 2.12 (s, 3H), 2.20, 2.22 (2s, 3H), 2.28, 2.30 (2s, 3H), 2.33 (m, 2H), 2.68 (d, J=6.0 Hz, 1H), 3.09 (m, 1H), 3.30 (m, 2H), 3.36 (m, 1H), 3.68 (m, 1H), 4.76 (s, 2H), 7.46 (m, 5H).

PREPARATION 3

N-[5-Benzyloxy-2,4,6,7-tetramethylbenzofuran-3-ylmethyl]-(2S)-pyrrolidine-2-methanol

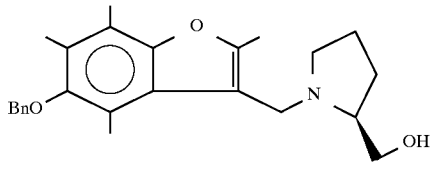

The title compound (7.5 g, 69%) was prepared as a white solid from 5-benzyloxy-2,4,6,7-tetramethylbenzofuran-3-methylchloride (9.0 g) and L-prolinol (4.15 g) by an analogous procedure to that described in preparation 1. mp 98°–100° C.

$[\alpha]_D^{20}$=-15.5 (c, 1.0, $CHCl_3$)

$^1$H NMR ($CDCl_3$, 200 MHz): δ1.85 (m, 4H), 2.36 (s, 3H), 2.41 (s, 3H), 2.48 (s, 3H), 2.50 (m, 1H), 2.64 (s, 3H), 2.76 (m, 1H), 3.04 (m, 1H), 3.34 (dd, J=10.8 and 2.5 Hz, 1H)), 3.51 (dd, J 10.2, 3.5 Hz, 1H), 3.60 (d, J=13.2 Hz, 1H), 3.95 (d, J=13.2 Hz, 1H), 4.78 (s, 2H), 7.48 (m, 5H).

PREPARATION 4

N-(5-Benzyloxy-2-methylbenzofuran-3-ylmethyl)-(2S)-pyrrolidine-2-methanol

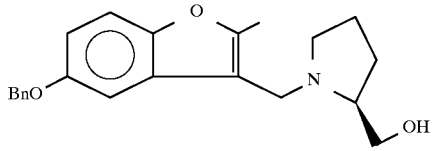

The title compound (4.1 g, 67%) was prepared as an oil from 5-benzyloxy-2-methylbenzofuran-3-methylchloride (5.0 g) and L-prolinol (1.76 g) by an analogous procedure to that described in preparation 1.

$[\alpha]_D^{21}$=-26.3 (c, 0.5, $CHCl_3$)

$^1$H NMR ($CDCl_3$, 200 MHz): δ1.63 (m, 2H), 1.88 (m, 2H), 2.32 (m, 1H), 2.43 (s, 3H), 2.75 (m, 1H), 2.92 (m, 1H), 3.41 (m, 2H), 3.75 (dd, J=10.7 Hz and 3.34 Hz, 1H), 3.90 (d, J=13.3 Hz, 1H), 5.09 (s, 2H), 6.89 (m, 1H), 7.06 (m, 1H), 7.45 (m, 6H).

PREPARATION 5

N-(1-Methylindol-3-ylmethyl)-(2S)-pyrrolidine-2-methanol

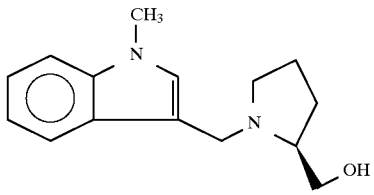

To a mixture of formalin (0.33 ml, 48% in $H_2O$) and acetic acid (0.9 ml) was added L-prolinol (0.43 g) with stirring under ice-cooling. After 5 min, 1-methyl indole (0.56 g) was added dropwise to the above reaction mixture, and stirring was continued for 2 h. At the end of this time, reaction mixture was basified with 2N NaOH; the oily residue was extracted with ethyl acetate, dried ($Na_2SO_4$), and the solvent was evaporated to dryness to give the title compound (0.87 g, 83%), as a white solid, mp. 46°–48° C.

$[\alpha]_D^{25}$=−65.1 (c, 1.0, $CH_3OH$)

$^1$H NMR ($CDCl_3$, 200 MHz): δ1.68 (m, 2H), 1.85 (m, 2H), 2.36 (q, J=9.3 Hz and 16.9 Hz, 1H), 2.75 (m, 1H), 3.03 (m, 1H), 3.42 (d, J=9.9 Hz, 1H), 3.56 (d, J=13.3 Hz, 1H), 3.79 (m, 4H), 4.08 (d, J=13.3 Hz, 1H), 6.96 (s, 1H), 7.20 (m, 3H), 7.70 (d, J=7.75 Hz, 1H).

PREPARATION 6

1-[(2RS)-6-Benzyloxy-2,5,7,8-tetramethylchroman-2-ylmethyl]piperazine

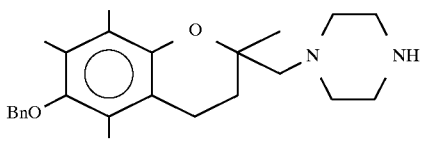

The title compound (7 g, 47%) was prepared as a syrupy liquid from (2RS)-6-benzyloxy-2,5,7,8-tetramethyl-chroman-2-ylmethyl methanesulphonate (15 g) and piperazine (19 g) by an analogous procedure to that described in preparation 1.

$^1$H NMR ($CDCl_3$, 200 MHz): δ1.22 (s, 3H), 1.7 (m, 1H), 1.95 (m, 1H), 2.03 (s, 3H), 2.17 (s, 3H), 2.21 (s, 3H), 2.60 (m, 4H), 2.95 (m, 4H), 3.2 (m, 4H), 4.7 (s, 2H), 7.3–7.6 (m, 5H).

PREPARATION 7

N-[(2RS)-6-Benzyloxy-2,5,7,8-tetramethylchroman-2-ylmethyl]-(3R)-chloropiperidine

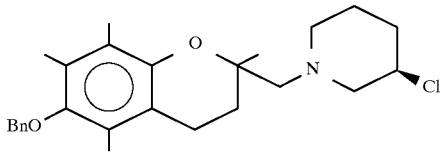

Thionyl chloride (6 ml) was added dropwise to a stirred, ice cooled solution of N-[(2RS)-6-benzyloxy-2,5,7,8-tetramethylchroman-2-ylmethyl]-(2S)-pyrrolidine-2-methanol (17 g) obtained in preparation 1, in dry benzene (200 ml). The resulting mixture was stirred at room temperature for 1 h and then diluted with ethyl acetate, washed with saturated aqueous sodium bicarbonate solution, water, brine and dried ($Na_2SO_4$). The organic layer was evaporated and the residue was chromatographed on silica gel using 12% ethyl acetate in petroleum ether as eluent to give 13 g (73%) of the title compound as a thick liquid.

$^1$H NMR ($CDCl_3$, 200 MHz): δ1.24 (s, 3H), 1.4–2.5 (m, 8H), 2.1 (s, 3H), 2.18 (s, 3H), 2.23 (s, 3H), 2.53 (s, 2H), 2.63 (t, J=6.8 Hz, 2H), 2.8 (m, 1H), 3.3 (m, 1H), 4.0 (m, 1H), 4.7 (s, 2H), 7.3–7.6 (m, 5H).

PREPARATION 8

N-[(3RS)-5-Benzyloxy-2,3-dihydro-2,2,4,6,7-pentamethylbenzofuran-3-ylmethyl]-(3R)-chloropiperidine

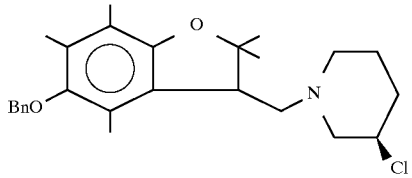

The title compound (0.85 g, 90%) was prepared as a pale yellow solid from the product (0.9 g) obtained in preparation 2 and thionylchloride (0.79 ml) by a similar procedure to that used in preparation 7.

$^1$H NMR ($CDCl_3$, 200 MHz): δ1.35 (s, 3H), 1.62 (bs, 5H), 1.80 (m, 2H), 2.11 (s, 3H), 2.23 (s, 6H), 2.30 (m, 2H), 2.53 (m, 2H), 2.86 (m, 1H), 3.06 (m, 1H), 3.22 (m, 1H), 4.0 (m, 1H), 4.71 (s, 2H), 7.43 (m, 5H).

PREPARATION 9

[N-(5-Benzyloxy-2,4,6,7-tetramethylbenzofuran-3-ylmethyl)-(3R)-chloropiperidine

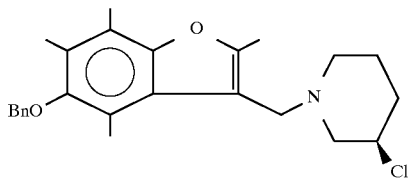

The title compound (2 g, 63%) was prepared as a white solid from N-(5-benzyloxy-2,4,6,7-tetramethylbenzofuran-3-ylmethyl)-(2S)-pyrrolidine-2-methanol (3.0 g) obtained in preparation 3 and thionylchloride (2.78 ml) by a similar procedure to that used in preparation 7. mp 90°–92° C.

$[\alpha]_D^{20}$=−49.7 (c, 1.0, $CHCl_3$)

$^1$H NMR ($CDCl_3$, 200 MHz): δ1.68 (m, 3H), 2.19 (m, 3H), 2.36 (s, 3H), 2.45 (s, 6H), 2.62 (s, 3H), 2.78 (m, 1H), 3.13 (m, 1H), 3,51 (d, J=6.2 Hz, 2H), 3.92 (m, 1H), 4.72 (s, 2H), 7.47 (m, 5H).

PREPARATION 10

N-(5-benzyloxy-2-methylbenzofuran-3-ylmethyl)-(3R)-chloropiperidine

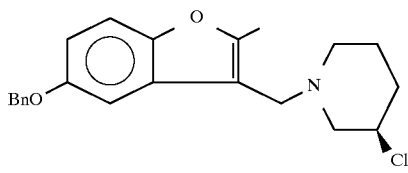

The title compound (2.3 g, 100%) was prepared as an oil from N-(5-benzyloxy-2-methylbenzofuran-3-ylmethyl)-(2S)-pyrrolidine-2-methanol (2.25 g) obtained in preparation 4 and thionylchloride (2.34 ml) by a similar procedure to that used in preparation 7.

$[\alpha]_D^{25}$=−20.6 (c, 1.83, $CHCl_3$)

$^1$H NMR (CDCl$_3$, 200 MHz): δ1.62 (m, 3H), 2.20 (m, 3H), 2.39 (s, 3H), 2.68 (m, 1H), 3.05 (m, 1H), 3.54 (s, 2H), 3.89 (m, 1H), 5.11 (s, 2H), 6.68 (m, 1H), 7.42 (m, 7H).

PREPARATION 11

N-(1-Methylindol-3-ylmethyl)-(2S)-pyrrolidine-2-methyl methanesulfonate

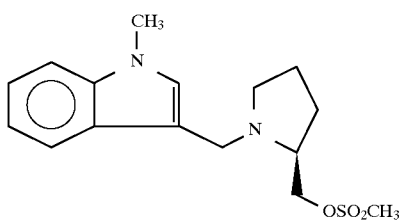

To an ice cooled solution of the product (0.5 g) obtained in preparation 5 and triethylamine (0.85 ml) in CH$_2$Cl$_2$ (10 ml) was added methanesulfonyl chloride (0.2 ml). The mixture was stirred at 5° C. for 2 h. At the end of this time, the reaction mixture was washed with aqueous NaHCO$_3$ solution followed by H$_2$O, dried (CaCl$_2$) and concentrated to get 0.65 g (98%) of the title compound. The crude product was used in the next step without further purification.

PREPARATION 12

2-[4-[(2RS)-6-Benzyloxy-2,5,7,8-tetramethylchroman-2-ylmethyl]piperazine-1-yl] ethanol

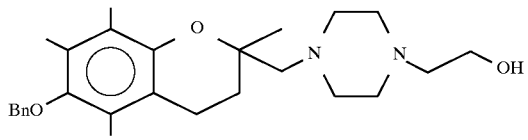

To a mixture of 1-[(2RS)-6-benzyloxy-2,5,7,8-tetramethylchroman-2-ylmethyl]piperazine (2.3 g) obtained in preparation 6 and 2-bromoethanol (0.62 ml) in dry DMSO (15 ml), K$_2$CO$_3$ (2.4 g) was added and the mixture was stirred at room temperature for 12 h. At the end of this time, the reaction mixture was cooled, added water and extracted with EtOAc. The EtOAc extract was washed with water followed by brine and dried over anhydrous sodium sulphate. The solvent was then removed by distillation under reduced pressure and the resulting crude compound was chromatographed on silica gel using 1% methanol in chloroform to afford (0.7 g, 27%) the pure compound as a thick liquid.

$^1$H NMR (CDCl$_3$, 200 MHz): δ1.24 (s, 3H), 1.7 (m, 1H), 2.0 (m, 1H), 2.07 (s, 31), 2.18 (s, 3H), 2.22 (s, 3H), 2.5–3.0 (m, 14H), 3.68 (t, J=5.2 Hz, 2H), 4.7 (s, 2H), 7.3–7.6 (m, 5H).

PREPARATION 13

2-[4-[(2RS)-6-Benzyloxy-2,5,7,8-tetramethylchroman-2-ylmethyl]piperazine-1-yl] ethyl chloride

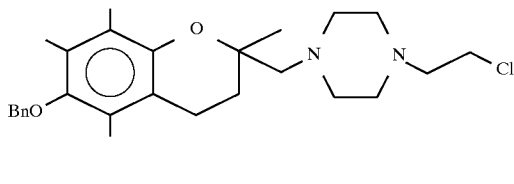

The title compound (0.2 g, 33%) was prepared as a thick liquid from the product (0.6 g) obtained in preparation 12 and thionyl chloride (0.2 ml) by a similar procedure to that used in preparation 7.

$^1$H NMR (CDCl$_3$, 200 MHz): δ 1.24 (s, 3H), 1.7 (m, 1H), 2.0 (m, 1H), 2.07 (s, 3H), 2.17 (s, 3H), 2.22 (s, 3H), 2.4–2.8 (m, 14H), 3.6 (t, J=7 Hz), 4.7 (s, 2H), 7.3–7.6 (m, 5H).

PREPARATION 14 a) 4-[N-[(2RS)-6-Benzyloxy-2,5,7,8-tetramethylchroman-2-ylmethyl]-(2S)-pyrrolidine-2-methoxy]benzaldehyde (14a)

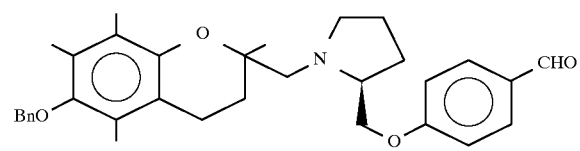

and b) 4-[N-[(2RS)-6-Benzyloxy-2,5,7,8-tetramethylchroman-2-ylmethyl]-(3R)-piperidinyloxy]benzaldehyde (14b)

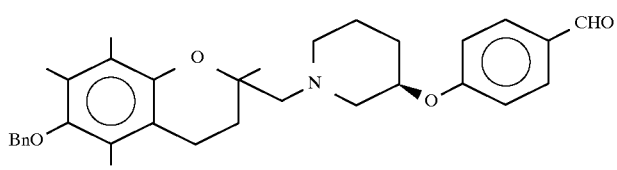

Method A

To a mixture of N-[(2RS)-6-benzyloxy-2,5,7,8-tetramethylchroman-2-ylmethyl]-(3R)-chloropiperidine (5 g) obtained in preparation 7 and 4-hydroxybenzaldehyde (1.7 g) in dry DMF, K$_2$CO$_3$ (6.4 g) was added and the mixture was stirred at 80° C. for 2 h. At the end of this time, the mixture was cooled, water added and extracted with EtOAc. The EtOAc extract was washed with 5% aqueous Na$_2$CO$_3$ solution, followed by brine and dried over anhydrous sodium sulphate. The solvent was then removed by distillation under reduced pressure to give 4.2 g (70%) of the crude product as a mixture of 14a and 14b (1:1), which was separated by column chromatography on silica gel using 2 to 10% (gradient elution) ethyl acetate in petroleum ether to afford 14a (2.0 g, 33%, as a syrupy liquid) and 14b (2.1 g, 35% as semi solid).

Method B

To a mixture of N-[(2RS)-6-benzyloxy-2,5,7,8-tetramethylchroman-2-ylmethyl]-(2S)-pyrrolidine-2-methanol (16 g) obtained in preparation 1,4-hydroxybenzaldehyde (5.2 g) and triphenyl phosphine (11.8 g) in THF (200 ml), diisopropyl azodicarboxylate (15 ml) was added and the mixture was stirred at room temperature (30° C.) for 1 h. At the end of this time, it was diluted with EtOAc, washed with water, dried (Na$_2$SO$_4$) and concentrated under reduced pressure to give a mixture of 14a and 14b (1.1:1.0) which was separated by column chromatography using 2 to 10% (gradient elution) ethyl acetate in petroleum ether to give 14a (8.2 g, 41%, as a syrupy liquid) and 14b (8 g, 40%, as a semi solid).

14a: $^1$H NMR (CDCl$_3$, 200 MHz): δ1.2 (s, 3H), 1.5–2.05 (m, 6H), 2.09–2.3 (6s, 9H), 2.35–3.2 (m, 6H), 3.4 (m, 1H), 3.8 (m, 1H), 4.05 (m, 1H), 4.7 (s, 2H), 7.0 (m, 2H), 7.3–7.6 (m, 5H), 7.75 (m, 2H), 9.9 (s, 1H).

14b: $^1$H NMR (CDCl$_3$, 200 MHz): δ1.2, (s, 3H), 1.3–2.7 (m, 12H), 1.9 (s, 3H), 2.09 (s, 3H), 2.12 (s, 3H), 2.8 (m, 1H), 3.25 (m, 1H), 4.4 (m, 1H), 4.62 (s, 2H), 6.9 (m, 2H), 7.2–7.6 (m, 5H), 7.78 (m, 2H), 9.8 (s, 1H).

PREPARATION 15 a) 3-[N-[(2RS)-6-Benzyloy-2,5,7,8-tetramethylchroman-2-ylmethyl]-(2S)-pyrrolidine-2-methoxy]benzaldehyde (15)

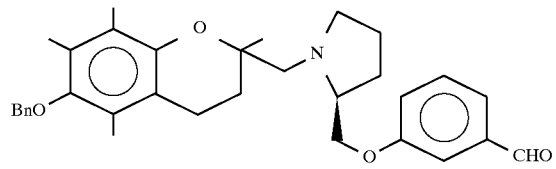

The title compound 15 (1.5 g, 35%) was prepared as a thick liquid from N-[(2RS)-6-benzyloxy-2,5,7,8-tetramethylchroman-2-ylmethyl)-(3R)-chloropiperidine (3.5 g), obtained in preparation 7 and 3-hydroxybenzaldehyde (1.2 g) in a similar manner to that described in Method A of preparation 13. The crude compound was chromatographed on silica gel to get 15.

$^1$H NMR (CDCl$_3$, 200 MHz): δ 1.21, 1.28 (2s, 3H), 1.50–2.05 (m, 6H), 2.11–2.23 (m, 9H), 2.35–3.25 (m, 6H), 3.40 (m, 1H), 3.85 (m, 1H), 4.05 (m, 1H), 4.70 (m, 2H), 7.10–7.60 (m, 9H), 9.97, 9.99 (2s, 1H).

PREPARATION 16

4-[N-[(3R/S)-5-Benzyloxy-2,3-dihydro-2,2,4,6,7-pentamethylbenzofuran-3-ylmethyl]-(2S)-pyrrolidine-2-methoxy]benzaldehyde (16)

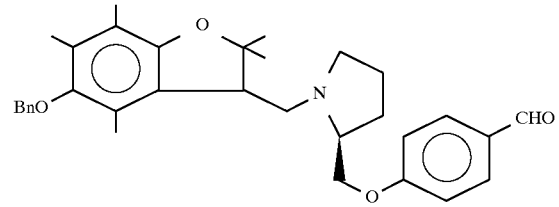

The title compound (1.6, 5g, 22%) was prepared as an oil from N-[(3R/S)-5-benzyloxy-2,3-dihydro-2,2,4,6,7-pentamethyl-benzofuran-3ylmethyl]-(3R)-chloropiperidine (6.4 g) obtained in preparation 8 and 4-hydroxybenzaldehyde (1.83 g) in a similar manner to that described in, method A of preparation 14. The crude compound was chromatographed on silica gel to get 16.

$^1$H NMR (CDCl$_3$, 200 MHz): δ 1.35 (s, 3H), 1.64 (s, 3H), 1.80 (m, 4H), 2.12 (s, 3H), 2.21 (s, 3H), 2.30 (s, 3H), 2.45 (m, 2H), 2.78 (m, 1H), 3.15 (m, 2H), 3.35 (m, 1H), 3.89 (m, 1H), 4.08 (m, 1H), 4.75 (s, 2H), 6.96 (d, J=10.4 Hz, 2H), 7.44 (m, 5H), 7.85 (d, J=10.4 Hz, 2H), 9.94 (s, 1H).

PREPARATION 17

3-[N-((3R/S)-5-Benzyloxy-2,3-dihydro-2,2,4,6,7-pentamethylbenzofuran-3-ylmethyl]-(2S)-pyrrolidine-2-methoxy]benzaldehyde

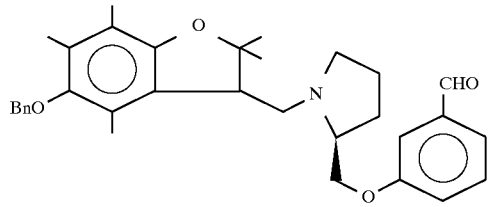

The title compound (0.8 g, 11%) was prepared as an oil from N-[(R/S)-5-benzyloxy-2,3-dihydro-2,2,4,6,7-pentamethylbenzofuran-3-ylmethyl]-(3R)-chloropiperidine (6.0 g) obtained in preparation 8 and 3-hydroxybenzaldehyde (1.71 g) in a similar manner to that described in method A of preparation 14. The crude compound was chromatographed on silica gel to get 17.

$[α]_D^{21}$=−81.7 (c, 1.24, CHCl$_3$)

$^1$H NMR (CDCl$_3$, 200 MHz): δ 1.34 (s, 3H), 1.60 (s, 3H), 1.83 (m, 4H), 2.09 (s, 3H), 2.19 (8, 3H), 2.27 (s, 3H), 2.32 (m, 2H), 2.78 (m, 1H), 3.19 (m, 2H), 3.35 (m, 1H), 3.85 (dd, J=9.0 and 6.0 Hz, 1H), 4.04 (dd, J=9.0 and 5.0 Hz, 1H), 4.72 (s, 2H), 7.17 (m, 1H), 7.48 (m, 8H), 9.97 (s, 1H).

PREPARATION 18 a) 4-[N-(5-Benzyloy-2,4,6,7-tetramethylbenzofuran-3-ylmethyl)-(2S)-pyrrolidine-2-methoxy]]benzaldehyde (18a)

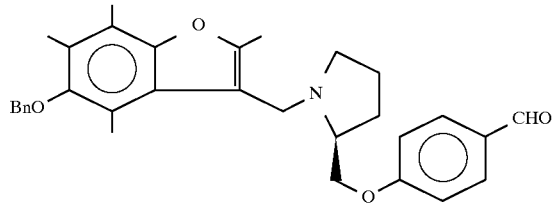

b) 4-[N-[5-Benzyloxy-2,4,6,7-tetramethylbenzofuran-3-ylmethyl]-(3R)-piperidinyloxy]benzaldehyde (18b)

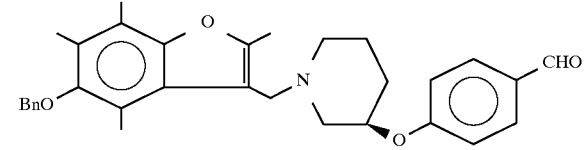

The title compounds 18a and 18b were prepared from N-(5-benzyloxy-2,4,6,7-tetramethylbenzofuran-3-ylmethyl)-(3R)-chloropiperidine (3 g) obtained in preparation 9 and 4-hydroxybenzaldehyde (0.889 g) in a similar manner to that described in method A of preparation 14. The crude compound was chromatographed on silica gel to get 18a (1.0 g, 27%) as an oil and 18b (0.89 g, 22%) as a white solid, mp: 142°–144° C.

18a: $[\alpha]_D^{22}$=+51.0 (c, 1.0, $CH_2Cl_2$)

$^1$H NMR ($CDCl_3$, 200 MHz): δ 1.80 (m, 4H), 2.08 (m, 1H), 2.30 (s, 3H), 2.37 (s, 3H), 2.42 (s, 3H), 2.59 (s, 3H), 3.03 (m, 2H), 3.59 (d, J=12.9 Hz, 1H), 3.79 (dd, J=9.6 Hz and 6.8 Hz, 1H), 3.93 (dd, J=9.6 Hz and 5.2 Hz, 1H), 4.05 (d, J =12.9 Hz, 1H), 4.70 (s, 2H), 6.80 (d, J=8.6 Hz, 2H), 7.48 (m, 5H), 7.77 (d, J=6.6 Hz, 2H), 9.86 (s, 1H).

18b: $[\alpha]_D^{23}$=−57.5 (c, 0.2, $CH_2Cl_2$)

$^1$H NMR ($CDCl_3$, 200 MHz): δ 1.74 (m, 4H), 2.18 (m, 2H), 2.29 (s, 3H), 2.32 (s, 6H), 2.62, (s, 3H), 2.73 (m, 1H), 3.05 (m, 1H), 3.45 (d, J=5.4 Hhhz, 2H), 4.40 (m, 1H), 4.77 (s, 2H), 6.91 (d, J=8.6 Hz, 2H), 7.49 (m, 5H), 7.75 (d, J=8.7 Hz, 2H), 9.84 (s, 1H).

(d, J=4.1 Hz, 2H), 6.86 (m, 1H), 6.96 (d, J=8.5 Hz, 2H), 7.36 (m, 7H), 7.77 (d, J=8.6 Hz, 2H), 9.81 (s, 1H).

PREPARATION 20

4-[N-[1-Methylindol-3-ylmethyl]-(2S)-pyrrolidine-2-methoxy]benzaldehyde

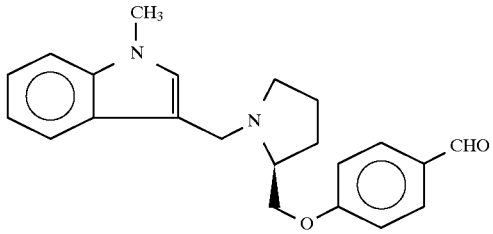

The title compound (0.16 g, 29%) was prepared as a viscous oil from N-[1-methylindol-3-ylmethyl]-(2S)-pyrrolidine-2-methyl methanesulfonate (0.5 g), obtained in preparation 11 and 4-hydroxybenzaldehyde (0.2 g), in a similar manner to that described in method A of preparation 14.

$[\alpha]_D^{22}$=−30.65 (c, 1.65, $CHCl_3$).

$^1$H NMR ($CDCl_3$, 200 MHz): δ 1.5 (m, 4H), 3.04 (m, 1H), 3.76 (m, 3H), 3.84 (s, 3H), 4.22 (m, 1H), 4.56 (m, 2H), 7.02 (d, J=7.8 Hz, 2H), 7.34 (m, 4H) 7.66 (d, J =7.8 Hz, 1H), 7.88 (m, 2H), 9.94 (s, 1H)

PREPARATION 21

4-[2-[4-[(2RS)-6-Benzyloxy-2,5,7,8-tetramethylchroman-2-ylmethyl)piperazine-1-yl]ethoxy]benzaldehyde

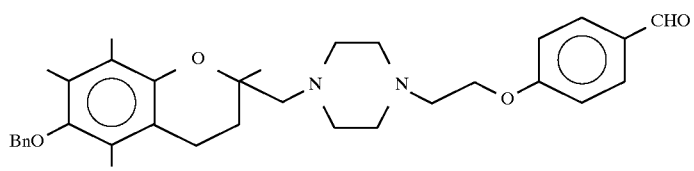

PREPARATION 19

4-[N-[5-Benzyloxy- 2-methylbenzofuran-3-ylmethyll-(2S)-pyrrolidine-2-methoxy]benzaldehyde (19 )

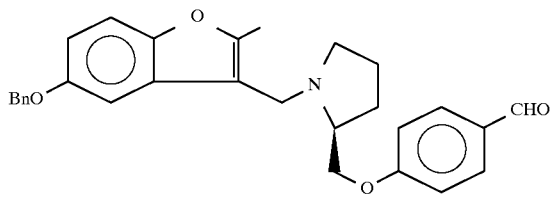

The title compound (0.25 g, 41%) was prepared as an oil from N-(5-benzyloxy-2 methylbenzofuran-3-ylmethyl)-(3R)-chloropiperidine (0.5 g) obtained in preparation 10 and 4-hydroxybenzaldehyde (0.247 g) in a similar manner to that described in method A of preparation 14. The crude compound was chromatographed on silica gel to get 19.

$[\alpha]_D^{25}$=−6.9 (c, 0.28, $CHCl_3$)

$^1$H NMR ($CDCl_3$, 200 MHz): δ 1.73 (m, 3H), 2.04 (m, 1H), 2.32 (m, 1H), 2.41 (s, 3H), 2.99 (m, 2H), 3.60 (d, J=13.3 Hz, 1H), 4.02 (m, 2H), 4.12 (d, J=13.3 Hz, 1H), 4.90

The title compound (0.2 g, 84%) was prepared as a thick liquid from 2-[4-[(2RS)-6-benzyloxy-2,5,7,8-tetramethylchroman-2-ylmethyl)piperazin-1-yl]ethyl chloride (0.2 g), obtained in preparation 13 and 4-hydroxybenzaldehyde (0.06 g) in a similar manner to that described in method A of preparation 14.

$^1$H NMR ($CDCl_3$, 200 MHz): δ1.25 (s, 3H), 1.7 (m, 1H), 2.0 (m, 1H), 2.07 (s, 3H), 2.18 (s, 3H), 2.22 (s, 3H), 2.4–2.8 (m, 12H), 2.86 (t, J=5.8 Hz, 2H), 4.2 (t, J=5.8 Hz, 2H), 4.7 (s, 2H), 7.0 (d, J=8.4 Hz, 2H), 7.3–7.6 (m, 5H), 7.83 (d, J=8.4 Hz, 2H), 9.9 (s, 1H).

PREPARATION 22

4-[2-[4-(1-Methylindol-3-ylmethyl)piperazin-1-yl]ethoxy]benzaldehyde

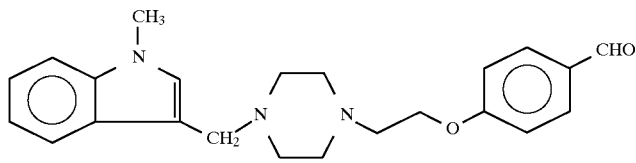

A suspension of 1-(1-methylindole-3-ylmethyl)piperazine (1.3 g) in dimethylsulfoxide (15 ml) and potassium hydroxide (0.63 g) was stirred for 30 min under nitrogen at 22° C. and then a solution of 4-[2-bromoethoxy]benzaldehyde (1.3 g) was added and stirring was continued for further 4 h. The reaction mixture was diluted with water and extracted with ethyl acetate and the organic layer was washed with water, brine, dried (Na$_2$SO$_4$) and solvent was evaporated under reduced pressure. The crude product was chromatographed on silica gel using mixture of methanol: chloroform (1:9) as eluent to afford the pure product (0.76 g, 51%) as an oil.

$^1$H NMR (CDCl$_3$, 200 MHz): δ 2.61 (bs, 8H), 2.83 (t, J=5.72 Hz, 2H), 3.73 (s, 2H), 3.76 (s, 3H), 4.16 (t, J=5.72 Hz, 2H), 6.98 (d, J=8.5 Hz, 2H), 7.28 (m, 4H), 7.70 (d, J=7.9 Hz, 1H), 7.81 (d, J=8.5 Hz, 2H), 9.87 (s, 1H).

PREPARATION 23

4-[N-(3,5-Dimethyl-4-methoxy-2-pyridyl methyl]-(2S)-pyrrolidine-2-methoxy]benzaldehyde

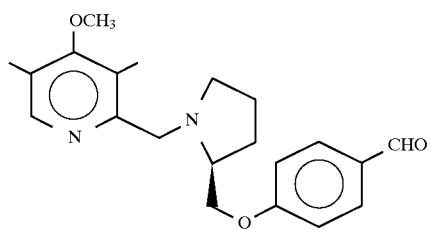

A solution of N-[(3,5-dimethyl-4-methoxy-2-pyridyl methyl]-(2S)-pyrrolidine-2-methanol (2.5 g) in 5 ml of dimethyl formamide (5 ml) was added dropwise while cooling to a suspension of (60% w/w dispersion) sodium hydride (0.48 g) in dimethyl formamide (20 ml). The mixture was then stirred for 1 h at room temperature, after which 4-fluorobenzaldehyde (1.3 ml) in dimethyl formamide (5 ml) was added dropwise at room temperature. The reaction mixture was then stirred at 70° C. for 12 h. At the end of this time, water was added to the reaction mixture and extracted with EtOAc, dried and concentrated under reduced pressure to get 1.8 g (51%) of the title compound. The crude product was used in the next step without further purification.

PREPARATION 24

4-[N-[(2RS)-6-Benzyloxy-2,5,7,8-tetramethylchroman-2-ylmethyl]-(2S)-pyrrolidine-2-methoxy]nitrobenzene

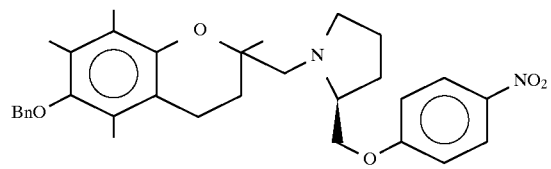

A solution of 16 g of the product obtained in preparation 1 in dimethyl formamide (100 ml) was added dropwise to a suspension of (50% w/w dispersion) sodium hydride (2.81 g) in dimethyl formamide (50 ml). The mixture was then stirred at room temperature for 0.5 h, after which 1-fluoro-4-nitrobenzene (6.6 g) was added dropwise and the mixture was then stirred at the same temperature for 2 h. At the end of this time, water was added and the mixture was extracted with ethyl acetate, dried (Na$_2$SO$_4$), and the solvent was removed by distillation under reduced pressure to give 20 g of the crude compound which was chromatographed on silica gel using 10 to 20% (gradient elution) of ethyl acetate in petroleum ether to afford 16.8 g (81%) of the title compound as a thick liquid.

$^1$H NMR (CDCl$_3$, 200 MHz): δ 1.25 (m, 3H), 1.55–3.2 (complex, 21H), 3.4 (m, 1H), 3.85 (m, 1H), 4.1 (m, 1H), 4.7 (s, 2H), 6.9 (m, 2H), 7.3–7.6 (m, 5H), 8.2 (m, 2H).

PREPARATION 25

4-[N-((3RS)-5-Benzyloy-2,3-dihydro-2,2,4,6,7-pentamethylbenzofuran-3-ylmethyl)-(2S)-pyrrolidine-2-methoxy]nitrobenzene

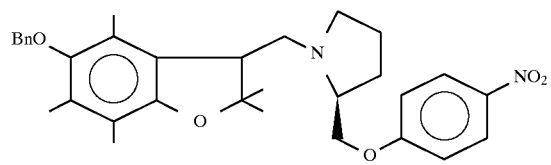

The title compound (7.25 g, 67%) was prepared as an oil from N-[(3RS)-5-benzyloxy-2,3-dihydro-2,2,4,6,7-pentamethylbenzofuran-3-ylmethyl]-(2S)-pyrrolidine-2-methanol (8.4 g) obtained in preparation 2 and 4-fluoronitrobenzene (2.6 ml) by a similar procedure to that used in preparation 24.

$^1$H NMR (CDCl$_3$, 200 MHz): δ 1.29 (s, 3H), 1.35 (s, 3H), 1.56 (s, 3H), 1.59 (s, 3H), 1.85 (m, 8H), 2.06 (s, 3H), 2.09

(s, 3H), 2.12 (s, 3H), 2.20 (s, 3H), 2.27 (s, 6H), 2.45 (m, 3H), 2.82 (m, 3H), 3.0 (m, 1H), 3.18 (m, 4H), 3.38 (m, 1H), 3.58 (m, 2H), 3.86 (m, 1H), 4.08 (m, 1H), 4.65 (d, J=7.8 Hz, 2H), 4.72 (s, 2H), 6.74 (d, J=8 Hz, 2H), 6.93 (d, J=9 Hz, 2H), 7.48 (m, 10H), 8.13 (d, J=9 Hz, 2H), 8.19 (d, J=9 Hz, 2H).

PREPARATION 26

4-[N-[5-Benzyloy-2,4,6,7-tetramethylbenzofuran-3-ylmethyl]-(2S)-pyrrolidine-2-methoxylnitrobenzene

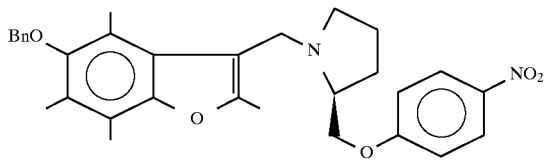

The title compound (25 g, 79%) was prepared as an yellow solid from N-[5-benzyloxy-2,4,6,7-tetramethylbenzofuran-3-ylmethyl]-(2S)-pyrrolidine-2-methanol (24 g) obtained in preparation 3 and 4-fluoronitrobenzene (11.19 g) by a similar procedure to that used in preparation 24. mp. 136°–139° C.

$^1$H NMR (CDCl$_3$, 200 MHz): δ 1.78 (m, 4H), 2.06 (m, 1H), 2.32 (s, 3H), 2.38 (8, 3H), 2.43 (s, 3H), 2.59 (s, 3H), 3.03 (m, 2H), 3.63 (d, J=12.8 Hz, 1H), 3.85 (m, 2H), 4.0 (d, J=12.8 Hz, 1H), 4.72 (s, 2H), 6.72 (d, J=9 Hz, 2H), 7.45 (m, 5H), 8.13 (d, J=9 Hz, 2H).

PREPARATION 27

4-[N-[(2RS)-6-Benzyloxy-2,5,7,8-tetramethylchroman-2ylmethyl]-(2S)-pyrrolidine-2-methoxy]aniline

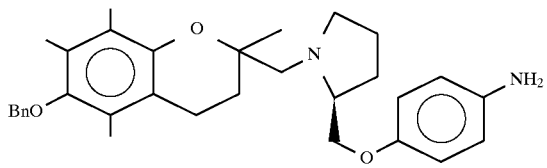

4-[N-[(2RS)-6-Benzyloxy-2,5,7,8-tetramethylchroman-2-ylmethyl]-(2S)-pyrrolidine-2-methoxy] nitrobenzene (5.8 g) obtained in preparation 24 was dissolved in EtOAc (30 ml) and was reduced with hydrogen (60 psi) in the presence of 10% palladium on charcoal (0.6 g) at ambient temperature until hydrogen uptake (nearly 6 h) ceased. The solution was filtered through a bed of celite, the filter pad was washed exhaustively with EtOAc. The combined filtrate was evaporated to dryness under reduced pressure. The crude product was chromatographed on silica gel using 2 to 10% (gradient elution) of methanol in chloroform to afford 5 g (91%) of the title compound as a thick liquid.

$^1$H NMR (CDCl$_3$, 200 MHz): δ 1.2, 1.3 (2s, 3H), 1.5–3.2 (complex, 12H), 2.1 (s, 3H), 2.15 (s, 3H), 2.2 (s, 3H), 3.4 (m, 1H), 3.75 (m, 1H), 3.9 (m, 1H), 4.7 (s, 2H), 6.7 (m, 4H), 7.4 (m, 5H).

PREPARATION 28

4-[N-[(3RS)-5-Benzyloy-2,3-dihydro-2,2,4,6,7-pentamethylbenzofuran-3-ylmethyl]-(2S)-pyrrolidine-2-methoxy]aniline

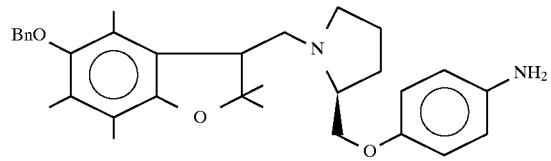

The title compound (5.1 g, 55%) was prepared as a brown oil from 4-[N-[(3RS)-5-benzyloxy-2,3-dihydro-2,2,4,6,7-pentamethylbenzofuran-3-ylmethyl]-(2S)-pyrrolidine-2-methoxy]nitrobenzene (9.8 g) obtained in preparation 25, by a similar procedure to that described in preparation 27.

$^1$H NMR (CDCl$_3$, 200 MHz): δ 1.31, 1.33 (2s, 3H), 1.56, 1.61 (2s, 3H), 1.84 (m, 4H), 2.10 (s, 3H), 2.22 (s, 3H), 2.28 (s, 3H), 2.45 (m, 2H), 2.79 (m, 1H), 3.12 (m, 2H), 3.35 (m, 1H), 3.75 (m, 1H), 3.98 (m, 1H), 4.75 (m, 2H), 6.68 (m, 4H), 7.46 (m, 5H).

PREPARATION 29

4-[N-[5-Benzyloxy-2,4,6,7-tetramethylbenzofuran-3-ylmethyl]-(2S)-pyrrolidine-2-methoxy]aniline

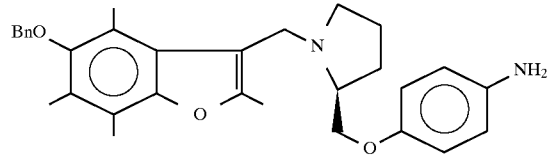

The title compound (3.3 g, 70%) was prepared as a thick liquid from 4-[N-[5-benzyloxy-2,4,6,7-tetramethylbenzofuran-3-ylmethyl]-(2S)-pyrrolidine-2-methoxy]nitrobenzene (5 g) obtained in preparation 26 by a similar procedure to that described in preparation 27.

$^1$H NMR (CDCl$_3$, 200 MHz): δ 1.61 (m, 41), 2.10 (m, 1H), 2.29 (s, 3H), 2.34 (s, 3H), 2.40 (s, 3H), 2.65 (s, 3H), 2.96 (m, 2H), 3.41 (bs, exchangeable with D$_2$O, 2H), 3.48 (d, J=13 Hz, 1H), 3.65 (m, 1H), 3.85 (m, 1H), 4.12 (d, J=13 Hz, 1H), 4.75 (s, 2H), 6.62 (s, 4H), 7.48 (m, 5H).

PREPARATION 30

Ethyl-2-bromo-3-[4-[N-[(2RS)-6-benzyloxy-2,5,7,8-tetramethylchroman-2ylmethyl]-(2S)-pyrrolidine-2-methoxy]phenyl]propanoate

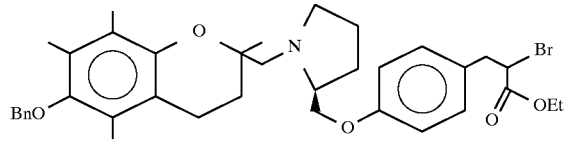

A solution of NaNO$_2$ (0.72 g) in H$_2$O (1.3 ml) was added dropwise to a stirred and ice cooled mixture of 4-[N-[(2RS)-6-benzyloxy-2,5,7,8-tetramethylchroman-2-ylmethyl]-(2S)-pyrrolidine-2-methoxy]aniline (4.8 g) obtained in preparation 27, aqueous HBr (48%, 6.5 ml) MeOH (8.8 ml) and acetone (21 ml) below 5° C. The solution was stirred at 5° C. for 30 min and ethyl acrylate (6 ml) was added and the temperature was raised to 38° C. Powdered $Cu_2O$ (77 mg) was added in small portions to the vigorously stirred mixture. After the $N_2$ gas evolution has ceased, the reaction mixture was concentrated in vacuo. The residue was diluted with water, made alkaline with concentrated $NH_4OH$ and extracted with EtOAc. The EtOAc extract was washed with brine, dried ($Na_2SO_4$) and concentrated in vacuum. The crude product was chromatographed on silica gel using 10–20% (gradient elution) of ethyl acetate in petroleum ether to afford 3.0 g (47%) of the title compound as a thick liquid.

$^1$H NMR (CDCl$_3$, 200 MHz): δ 1.2 (m, 6H), 1.55–3.5 (complex, 15H), 2.1 (s, 3H), 2.15 (s, 3H), 2.2 (s, 3H), 3.75 (m, 1H), 3.9 (m, 1H), 4.2 (m, 2H), 4.35 (m, 1H), 4.7 (s, 2H), 6.7 (m, 2H), 7.1 (m, 2H), 7.3–7.6 (m, 5H).

PREPARATION 31

Ethyl 2-bromo-3[4-[N-[(3RS)-5-benzyloxy-2,3-dihydro-2,2,4,6,7-pentamethyl benzofuran-3-ylmethyl]-(2S)-pyrrolidine-2-methoxy] phenyl] propanoate

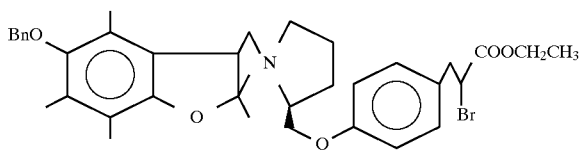

The title compound (2.5 g, 38%) was prepared as an oil from 4-[N-[(3RS)-5-benzyloxy-2,3-dihydro-2,2,4,6,7-pentamethylbenzofuran-3 -ylmethyl]-(2S)-pyrrolidine-2-methoxy]aniline (5 g), obtained in preparation 28, by a similar procedure to that described in preparation 30.

$^1$H NMR (CDCl$_3$, 200 MHz): δ 1.26 (m, 6H), 1.58, 1.60 (2s, 3H), 1.76 (m, 4H), 2.08 (s, 3H), 2.22 (s, 3H), 2.28 (s, 3H), 2.42 (m, 2H), 2.78 (m, 1H), 2.99 (m, 1H), 3.15 (m, 2H), 3.32 (m, 1H), 3.56 (m, 1H), 3.72 (m, 1H), 3.96 (m, 1H), 4.15 (q, J =6 Hz, 2H), 4.33 (m, 1H), 4.71 (m, 2H), 6.68 (d, J=8 Hz, 1H), 6.76 (d, J=8 Hz, 1H), 7.10 (m, 2H), 7.45 (m, 5H).

PREPARATION 32

Ethyl 2-bromo-3-[4-[N-[5-benzyloxy-2,4,6,7-tetramethylbenzofuran-3-ylmethyl]-(2S)-pyrrolidine-2-methoxy]phenyl]propanoate

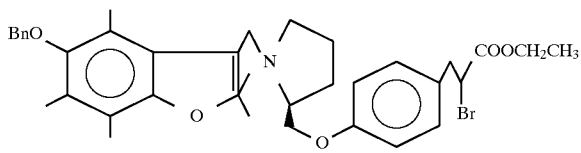

The title compound (2.8 g, 14%) was prepared as a viscous oil from 4-[N-[5-benzyloxy-2,2,4,6,7-tetramethyl] benzofuran-3-ylmethyl]-(2S)-pyrrolidine-2-methoxy] aniline (15 g), obtained in preparation 29, by a similar procedure to that described in preparation 30.

$^1$H NMR (CDCl$_3$, 200 MHz): δ 1.26 (t, J=7 Hz, 3H), 1.79 (m, 4H), 2.05 (m, 1H), 2.31 (s, 3H), 2.39 (s, 3H), 2.42 (s, 3H), 2.65 (s, 3H), 2.98 (m, 2H), 3.21 (m, 1H), 3.40 (m, 1H), 3.58 (d, J=12 Hz, 1H), 3.74 (m, 1H), 3.91 (m, 1H), 4.21 (m, 4H), 4.76 (s, 2H), 6.73 (d, J=7.7 Hz, 2H), 7.10 (d, J=7.7 Hz, 2H), 7.48 (m, 5H).

EXAMPLE 1

5-[4-[N-[(2RS)-6-Benzyloxy-2,5,7,8-tetramethylchroman-2-ylmethyl)]-(2S)-pyrrolidine-2-methoxy]phenyl methylene]thiazolidine-2,4-dione

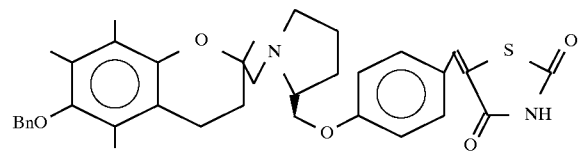

A solution of 4-[N-[(2RS)-6-benzyloxy-2,5,7,8-tetramethylchroman-2-ylmethyl]-(2S)-pyrrolidine-2-methoxy]benzaldehyde (1.2 g) obtained in preparation 14 and 2,4-thiazolidinedione (0.27 g) in toluene (30 ml) containing piperidine (30 mg) and benzoic acid (37 mg) was heated at reflux for 2 h using Dean-Stark apparatus. The reaction mixture was cooled, diluted with EtOAc and filtered, the filtrate was washed with $H_2O$, dried ($Na_2SO_4$) and evaporated under reduced pressure (1.4 g, 100%).

Preparation of polymorphs

Form 1

The product (0.5 g) obtained in example 1 was dissolved in 5 ml of EtOAc and the solution was heated at 80° C. At this temperature 2 ml of pet. ether was added dropwise and the resulting solution was filtered through a cotton plug and allowed to stay at 0° C. for 12 h. The resulting solid (220 mg, 44%) as pale yellow granules was filtered, washed with petroleum ether and dried under vacuum. mp 186.6° C.

$^1$H NMR (CDCl$_3$, 200 MHz): δ identical with that of Form 3.

Form 2

The compound (500 mg) obtained in example 1 was taken in a single neck RB flask equipped with $N_2$ and inlet was heated at 100° C. until the solid melts (5 min). Then the RB flask was immersed in an ice bath to get a deep yellow amorphous solid (500 mg, 100%) mp: 88° C.

$^1$H NMR (CDCl$_3$, 200 MHz): δ identical with that of Form 3.

Form 3

The crude product obtained above was chromatographed on silica gel using 0 to 0.5% (gradient elution) of methanol in chloroform to afford 1.3 g (93%) of the title compound as a pale yellow fluffy solid. mp. 86° C.

$[\alpha]_D^{24}$=−17.3 (c, 1.0, CDCl$_3$)

$^1$H NMR (CDCl$_3$, 200 MHz): δ 1.21, 1.26 (2s, 3H), 1.5–2.05 (m, 6H), 2.08–2.22 (6s, 9H), 2.35–3.15 (m, 6H), 3.4 (m, 1H), 3.8 (m, 1H), 4.0 (m, 1H), 4.7 (s, 2H), 6.95 (m, 2H), 7.3–7.6 (m, 7H), 7.8 (s, 1H).

EXAMPLE 2

5-[4-[N-[(2RS)-6-Benzyloxy-2,5,7,8-tetramethylchroman-2-ylmethyl)]-(2S)-pyrrolidine-2-methoxy]phenyl methylene]thiazolidine-2,4-dione, maleate

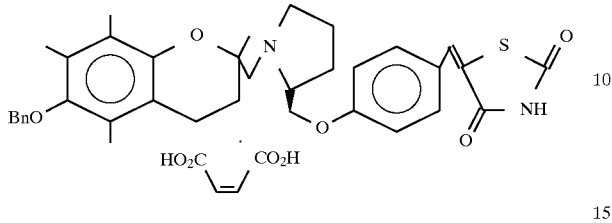

To a solution of 5-[4-[N-[(2RS)-6-benzyloxy-2,5,7,8-tetramethylchroman-2-ylmethyl)]-(2S)-pyrrolidine-2-methoxy]phenyl methylene]thiazolidine-2,4-dione (250 mg), obtained in example 1, in dry Et$_2$O (5 ml) at room temperature, maleic acid (47 mg) in Et$_2$O (5 ml) was added. The reaction mixture was stirred for an additional 30 min. and the Et$_2$O layer was decanted. The resulting solid was washed twice with Et$_2$O (2×5 ml) and dried under reduced pressure over P$_2$O$_5$ for 6 h to get a pale yellow solid (220 mg, 74%). mp: 210° C.

$[\alpha]_D^{27} = 27.0$ (c, 1.0, CHCl$_3$)

$^1$H NMR (CDCl$_3$, 200 MHz): δ 1.25, 1.3 (2s, 3H), 1.95, 2.0,2.1 (3s, 9H), 1.5–4.5 (complex m, 15H), 4.65 (2s, 2H), 6.1 (s, 2H), 7.0–7.7 (m, 9H), 7.8 (s, 1H).

EXAMPLE 3

5-[4-[N-[(2RS)-6-Benzyloxy-2,5,7,8-tetramethylchroman-2-ylmethyl]-(2S)-pyrrolidine-2-methoxy]phenyl methylene]thiazolidine-2,4-dione, sodium salt

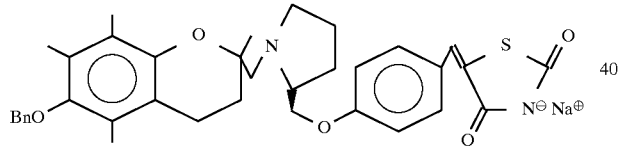

To a solution of 5-[4-[N-[(2RS)-6-benzyloxy-2,5,7,8-tetramethylchroman-2-ylmethyl]-(2S)-pyrrolidine-2-methoxy]phenyl methylene]thiazolidine-2,4-dione (250 mg), obtained in example 1, in dry Et$_2$O (15 ml) at room temperature, NaOMe in MeOH [prepared in situ by dissolving Na (13 mg) in MeOH (1 ml)] was added. The reaction mixture was stirred at room temperature for 30 min and the supernatant solvent was decanted. The resulting solid was washed twice with Et$_2$O (2×5 ml) and dried over P$_2$O$_5$ under reduced pressure for 6 h to get a pale yellow solid (235 mg, 65%), mp: 245° C.

$[\alpha]_D^{27} = -9.3$ (c, 0.82, CHCl$_3$).

$^1$H NMR (CDCl$_3$, 200 MHz): δ 1.15, 1.2 (2s, 3H), 2.05, 2.1, 2.15 (3s, 9H), 1.5 –3.6 (complex m, 13H), 3.8 (m, 1H), 4.0 (m, 1H), 4.6 (s, 2H), 7.0 (m, 2H), 7.5 (m, 8H).

EXAMPLE 4

5-[4-[N-[(2RS)-6-Benzyloxy-2,5,7,8-tetramethylchroman-2-ylmethyl]-(2S)-pyrrolidine-2-methoxy]phenyl methylene]thiazolidine-2,4-dione, hydrochloride

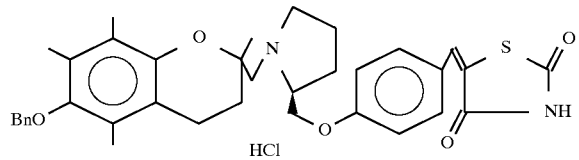

To a solution of 5-[4-[N-[(2RS)-6-benzyloxy-2,5,7,8-tetramethylchroman-2-ylmethyl]-(2S)-pyrrolidine-2-methoxy]phenyl methylene]thiazolidine-2,4-dione (300 mg) obtained in example 1 in Et$_2$O (15 ml) at 0° C., HCl gas was bubbled for 30 min. The resulting solution was stirred for an additional 30 min; the supernatant liquid was decanted and the resulting solid was washed with Et$_2$O (2×5 ml) and dried under reduced pressure over P$_2$O$_5$ for 6 h to get a pale yellow solid (200 mg, 75%). mp. 212°–214° C.

$[\alpha]_D^{27} = -25.5$ (c, 0.4, CHCl$_3$).

$^1$H NMR (DMSO-d$_6$, 200 MHz): δ 1.25,1.35 (2s, 3H), 1.99, 2.03, 2.12 (3s, 9H), 1.05–4.6 (complex m, 15H), 4.6,4.62 (2s, 2H), 7.0–7.7 (m, 9H), 7.8 (s, 1H), 9.6 (bs, 1H, exchangeable with D$_2$O).

EXAMPLE 5

5-[4-[N-[(2RS)-6-Benzyloxy-2,5,7,8-tetramethylchroman-2-ylmethyl]-(2S)-pyrrolidine-2-methoxy]phenyl methyl]thiazolidine-2,4-dione

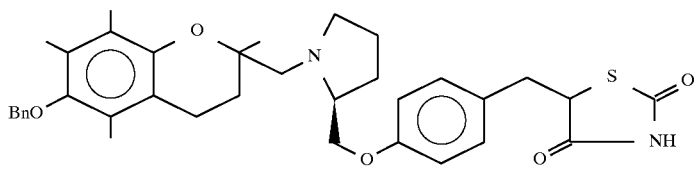

Method A

To a stirred suspension of the product obtained in example 1 (0.5 g) in methanol (20 ml) at room temperature was added magnesium turnings (0.36 g) and the reaction mixture was stirred at the same temperature for 1.5 h. The reaction mixture was added to ice water (10 ml), the pH was adjusted to 6.5–7.0 using 10% aqueous hydrochloric acid and the solution was extracted with chloroform (3×25 ml). The combined organic extract was washed with H$_2$O, dried (CaCl$_2$) and the solvent was removed under reduced pressure. The residual mass was chromatographed on silica gel using 0.5% methanol in chloroform to give 0.46 g (92%) of the title compound, mp: 62°–64° C.

Method B

A mixture of ethyl 2-bromo-3-[4-[N-[(2RS)-6-benzyloxy-2,5,7,8-tetramethylchroman-2-ylmethyl]-(2S)-pyrrolidine-2-methoxy]phenyl]propanoate (7 g), obtained in preparation 29, thiourea (1.6 g), NaOAc (1.73 g) and EtOH (42 ml) was stirred under reflux for 5 h. The reaction mixture was cooled and extracted with EtOAc, dried (Na$_2$SO$_4$) and concentrated to get 2-imino-5-[4-[N-[(2RS)-6-benzyloxy-2,5,7,8-tetramethylchroman-2-ylmethyl]-(2S)-pyrrolidine-2-methoxy]benzyl]-4-thiazolidinone which was used in the next step without further purification.

A mixture of the above crude product, 2N HCl (60 ml) and EtOH (60 ml) was stirred under reflux for 12 h. The reaction mixture was concentrated in vacuo. The residue was diluted with water, neutralized with saturated aqueous NaHCO$_3$ and extracted with ethyl acetate. The EtOAc extract was washed with brine, dried (Na$_2$SO$_4$) and concentrated in vacuo. The residue was chromatographed on silica gel with 40% EtOAc in pet. ether as eluent to afford the title compound (5.5 g, 85%) as a fluffy solid, mp 62°–64° C.

$[\alpha]_D^{27}$=–26.4 (c, 1.0, CHCl$_3$).

The title compound (0.28 g, 94%) was prepared as a pale yellow solid from 5-[4-[N[(2RS)-6-benzyloxy-2,5,7,8-tetramethylchroman-2-ylmethyl]-(2S)-pyrrolidine-2-methoxy]phenyl methyl]thiazolidine-2,4-dione (0.25 g), obtained in example 5 by an analogous procedure to that described in example 2, mp: 180° C.

$[\alpha]_D^{27}$=19.4 (c, 0.66, CHCl$_3$).

$^1$H NMR (CDCl$_3$, 200 MHz): δ 1.2, 1.25 (2s, 3H), 2.0, 2.05, 2.1 (3s, 9H), 1.5–4.5 (complex m, 17H), 4.6 (s, 2H), 4.9 (m, 1H), 6.1 (s, 2H), 6.9 (m, 2H), 7.2 (m, 2H), 7.5 (m, 5H), 12.1 (bs, 1H, exchangeable with D$_2$O).

EXAMPLE 7

5-[4-[N-(2RS)-6-Benzyloxy-2,5,7,8,-tetramethylchroman-2-ylmethyl]-(2S)-pyrrolidine-2-methoxy]phenyl methyl]thiazolidine-2,4-dione, sodium salt

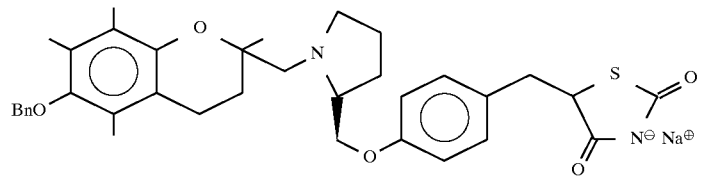

$^1$H NMR (CDCl$_3$, 200 MHz): δ 1.25 (m, 3H), 1.5–2.05 (m, 6H), 2.1–2.2 (m, 9H), 2.3–3.25 (m, 7H), 3.4 (m, 2H), 3.75 (m, 1H), 3.95 (m, 1H), 4.5 (m, 1H), 4.7 (s, 2H), 6.8 (m, 2H), 7.15 (m, 2H), 7.3–7.6 (m, 5H).

EXAMPLE 6

5 [4-[N-[(2RS)-6-Benzyloxy-2,5,7,8-tetramethylchroman-2-ylmethyl]-(2S)-pyrrolidine-2-methoxy]phenyl methyl]thiazolidine-2,4-dione, Maleate The title compound (0.27 g, 75%) was prepared as a white solid from 5-[4-[N-[(2RS)-6-benzyloxy-2,5,7,8-tetramethylchroman-2-ylmethyl]-(2S)-pyrrolidine-2-methoxy]phenyl methyl] thiazolidine-2,4-dione (0.35 g), obtained in example 5, by an analogous procedure to that described in example 3, mp: 191° C.

$[\alpha]_D^{27}$=–23.1 (c, 1.0, CHCl$_3$).

$^1$H NMR (CDCl$_3$, 200 MHz): δ 1.5, 1.25 (2s, 3H), 2.0 (s, 3H), 2.1 (s, 6H), 1.4–4.0 (complex m, 17H), 4.1 (m, 1H), 4.6 (s, 2H), 6.8 (m, 2H), 7.1 (m, 2H), 7.5 (m, 5H).

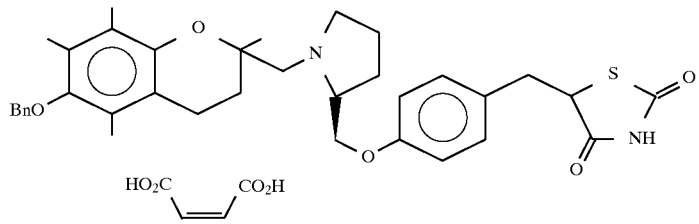

EXAMPLE 8

5-[4-[N-[(2RS)-6-Benzyloxy-2,5,7,8-tetramethylchroman-2-ylmethyl]-(2S)-pyrrolidine-2-methoxy]phenyl methyl]thiazolidine-2,4-dione, Hydrochloride

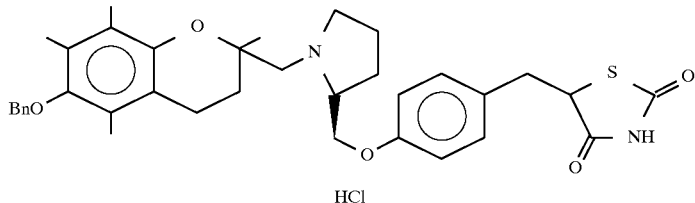

The title compound (0.18 g, 86%) was prepared as a pale yellow solid from 5-[4-[N-[(2RS)-6-benzyloxy-2,5,7,8-tetramethylchroman-2-ylmethyl]-(2S)-pyrrolidine-2-methoxy]phenyl methyl] thiazolidine-2,4-dione (0.2 g), obtained in example 5, by an analogous procedure to that described in example 4, mp: 230° C.

$[\alpha]_D^{27} = -9.5$ (c, 1.0, CHCl$_3$).

$^1$H NMR (CDCl$_3$, 200 MHz): δ 1.30, 1.4 (2s, 3H), 2.0, 2.05, 2.2 (3s, 9H), 1.5–4.5 (complex m, 17H), 4.6 (s, 2H), 4.9 (m, 1H), 6.9 (m, 2H), 7.2 (m, 2H), 7.5 (m, 5H), 9.8 (bs, 1H, exchangeable with D$_2$O), 12.1 (bs, 1H, exchangeable with D$_2$O).

EXAMPLE 9 a) 5-[3-[N-[(2RS)-6-Benzyloxy-2,5,7,8-tetramethylchroman-2-ylmethyl]-(2S)-pyrrolidine-2-methoxy]phenyl methylene]thiazolidine-2,4-dione (9a)

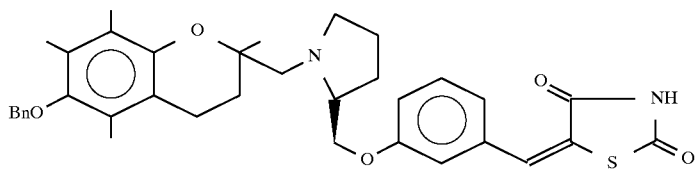

and b) 5-[3-[N-[(2RS)-6-Benzyloy-2,5,7,8-tetramethylchroman-2-ylmethyl]-(3R)-piperidinyloxy]phenyl methylene]thiazolidine-2,4-dione (9b)

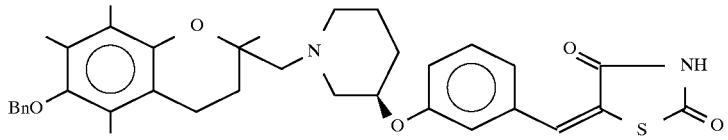

The title compounds 9a and 9b (4.5 g, 94%) were prepared from the crude mixture obtained in preparation 15, by a similar procedure to that described in example 1 and the crude product was separated by column chromatography on silica gel using 0.5% methanol in chloroform to afford 9a (1.5 g, 31%, gummy solid) and 9b (2.0 g, 42%, gummy solid).

9a: $^1$H NMR (CDCl$_3$, 200 MHz): δ 1.21,1.27 (2s, 3H), 1.5–2.05 (m, 6H), 2.05–2.2 (m, 9H), 2.3–3.2 (m, 6H), 3.4 (m, 1H), 3.8 (m, 1H), 4.05 (m, 1H), 4.7 (s, 2H), 7.0 (m, 4H), 7.25–7.6 (m, 5H), 7.77,7.81 (2s, 1H).

9b: $^1$H NMR (CDCl$_3$, 200 MHz): δ 1.21 (s, 3H), 1.3–2.8 (m, 12H), 1.91 (s, 3H), 2.16 (s, 6H), 3.1 (m, 1H), 3.55 (m, 1H), 4.4 (m, 1H), 4.7 (s, 2H), 6.85–7.55 (m, 9H), 7.78 (s, 1H).

EXAMPLE 10

5-[4-[N-(2RS)-6-Benzyloxy-2,5,7,8-tetramethylchroman-2-ylmethyl]-(3R)-piperidinyloxy] phenyl methylene]thiazolidine-2,4-dione

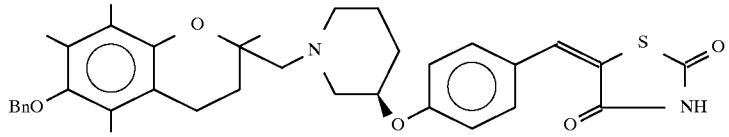

The title compound (1 g, 57%) was prepared as a pale yellow solid from 4-[N-[(2RS)-6-benzyloxy-2,5,7,8-tetramethylchroman-2-ylmethyl]-(3R)-piperidinyloxy] benzaldehyde (14b, 1.5 g), obtained in preparation 14 by a similar procedure to that described in example 1. mp: 142° C.

$^1$H NMR (CDCl$_3$, 200 MHz): δ 1.22 (s, 3H), 1.3–1.90 (m, 6H), 2.0 (s, 3H), 2.19 (s, 6H), 1.95–2.8 (m, 6H), 2.9 (m, 1H), 3.25 (m, 1H), 4.4 (m, 1H), 4.69 (s, 2H), 6.95 (m, 2H), 7.3–7.6 (m, 7H), 7.78 (s, 1H).

EXAMPLE 11

5-[4-[N-(5-Benzyloxy-2,3-dihydro-2,2,4,6,7-pentamethylbenzofuran-3-(R or S)-ylmethyl)-(2S)-pyrrolidine-2-methoxy]phenyl methylene] thiazolidine-2,4-dione

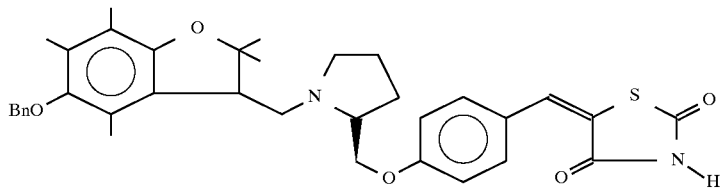

The title compound (0.8 g, 67%) was prepared as a pale yellow solid from 4-[N-[(3R/S)-5-benzyloxy-2,3-dihydro-2,2,4,6,7-pentamethylbenzofuran-3-ylmethyl)-(2S)-pyrrolidine-2-methoxy]benzaldehyde (1.0 g) obtained from preparation 16 by a similar procedure to that described in example 1, mp 68°–70° C.

[α]$_D^{24}$=−201.5 (c, 1.0, CHCl$_3$).

$^1$H NMR (CDCl$_3$, 200 MHz): δ 1.32 (s, 3H), 1.58 (s, 3H), 1.82 (m, 4H), 2.08 (s, 3H), 2.18 (s, 3H), 2.25 (s, 3H), 2.42 (m, 2H), 2.76 (m, 1H), 3.14 (m, 2H), 3.35 (m, 1H), 3.84 (m, 1H), 4.02 (m, 1H), 4.71 (s, 2H), 6.95 (d, J=8.7 Hz, 2H), 7.45 (m, 7H), 7.80 (s, 1H).

EXAMPLE 12

5-[4-[N-[(3RS)-5-Benzyloxy-2,3-dihydro-2,2,4,6,7-pentamethylbenzofuran-3-ylmethyl]-(3R)-piperidinyloxy]phenyl methylene]thiazolidine-2,4-dione (12)

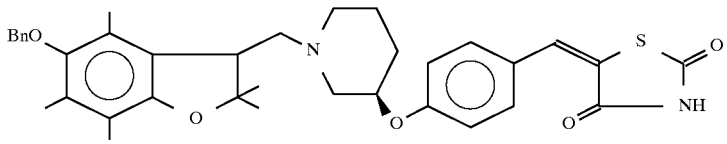

The title compound (0.75 g, 42%) was prepared as a pale yellow solid from the crude mixture (1.5 g) obtained in preparation 16 in a similar manner to that described in example 1. The crude product was chromatographed on silica gel to get 12. mp 150°–152° C.

[α]$_D^{24}$=+87.1 (c, 1.0, CHCl$_3$)

¹H NMR (CDCl₃, 200 MHz): δ 1.13, 1.37 (2s, 3H), 1.43–1.69 (complex m, 5H), 1.88 (m, 2H), 2.09 (s, 3H), 2.11 (s, 3H), 2.19 (s, 3H), 2.36 (m, 2H), 2.63 (m, 2H), 2.91 (m, 1H), 3.09 (m, 2H), 4.42 (m, 1H), 4.71 (s, 2H), 6.95 (m, 2H), 7.45 (m, 7H), 7.81 (s, 1H).

EXAMPLE 13

5-[4-[N-[3(RS)-5-Benzyloy-2,3-dihydro-2,2,4,6,7-pentamethylbenzofuran-3-ylmethyl]-(2S)-pyrrolidine-2-methoxy]phenyl methylene]thiazolidine-2,4-dione maleate

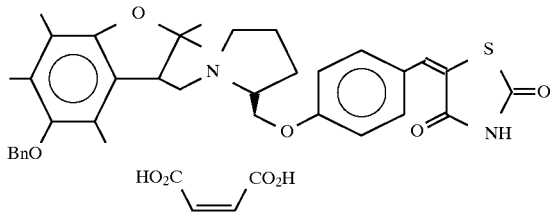

The title compound (0.11 g, 92%) was prepared as a yellow solid from 5-[4-[N-[(3R/S)-5- benzyloxy-2,3-dihydro-2,2,4,6,7-pentamethylbenzofuran-3-ylmethyl]-(2S)-pyrrolidine-2-methoxy]phenyl methylene]thiazolidine-2,4-dione (0.1 g) obtained in example 11 by an analogous procedure to that described in example 2, mp: 158°–161° C.

¹H NMR (CDCl₃, 200 MHz): δ 1.37 (s, 3H), 1.63 (s, 3H), 1.95 (m, 4H), 2.10 (s, 3H), 2.22 (s, 3H), 2.27 (s, 3H), 2.63 (m, 2H), 3.16 (m, 1H), 3.30 (m, 2H), 3.52 (m, 1H), 3.85 (m, 1H), 4.03 (m, 1H), 4.72 (s, 2H), 6.28 (s, 2H), 7.03 (d, J=8.4 Hz, 2H), 7.48 (m, 7H), 7.79 (s, 1H).

EXAMPLE 14

5-[4-[N-[(3R/S)-5-benzyloxy-2,3-dihydro-2,2,4,6,7-pentamethylbenzofuran-3-ylmethyl]-(2S)-pyrrolidine-2-methoxy]phenyl methylene] thiazolidine-2,4-dione, Hydrochloride

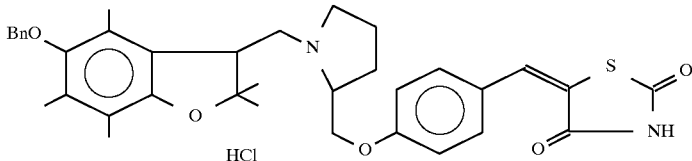

The title compound (0.27 g, 85%) was prepared as a colorless solid from 5-[4-[N-(3R/S)-5-benzyloxy-2,3-dihydro-2,2,4,6,7-pentamethylbenzofuran-3-ylmethyl]-(2S)-pyrrolidine-2-methoxy] phenyl methylene]thiazolidine-2,4-dione (0.3 g) obtained in example 11 by an analogous procedure to that described in example 4, mp :218°–224° C.

¹H NMR (CDCl₃, 200 MHz): δ 1.45 (s, 3H), 1.60 (s, 3H), 1.80 (m, 4H), 2.08 (s, 3H), 2.19 (s, 3H), 2.26 (s, 3H), 2.50 (m, 2H), 2.90 (m, 1H), 3.25 (m, 2H), 3.40 (m, 1H), 4.12 (m, 1H), 4.30 (m, 1H), 4.71 (s, 2H), 7.08 (d, J=8.6 Hz, 2H), 7.49 (m, 7H), 7.76 (s, 1H).

EXAMPLE 15 a) 5-[4-[N-[(3RS)-5-Benzyloxy-2,3-dihydro-2,2,4,6,7-pentamethylbenzofuran-3-ylmethyl]-(2S)-pyrrolidine-2-methoxy]phenyl methyl]thiazolidine-2,4-dione (15a)

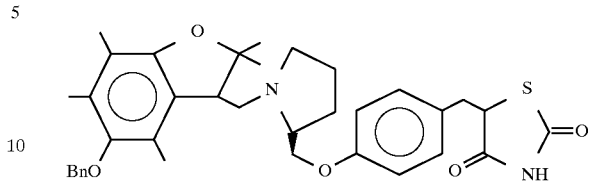

and
b) 5-[4-[N-[(3RS)-2,3-Dihydro-5-hydroxy-2,2,4,6,7-pentamethylbenzofuran-3-ylmethyl]-(2S)-pyrrolidine-2-methoxy]phenyl methyl]thiazolidine-2,4-dione (15b)

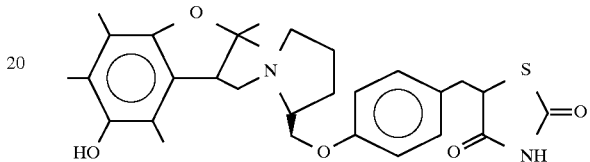

The title compounds 15a and 15b were prepared from ethyl 2-bromo-3-[4-[N-[(3RS)-5-benzyloxy-2,3-dihydro-2,2,4,6,7-pentamethylbenzofuran-3-ylmethyl]-(2S)-pyrrolidine-2-methoxy] phenyl]propanoate (2.5 g) obtained in preparation 31 by a similar procedure to that described in method B of example 5. The crude compound was chromatographed on silica gel to get 15a as a colorless fluffy solid (1.74 g, 75%) and 15b as a fluffy solid (0.4 g, 20%)

15a: mp: 107°–109° C.

[α]$_D^{29}$=−79.5 (c, 1.0, CHCl₃)

¹H NMR (CDCl₃, 200 MHz): δ 1.30,1.34 (2s, 3H), 1.57,1.60 (2s, 3H), 1.79 (m, 4H), 2.09 (s, 3H), 2.19 (s, 3H), 2.26 (s, 3H), 2.45 (m, 2H), 2.78 (m, 1H), 3.03 (m, 1H), 3.14 (m, 2H), 3.38 (m, 1H), 3.55 (m, 1H), 3.74 (m, 1H), 3.98 (m, 1H), 4.46 (m, 1H), 4.70 (m, 2H), 6.78 (m, 2H), 7.10 (m, 2H), 7.42 (m, 5H).

15b: mp: 72°–75° C.

[α]$_D^{29}$=−84.2 (c, 1.0, CHCl₃).

¹H NMR (CDCl₃, 200 MHz): δ 1.26,1.30 (2s, 3H), 1.53,1.58 (2s, 3H), 1.78 (m, 4H), 2.08 (s, 3H), 2.11 (s, 3H), 2.17, 2.20 (2s, 3H), 2.36 (m, 2H), 2.72 (m, 1H), 2.98 (m, 1H), 3.13 (m, 2H), 3.45 (m, 2H), 3.75 (m, 1H), 3.98 (m, 1H), 4.19 (s, 1H), 4.50 (dd, J=9.4, 3.8 Hz, 1H), 6.76 (m, 2H), 7.12 (m, 2H).

EXAMPLE 16

5-[4-[N-[(3RS)-5-Benzyloxy-2,3-dihydro-2,2,4,6,7-pentamethylbenzofuran-3-ylmethyl]-(2S)-pyrrolidine-2-methoxy]phenyl methyl]thiazolidine-2,4-dione, maleate

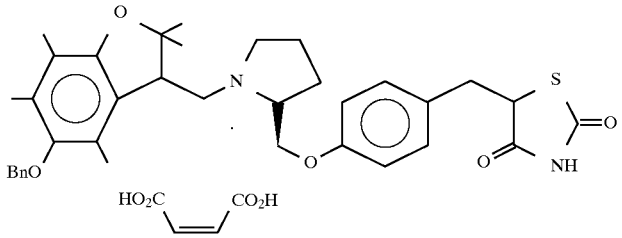

The title compound (0.44 g, 79%) was prepared as a pale yellow solid from 5-[4-[N-[(RS)-5-benzyloxy-2,3-dihydro-2,2,4,6,7-pentamethyl]benzofuran-3-ylmethyl]-(2S)-pyrrolidine-2-methoxy]phenyl methyl]thiazolidine-2,4-dione (15a, 0.47 g), obtained in example 15 by an analogous procedure to that described in example 2, mp. 179°–182° C.

$[\alpha]_D^{25} = -53.4$ (c, 1.0, CHCl$_3$)

$^1$H NMR (CDCl$_3$, 200 MHz): δ 1.36, 1.40 (2s, 3H), 1.62, 1.67 (2s, 3H), 2.06–2.45 (complex m, 15H), 2.81 (m, 1H), 3.14–3.64 (complex m, 5H), 4.16–4.21 (complex m, 2H), 4.50 (m, 1H), 4.64–4.72 (m, 2H), 6.27 (s, 2H), 6.82 (m, 2H), 7.17 (m, 2H), 7.43 (m, 5H).

EXAMPLE 17

5-[4-[N-[(3RS)-5-Benzyloxy-2,3-dihydro-2,2,4,6,7-pentamethyl benzofuran-3-ylmethyl-(2S)-pyrrolidine-2-methoxy]phenyl methyl]thiazolidine-2,4-dione hydrochloride

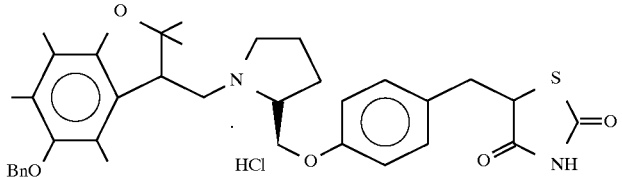

The title compound (0.4 g, 76%) was prepared as a colorless solid from 5-[4-[(3RS)-5-benzyloxy-2,3-dihydro-2,2,4,6,7-pentamethyl]benzofuran-3-ylmethyl]-(2S)-pyrrolidine-2-methoxy]phenyl methyl]thiazolidine-2,4-dione (15a, 0.5 g) obtained in example 15 by an analogous procedure to that described in example 4, mp 161°–163° C.

$[\alpha]_D^{25} = -2.4$ (c, 1.0, CHCl$_3$).

$^1$H NMR (CDCl$_3$, 200 MHz): δ 1.35 (s, 3H), 1.66 (s, 3H), 1.85–2.27 (complex m, 15H), 3.02–3.96 (complex m, 6H), 4.22–4.37 (m, 2H), 4.63 (m, 2H), 4.86 (m, 1H), 6.95 (d, J=7.8 Hz, 2H), 7.22 (d, J=7.8 Hz, 2H), 7.45 (m, 5H), 9.96 (bs, 1H, exchangeable with D$_2$O), 12.05 (s, 1H, exchangeable with D$_2$O).

EXAMPLE 18

5-[4-[N-[(3RS)-2,3-dihydro-5-hydroxy-2,2,4,6,7-pentamethylbenzofuran-3-ylmethyl]-(2S)-pyrrolidine-2-methoxy]phenyl methyl]thiazolidine-2,4-dione, hydrochloride

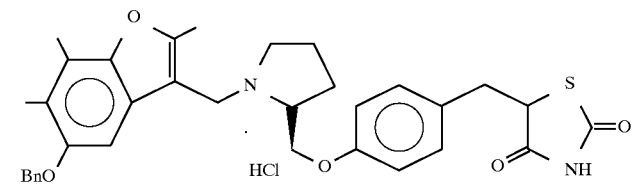

The title compound (0.32 g, 75%) was prepared as a colorless solid from 5-[4-[N-[(3RS)-2,3-dihydro-5-hydroxy-2,2,4,6,7-pentamethylbenzofuran-3-ylmethyl]-(2S)-pyrrolidine-2-methoxy] phenyl methyl]thiazolidine-2,4-dione (15b, 0.4 g) obtained in example 15 by an analogous procedure to that described in example 4, mp 193°–195° C.

[α]$_D^{25}$=−53.9 (c, 1.0, CHCl$_3$).

$^1$H NMR (CDCl$_3$, 200 MHz): δ 1.30 (s, 3H), 1.63 (s, 3H), 1.77–2.28 (complex m, 15H), 3.03–3.38 (complex m, 6H), 4.21 (m, 1H), 4.42 (m, 1H), 4.90 (dd, J=8.72,4.19 Hz, 1H), 6.94 (d, J=8.2, 2H), 7.22 (d, J=7.9 Hz, 2H), 9.86 (bs, 1H, exchangeable with H$_2$O), 12.06 (s, 1H, exchangeable with D$_2$O).

EXAMPLE 19

5-[3-[N-[(3RS)-5-Benzyloxy-2,3-dihydro-2,2,4,6,7-pentamethylbenzofuran-3-ylmethyl]-(2S)-pyrrolidine-2-methoxy]phenyl methylene]thiazolidine-2,4-dione

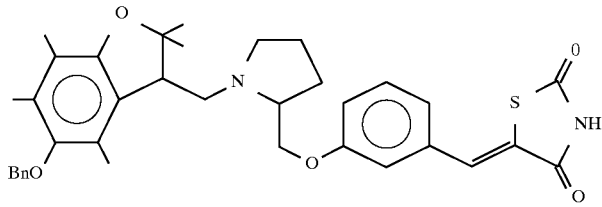

The title compound (0.3 g, 51%) was prepared from 3-[N-(5-benzyloxy-2,3-dihydro-2,2,4,6,7-pentamethyl-benzofuran-3-ylmethyl)-(2S)-pyrrolidine-2-methoxy]benzaldehyde (0.5 g) obtained in, preparation 17 by a similar procedure to that described in example 1. mp 58°–60° C.

[α]$_D^{23}$=−96.7 (c, 1.0, CHCl$_3$)

$^1$H NMR (CDCl$_3$, 200 MHz): δ 1.33 (s, 3H), 1.60 (s, 3H), 1.92 (m, 4H); 2.08 (s, 3H), 2.19, (s, 3H), 2.26 (s, 3H), 2.45 (m, 2H), 2.78 (m, 1H), 3.14 (m, 2H), 3.38 (m, 1H), 3.82 (m, 1H), 4.02 (m, 1H), 4.71 (s, 2H), 6.94 (m, 2H), 7.07 (d, J=7.8 Hz, 1H), 7.45 (m, 6H), 7.80 (s, 1H).

EXAMPLE 20
5-[4-[N-(5-Benzyloxy-2,4,6,7-tetramethylbenzofuran-3-ylmethyl)-(2S)-pyrrolidine-2-methoxy]phenyl methylene]thiazolidine-2,4-dione

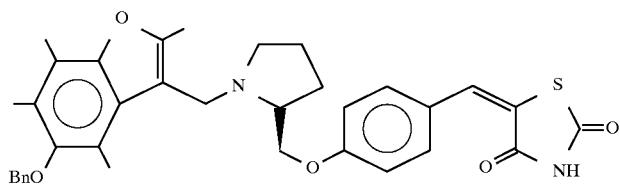

The title compound (0.4 g, 56%) was prepared from 4-[N-(5-benzyloxy-2,4,6,7-tetramethylbenzofuran-3-ylmethyl)-(2S)-pyrrolidine-2-methoxy]benzaldehyde (18a, 0.6 g) obtained in preparation 18 by an analogous procedure to that described in example 1, mp. 180°–183° C.

$^1$H NMR (CDCl$_3$, 200 MHz): δ 1.75 (m, 4H), 2.05 (m, 1H), 2.31 (s, 3H), 2.38 (s, 3H), 2.42 (s, 3H), 2.60 (s, 3H), 3.00 (m, 2H), 3.63 (d, J=12.9 Hz, 1H), 3.78 (m, 1H), 3.83 (m, 1H), 4.04 (d, J=12.9 Hz, 1H), 4.71 (s, 2H), 6.78 (d, J=8.6 Hz, 2H), 7.44 (m, 7H), 7.78 (s, 1H).

EXAMPLE 21

5-[4-[N-(5-Benzyloxy-2,4,6,7-tetramethylbenzofuran-3-ylmethyl)-(2S)-pyrrolidine-2-methoxy]phenyl methylene]thiazolidine-2,4-dione sodium salt

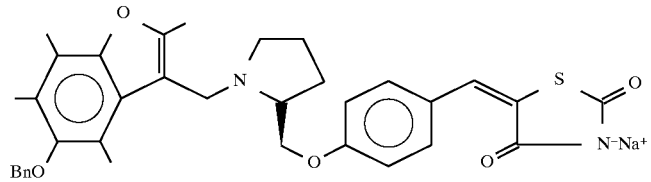

The title compound (0.28 g, 67%) was prepared as a pale yellow solid from 5-[4-[N-[5-benzyloxy-2,4,6,7-tetramethylbenzofuran-3-ylmethyl]-(2S)-pyrrolidine-2-methoxy]phenyl methylene]thiazolidine-2,4-dione (0.4 g) obtained in example 20 by an analogous procedure to that described in example 3, mp. 210°–218° C.

[α]$_D^{25}$=+65.1 (c, 1.0, CHCl$_3$)

$^1$H NMR (CDCl$_3$, 200 MHz): δ 1.68 (m, 4H), 2.01 (m, 1H), 2.23 (s, 3H), 2.30 (s, 3H), 2.40 (s, 3H), 2.59 (s, 3H), 2.88 (m, 2H), 3.46 (d, J=12.8 Hz, 1H), 3.90 (m, 2H), 4.12 (d, J=12.9 Hz, 1H), 4.62 (s, 2H), 6.86 (d, J=8.7 Hz, 2H), 7.41 (m, 8H).

EXAMPLE 22

5-[4-[N-(5-Benzyloxy-2,4,6,7-tetramethylbenzofuran-3-ylmethyl)-(3R)-piperidinyloxy] phenyl methylene]thiazolidine-2,4-dione

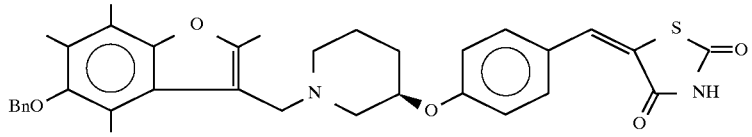

The title compound (0.9 g, 75%) was prepared as a yellow solid from 4-[N-(5-benzyloxy-2,4,6,7-tetramethylbenzofuran-3-ylmethyl)-(3R)-piperidinyloxy]benzaldehyde (18b, 1.0 g) obtained in preparation 18 by a similar procedure as described in example 1, mp 100°–103° C.

$[\alpha]_D^{20}$=−52.4 (c, 1.0, CHCl$_3$)

$^1$H NMR (CDCl$_3$, 200 MHz): δ 1.58 (m, 3H), 1.78 (m, 1H), 2.16 (s, 2H), 2.33 (s, 3H), 2.40 (s, 6H), 2.73 (s, 3H), 2.78 (m, 1H), 3.15 (m, 1H), 3.48 (d, J=4.9 Hz, 2H), 4.34 (m, 1H), 4.77 (s, 2H), 6.91 (d, J=8.7 Hz, 2H), 7.42 (m, 7H), 7.74 (s, 1H).

EXAMPLE 23

5-[4-[N-(5-Benzyloxy-2,4,6,7-tetramethylbenzofuran-3-ylmethyl)-(2S)-pyrrolidine-2-methoxy]phenyl methyl]thiazolidine-2,4-dione

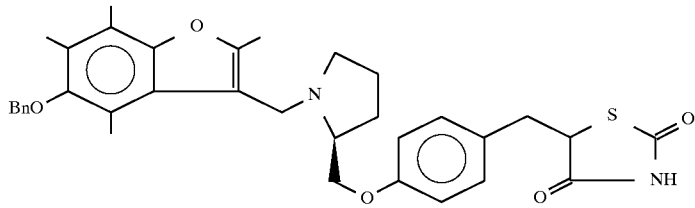

The title compound (0.4 g, 20%) was prepared as a colorless solid from ethyl 2-bromo-3-[4-[N-(5-benzyloxy-2,4,6,7-tetramethylbenzofuran-3-ylmethyl)-(2S)-pyrrolidine-2-methoxy]phenyl] propanoate (2.25 g) obtained in preparation 32 by an analogous procedure to that described in method B of example 5. mp, 55°–57° C.

$[\alpha]_D^{25}$=+25.2 (c, 0.5, CHCl$_3$)

$^1$H NMR (CDCl$_3$, 200 MHz): δ 1.75 (m, 4H), 2.05 (m, 1H), 2.30 (s, 3H), 2.37 (s, 3H), 2.41 (s, 3H), 2.60 (s, 3H), 2.98 (m, 2H), 3.10 (m, 1H), 3.41 (m, 1H), 3.55 (m, 1H), 3.72 (m, 1H), 3.90 (m, 1H), 4.12 (m, 1H), 4.45 (m, 1H), 4.74 (s, 2H), 6.70 (m, 2H), 7.04 (d, J=7 Hz, 2H), 7.42 (m, 5H).

EXAMPLE 24

5-[4-[N-(5-Benzyloxy-2-methylbenzofuran-3-ylmethyl)-(2S)-pyrrolidine-2-methoxy]phenyl methylene]thiazolidine-2,4-dione

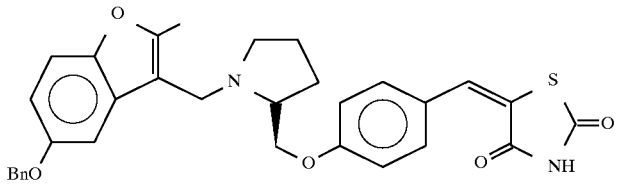

The title compound (0.4 g, 73%) was prepared as a pale yellow solid from 4-[N-[5-benzyloxy-2-methylbenzofuran-3-ylmethyl]-(2S)-pyrrolidine-2-methoxy] benzaldehyde (0.45 g) obtained in preparation 19 by a similar procedure to that described in example 1.

$[\alpha]_D^{24}$=−12.2 (c, 1.0, CHCl$_3$)

¹H NMR (CDCl₃, 200 MHz): δ 1.75 (m, 3H), 1.93 (m, 2H), 2.46 (s, 3H), 3.12 (m, 2H), 3.89 (d, J=14.1 Hz, 1H), 4.05 (m, 1H), 4.13 (m, 1H), 4.19 (d, J=14.1 Hz, 1H), 4.92 (s, 2H), 6.87 (m, 1H), 6.94 (d, J=8.9 Hz, 2H), 7.13 (d, J=2.2 Hz, 1H), 7.36 (m, 8H), 7.55 (s, 1H).

EXAMPLE 25

4-[N-[5-Benzyloxy-2-methylbenzofuran-3-yl-methyl]-(3R)-piperidinyloxy]phenyl methylene]thiazolidine-2,4-dione (25)

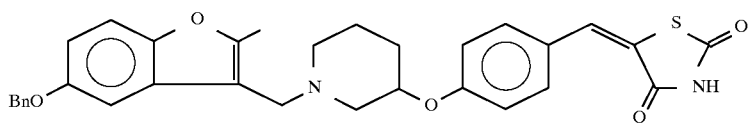

The title compound (1.5 g, 41%) was prepared as a yellow solid from the crude mixture (3 g) obtained in preparation 19 by a similar procedure to that described in example 1. The crude product was chromatographed on silica gel to get 25, mp 150°–155° C.

[α]_D^{30} = −7.8 (c, 1.0, CHCl₃).

¹H NMR (CDCl₃, 200 Mhz) : δ 1.33 (m, 2H), 1.84 (m, 1H), 1.92–2.28 (complex m, 3H), 2.39 (s, 3H), 2.76 (m, 1H), 3.08 (m, 1H), 3.62 (d, J=2.5 Hz, 2H), 4.35 (m, 1H), 5.09 (s, 2H), 6.89 (m, 3H), 7.35 (m, 9H), 7.73 (s, 1H).

EXAMPLE 26

5-[4-[N-(5-Benzyloxy-2-methylbenzofuran-3-ylmethyl)-(2S)-pyrrolidine-2-methoxy]phenyl methyl]thiazolidine-2,4-dione

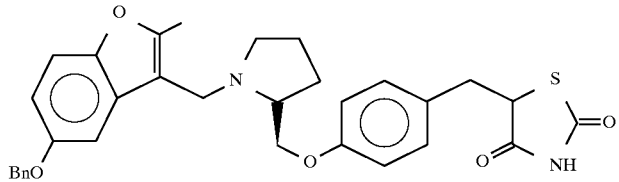

The title compound (0.7 g, 54%) was prepared as a colorless solid from 5-[4-[N-(5-benzyloxy-2-methylbenzofuran-3-ylmethyl)-(2S)-pyrrolidine-2-methoxy]phenyl methylene]thiazolidine-2,4-dione (1.3 g) obtained in example 24, by an analogous procedure to that described in method A of example 5. mp: 68°–71° C.

[α]_D^{25} = −11.6 (c, 1.0, CHCl₃)

¹H NMR (CDCl₃, 200 MHz): δ 1.76 (m, 4H), 2.05 (m, 1H), 2.41 (s, 3H), 3.05 (m, 3H), 3.34 (m, 1H), 3.64 (m, 1H), 3.96 (m, 2H), 4.19 (m, 1H), 4.36 (dd, J=8.5,3.1 Hz, 1H), 4.89 (s, 2H), 6.84 (m, 3H), 7.14 (m, 3H), 7.35 (m, 6H).

EXAMPLE 27

5-[4-[N-(1-Methylindol-3-ylmethyl)-(2S)-pyrrolidine-2-methoxy]phenyl methylene]thiazolidine-2,4-dione The title compound (0.35 g, 27%) was prepared from 4-[N-(1-methylindol-3-ylmethyl)-(2S)-pyrrolidine-2-methoxy]benzaldehyde (1.02 g) obtained in preparation 20, by a similar procedure to that described in example 1. mp 159°–160° C.

[α]_D^{26} = −42.49 (c, 1.0, CHCl₃)

¹H NMR (CDCl₃, 200 MHz): δ 1.89 (m, 2H), 2.17 (m, 2H), 2.96 (m, 1H), 3.49 (m, 1H), 3.75 (m, 1H), 3.86 (s, 3H), 4.28 (m, 2H), 4.53 (d, J=5.3 Hz, 2H), 6.89 (d, J =8.0 Hz, 2H), 7.28 (m, 7H), 7.75 (d, J=6.6 Hz, 1H).

EXAMPLE 28

5-[4-[2-[4-[(2RS)-6-Benzyloxy-2,5,7,8-tetramethylchroman-2-ylmethyl]piperazine-1-yl]ethoxy]phenyl methylene]thiazolidine-2,4-dione

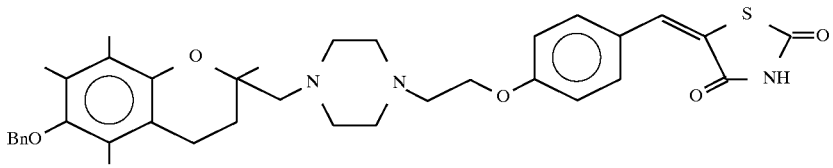

The title compound (0.16 g, 67%) was prepared as a pale yellow solid from 4-[2-[4-(6-benzyloxy-2,5,7,8-tetramethylchroman-2-ylmethyl)piperazine-1-yl]ethoxy]benzaldehyde, (0.2 g) obtained in preparation 21 by a similar procedure to that described in example 1. mp 192°–194° C.

$^1$H NMR (CDCl$_3$, 200 MHz): δ 1.24 (s, 3H), 1.7 (m, 1H), 2.0 (m, 1H), 2.07 (s, 3H), 2.17 (s, 3H), 2.22 (s, 3H), 2.45–3.0 (m, 14H), 4.2 (bs, 2H), 4.7 (s, 2H), 6.88 (d, J=8.8 Hz, 2H), 7.2–7.6 (m, 7H).

EXAMPLE 29

5-[4-[2-[4-(1-Methylindol-3-ylmethyl)piperazin-1-yl]ethoxy]phenyl methylene]thiazolidine-2,4-dione

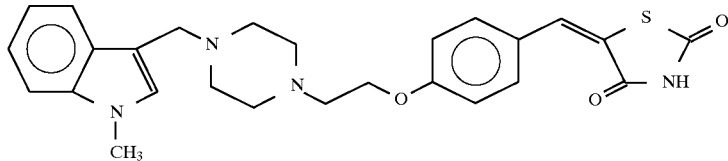

The title compound (0.7 g, 84%) was prepared as a pale yellow solid from 4-[2-[4-[(1-methylindol-3-ylmethyl)piperazin-1-yl]ethoxy]benzaldehyde (0.6 g) obtained in preparation 22, by a similar procedure to that described in example 1. mp 183°–188° C.

$^1$H NMR (CDCl$_3$+CD$_3$OD, 200 MHz): δ 2.69 (bs, 8H), 2.86 (t, J=5.4 Hz, 2H), 3.81 (s, 5H), 4.17 (t, J=5.21 Hz, 2H), 6.99 (d, J=8.72 Hz, 2H), 7.19 (m, 4H), 7.48 (m, 2H), 7.70 (m, 2H).

To a solution of 0.5 g of the product obtained in example 1, in 6 ml of acetic acid (6 ml) was added concentrated hydrochloric acid (2 ml). The resulting mixture was heated at 60° C. for 2 h. At the end of this time, the solvent was removed under reduced pressure and the residue was diluted with CHCl$_3$ and washed with aqueous sodium bicarbonate solution followed by brine. The organic layer was dried over anhydrous calcium chloride and the solvent was removed by distillation under reduced pressure. The crude product was purified by column chromatography on silica gel using 0 to 1% (gradient elution) methanol in chloroform to afford 0.42 g (98%) of the title compound as a pale yellow solid. mp 82°–84° C.

$[α]_D^{27}$=–29.44 (c, 0.9, CHCl$_3$)

$^1$H NMR (CDCl$_3$, 200 MHz): δ 1.21, 1.25 (2s, 3H), 1.5–2.05 (m, 6H), 2.13 (m, 9H), 2.3–3.2 (m, 6H), 3.4 (m, 1H), 3.9 (m, 1H), 4.05 (m, 1H), 6.95 (d, J=7.4 Hz, 2H), 7.45 (m, 2H), 7.82, 7.83 (2s, 1H).

EXAMPLE 30

5-[4-[N-[(2RS)-6-Hydroxy-2,5,7,8-tetramethylchroman-2-ylmethyl]-(2S)-pyrrolidine-2-methoxy] phenyl methylene]thiazolidine-2,4-dione

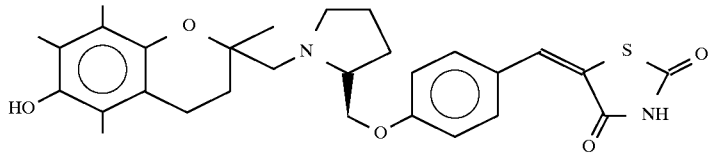

EXAMPLE 31

5-[4-[N-[(2RS)-6-Hydroxy-2,5,7,8-tetramethylchroman-2-ylmethyl]-(2S)-pyrrolidine-2-methoxy] phenyl methyl]thiazolidine-2,4-dione

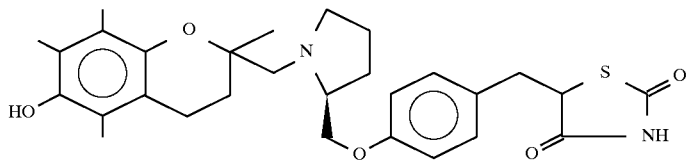

The title compound (0.22 g, 86%) was prepared as a pale yellow solid from 5-[4-[N-[(2RS)-6-benzyloxy-2,5,7,8-tetramethylchroman-2-ylmethyl]-(2S)-pyrrolidine-2-methoxy]phenyl methyl] thiazolidine-2,4-dione (0.3 g), obtained in example 5 by an analogous procedure to that described in example 30. mp. 76°–78° C.

$^1$H NMR (CDCl$_3$, 200 MHz): δ 1.21 (3s, 3H), 1.5–2.05 (m, 6H), 2.1 (s, 6H), 2.15 (s, 3H), 2.3–2.8 (m, 4H), 2.9–3.25 (m, 3H), 3.4 (m, 2H), 3.6–4.0 (m, 2H), 4.5 (dd, J=8.8 Hz and 3.8 Hz), 6.8 (m, 2H), 7.12 (d, J=8.2 Hz, 2H).

EXAMPLE 32

5-[4-[N-[(3R/S)-5-Hydroxy-2,3-dihydro-2,2,4,6,7-pentamethylbenzofuran-3-ylmethyl]-(2S)-pyrrolidine-2-methoxy]phenyl methylene] thiazolidine-2,4-dione

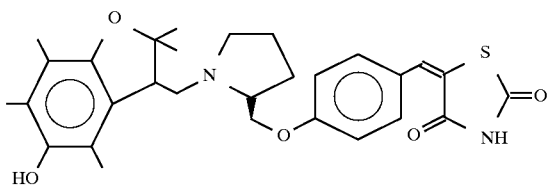

The title compound (0.13 g, 43%) was prepared as a yellow solid from 5-[4-[N-[(3R/S)-5-benzyloxy-2,3-dihydro-2,2,4,6,7-pentamethylbenzofuran-3-ylmethyl]-(2S)-pyrrolidine-2-methoxy] phenyl methylene] thiazolidine-2,4-dione (0.4 g) obtained in example 11, by an analogous procedure to that described in example 30. mp 75°–77° C.

$[\alpha]_D^{29}$=−175.5 (c, 1.0, CHCl$_3$)

$^1$H NMR (CDCl$_3$, 200 MHz): δ 1.31 (s, 3H), 1.58 (s, 3H), 1.85 (m, 4H), 2.09 (s, 3H), 2.13 (s, 3H), 2.22 (s, 3H), 2.38 (m, 2H), 2.76 (m, 1H), 3.11 (m, 2H), 3.36 (m, 1H), 3.85 (dd, J=9.1 and 6.4 Hz, 1H), 4.06 (dd, J=9.1 and 4.9 Hz, 1H), 4.16 (bs, 1H), 6.95 (d, J=8.7 Hz, 2H), 7.43 (d, J=8.7 Hz, 2H), 7.8 (s, 1H).

EXAMPLE 33

5-[4-[N-(5-Hydroxy-2,4,6,7-tetramethylbenzofuran-3-ylmethyl)-(2S)-pyrrolidine-2-methoxy]phenyl methylene]thiazolidine-2,4-dione

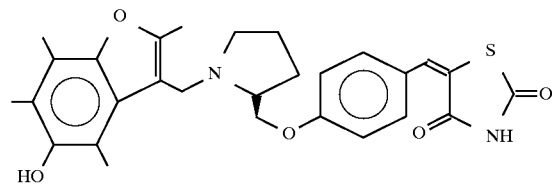

The title compound (0.27 g, 45%) was prepared from 5-[4-[N-(5-benzyloxy-2,4,6,7-tetramethylbenzofuran-3-ylmethyl)-(2S)-pyrrolidine-2-methoxy]phenyl methylene] thiazolidine-2,4-dione (0.7 g) obtained in example 20, by an analogous procedure to that described in example 30. mp, 157°–158° C.

$[\alpha]_D^{26}$=+75.1 (c, 0.7, EtOAc)

$^1$H NMR (CDCl$_3$, 200 MHz): δ 1.78 (m, 4H), 2.04 (m, 1H), 2.24 (s, 3H), 2.38 (s, 3H), 2.40 (s, 3H), 2.51 (s, 3H), 3.04 (m, 2H), 3.62 (d, J=12.9 Hz, 1H), 3.79 (m, 1H), 3.83 (m, 1H), 4.04 (d, J=12.9 Hz, 1H), 6.76 (d, J=8.9 Hz, 2H), 7.38 (d, J=8.7 Hz, 2H), 7.78 (s, 1H).

EXAMPLE 34

5-[4-[N-(5-Hydroxy-2,4,6,7-tetramethylbenzofuran-3-ylmethyl)-(3R)-piperidinyloxy] phenylmethylene]thiazolidine-2,4-dione

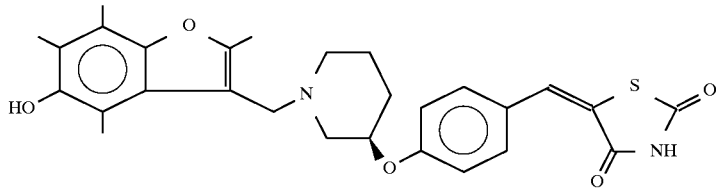

The title compound (0.1 g, 47%) was prepared from 4-[N-(5-benzyloxy-2,4,6,7-tetramethyl-3-ylmethyl)-(3R)-piperidinyloxy]phenyl methylene]thiazolidine-2,4-dione (0.25 g) obtained in example 22, by an analogous procedure as described in example 30, mp. 192°–195° C.

$[\alpha]_D^{20}$=−36.3 (c, 1.0, CHCl$_3$)

$^1$H NMR (CDCl$_3$, 200 MHz): δ 1.45 (m, 3H), 1.90 (m, 1H), 2.09 (m, 2H), 2.24 (s, 3H), 2.33 (s, 3H), 2.35 (s, 3H) 2.65 (m, 1H), 3.05 (m, 1H), 3.48 (d, J=3.1 Hz, 2H), 4.35 (m, 1H), 6.90 (d, J=8.7 Hz, 2H), 7.37 (d, J=8.7 Hz, 2H), 7.68 (s, 1H)

EXAMPLE 35

5-[3-[N-[(3RS)-[2,3-Dihydro-5-hydroxy-2,2,4,6,7-pentamethylbenzofuran-3-ylmethyl]-(2S)-pyrrolidine-2-methoxy]phenyl methylene]thiazolidine-2,4-dione

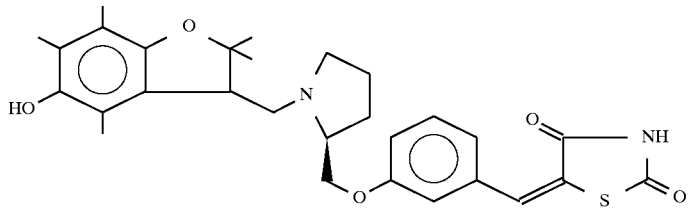

The title compound (0.68 g, 80%) was prepared from 5-[3-[N-[(3RS)-5-benzyloxy-2,3-dihydro-2,2,4,6,7-pentamethylbenzofuran-3-ylmethyl]-(2S)-pyrrolidine-2-methoxy]phenyl methylene] thiazolidine-2,4-dione (1 g) obtained in example 19 by an analogous procedure to that described in example 30, mp 70°–72° C.

$[\alpha]_D^{23}$=−83.9 (c, 1.0, CHCl$_3$)

$^1$H NMR (CDCl$_3$, 200 MHz): δ 1.31 (s, 3H), 1.59 (s, 3H), 1.85 (m, 4H), 2.08 (s, 3H), 2.12 (s, 3H), 2.21 (s, 3H), 2.35 (m, 2H), 2.78 (m, 1H), 3.14 (m, 2H), 3.38 (m, 1H), 3.84 (m, 1H), 4.04 (dd, J=9.13 and 4.8 Hz, 1H), 4.19 (bs, 1H, exchangeable with D$_2$O), 6.96 (m, 2H), 7.06 (m, 1H), 7.34 (m, 1H), 7.79 (s, 1H).

EXAMPLE 36

5-[4-[N-(5-Hydroxy-2-methylbenzofuran-3-ylmethyl)-(2S)-pyrrolidine-2-methoxy]phenyl methylene]thiazolidine-2,4-dione

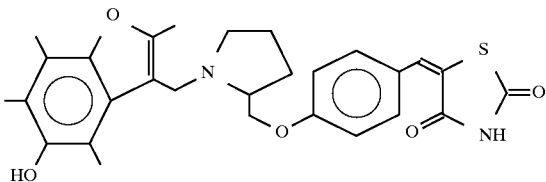

The title compound (0. 1 g, 40%) was prepared from 5-[4-[N-(5-benzyloxy-2-methylbenzofuran-3 -ylmethyl)-(2S)-pyrrolidine-2-methoxy]phenyl methylene]thiazolidine-2,4-dione, (0.3 g) obtained, in example 24 by an analogous procedure to that described in example 30, mp 206°–208° C.

$[\alpha]_D^{25}$=+48.4 (c, 1.0, pyridine)

$^1$H NMR (CDCl$_3$, 200 MHz): δ 1.75 (m, 2H), 1.77 (m, 2H), 2.02 (m, 1H), 2.43 (s, 3H), 3.08 (m, 1H), 3.21 (m, 1H), 3.75 (d, J=13.61 Hz, 1H) 4.09 (m, 2H), 4.19 (d, J=13.61 Hz, 1H), 6.79 (m, 1H), 6.95 (d, J=8.7 Hz, 2H), 7.06 (m, 1H), 7.16 (m, 1H), 7.34 (d, J=8.7 Hz, 2H), 7.59 (s, 1H).

EXAMPLE 37

5-[4-[N-(3,5-Dimethyl-4-methoxy-2-pyridylmethyl]-(2S)-pyrrolidine-2-methoxy]phenyl methylene]thiazolidine-2,4-dione

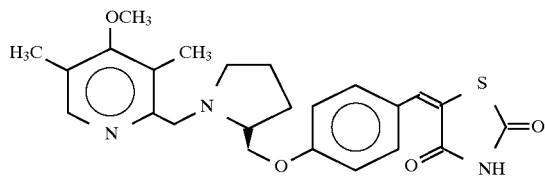

The title compound (1.2 g, 30%) was prepared as a brown colored solid from the crude product obtained in preparation 23, by a similar procedure to that described in example 1, mp: 142° C.

$[\alpha]_D^{23}$=−12.6 (c, 1.0, CHCl$_3$)

$^1$H NMR (CDCl$_3$, 200 MHz): δ 1.70–2.10 (m, 4H), 2.20 (s, 3H), 2.30 (s, 3H), 2.46–2.68 (m, 1H), 3.00–3.12 (m, 1H), 3.22–3.30 (m, 1H), 3.74 (s, 3H), 388–4.12 (m, 3H), 4.32 (d, J=12 Hz, 1H), 6.88 (d, J=6 Hz, 2H), 7.30 (d, J=6 Hz, 2H), 7.48 (s, 1H), 8.24 (s, 1H).

EXAMPLE 38

5-[4-[N-(3,5-Dimethyl-4-methoxy-2-pyridylmethyl]-(2S)-pyrrolidine-2-methoxy]phenyl methyl]thiazolidine-2,4-dione

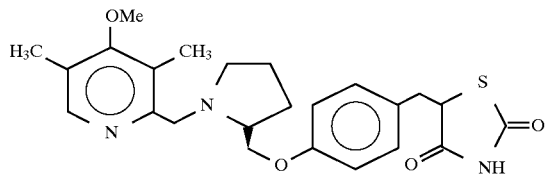

5-[4-[N-[3,5-dimethyl-4-methoxy-2-pyridylmethyl]-(2S)-pyrrolidine-2-methoxy]phenyl methylene]thiazolidine-2,4-dione (1 g), obtained in example 37, was dissolved in 1,4-dioxane (10 ml) and was reduced with hydrogen (70 Psi) in the presence of 10% palladium on charcoal (1.5 g) at ambient temperature until hydrogen uptake ceased (nearly 40 h). The solution, was filtered through a bed of celite, the filter pad was washed exhaustively with dioxane and the combined filtrate was evaporated to dryness under reduced pressure. The crude product was chromatographed on silica gel using 10% MeOH in EtOAc to give 0.34 g (34%) of the title compound.

$^1$H NMR (CDCl$_3$ 200 MHz: δ 1.64–2.20 (m, 4H), 2.20 (s, 3H), 2.30 (s, 3H), 2.42–2.60 (m, 1H), 2.86–3.24 (m, 4H), 3.32–3.52 (m, 1H), 3.70 (s, 3H), 3.78–4.02 (m, 2H), 4.20–4.40 (m, 2H), 6.78 (d, J=6 Hz, 2H), 7.10 (d, J=6 Hz, 2H), 8.10 (s, 1H).

EXAMPLE 39

5-[4-[[N-[3,5-Dimethyl-4-methoxy-2-pyridyl-methyl]-(2S)-pyrrolidine-2-methoxy]phenyl methylene]thiazolidine-2,4-dione, maleate

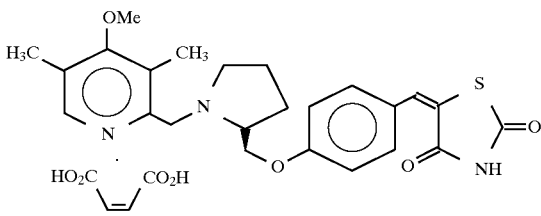

The title compound (0.36 g, 63%) was prepared as brown colored solid from 5-[4-[N-(3,5-dimethyl-4-methoxy-2-pyridylmethyl]-(2S)-pyrrolidine-2-methoxy]phenyl methylene]-thiazolidine-2,4-dione (0.45 g), obtained in example 37 by an analogous procedure to that described in example 2. mp: 182° C.

$^1$H NMR (CD$_3$OD, 200 MHz): δ 2.02–2.48 (m, 4H), 2.28 (s, 6H), 3.28–3.40 (m, 2H), 3.66–3.78 (m, 1H), 3.88 (s, 3H), 4.28–4.40 (m, 2H), 4.60 (ABq, J=12.42 Hz, 2H), 6.28 (s, 3H), 6.92 (d, J=6 Hz, 2H), 7.44 (d, J=6 Hz, 2H), 7.74 (s, 1H), 8.20 (s, 1H).

Mutation in colonies of laboratory animals and different sensitivities to dietary regimens have made the development of animal models with non-insulin dependent diabetes associated with obesity and insulin resistance possible. Genetic models such as db/db and ob/ob (See Diabetes, (1982) 31(1): 1–6) in mice and fa/fa and zucker rats have been developed by the various laboratories for understanding the pathophysiology of disease and testing the efficacy of new antidiabetic compounds (Diabetes, (1983) 32: 830–838 ; Annu. Rep. Sankyo Res. Lab. (1994). 46: 1–57). The homozygous animals, C57 BL/KsJ-db/db mice developed by Jackson Laboratory, US, are obese, hyperglycemic, hyperinsulinemic and insulin resistant (J. Clin. Invest., (1990) 85: 962–967), whereas heterozygous are lean and normoglycemic. In db/db model, a mouse progressively develops insulinopenia with age, a feature commonly observed in late stages of human type II diabetes when blood sugar levels are insufficiently controlled. The state of pancreas and its course vary according to the models. Since this model resembles that of type II diabetes mellitus, the compounds of the present invention were tested for blood sugar and triglycerides lowering activities.

The compounds of the present invention showed blood sugar and triglycerides lowering activities through improved insulin resistance. This was demonstrated by the following in vivo experiments.

Male C57BL/KsJ-db/db mice of 8 to 14 weeks age, having body weight range of 35 to 60 grams, procured from the Jackson Laboratory, USA, were used in the experiment. The mice were provided with standard feed (National Institute of Nutrition, Hyderabad, India) and acidified water, ad libitum. The animals having more than 300 mg/dl blood sugar were used for testing. The number of animals in each group was 4.

The random blood sugar and triglyceride levels were measured by collecting blood (100 μl) through orbital sinus, using heparinised capillary in tubes containing EDTA which was centrifuged to obtain plasma. The plasma glucose and triglyceride levels were measured spectrometrically, by glucose oxidase and glycerol-3-PO$_4$ oxidase/peroxidase enzyme (Dr. Reddy's Lab. Diagnostic Division Kits, Hyderabad, India) methods respectively. On 6th day the blood samples were collected one hour after administration of test compounds/vehicle for assessing the biological activity.

Test compounds were suspended on 0.25% carboxymethyl cellulose and administered to test group at a dose of 30 mg/kg through oral gavage daily for 6 days. The control group received vehicle (dose 10 ml/kg). Troglitazone (100 mg/kg, daily dose) was used as a standard drug which showed 28% reduction in random blood sugar level on 6th day.

The blood sugar and triglycerides lowering activities of the test compound was calculated according to the formula:

$$\text{Blood sugar/triglycerides lowering activity (\%)} = 1 - \frac{DT/DC}{TC/ZC} \times 100$$

ZC=Zero day control group value
DC=Zero day treated group value
TC=Control group value on test day
DT=Treated group value on the test day
No adverse effects were observed for any of the mentioned compounds of invention in the above test.

| Compound | Reduction in Blood Glucose Level (%) | Triglyceride Lowering (%) |
|---|---|---|
| Example 7 | 36 | 70 |
| Example 13 | 45 | 42 |
| Example 11 | 16 | 43 |
| Example 22 | NA | NA |

NA = Not Active at dose of 30 mg/Kg but has activity at a higher dose.

The experimental results from the db/db mice suggest that the novel compounds of the present invention also possess therapeutic utility for prophylactic or regular treatment of obesity, cardiovascular disorders such as hypertension, hyperlipidaemia and other diseases; as it is known from the literature that such diseases are interrelated to each other.

We claim:

1. A compound of formula (I)

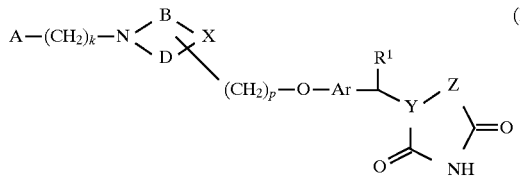

its tautomeric forms, its stereoisomers, its polymorphs, its pharmaceutically acceptable salts or its pharmaceutically acceptable solvates, where A represents substituted or unsubstituted, single or fused, aromatic group or substituted or unsubstituted, single or fused, heterocyclic group with one or more hetero atoms selected from the group of nitrogen, oxygen and sulfur; B represents a substituted or unsubstituted linking group between N and X and B contains 1–4 carbon atoms; D represents a bond or D represents a substituted or unsubstituted linking group between N and X when D contains 1–4 carbons atoms; with the proviso that when the linking group B, D or both is substituted the substituent is not =O or =S; X represents, either a $CH_2$ group or a hetero atom selected from the group of nitrogen, sulfur and oxygen; Ar represents an optionally substituted divalent single or fused aromatic or heterocyclic group; $R^1$ represents hydrogen atom, hydroxy, alkoxy, halogen or lower alkyl group or forms a bond together with the adjacent group Y; Y represents a nitrogen atom or a group $CR^2$ where $R^2$ represents hydrogen, hydroxy, alkoxy, halogen or lower alkyl or $R^2$ forms a bond together with $R^1$; Z represents an oxygen atom or a sulfur atom when Y is $CR^2$ and Z represents an oxygen atom when Y is a nitrogen atom; k is an integer ranging from 1–4 and p is an integer ranging from 0 to 4.

2. A compound as claimed in claim 1, where when $R^2$ is a lower alkyl group the lower alkyl group is selected from methyl, ethyl or propyl.

3. A compound as claimed in claim 1, wherein k represents an integer 1 or 2.

4. A compound as claimed in claim 1, wherein the heterocycle comprising N, B, X and D is a single five or six membered ring.

5. A compound as claimed in claim 1, wherein the heterocycle comprising N, B, X and D is unsubstituted.

6. A compound as claimed in claim 1, wherein the integer p is 0 or 1.

7. A compound as claimed in claim 1, wherein the Ar group represents a divalent phenyl or a napthyl group.

8. A compound as claimed in claim 1, wherein the heterocycle comprising Y and Z is a 2,4-dioxothiazolidin-5-yl group.

9. An intermediate of formula (III)

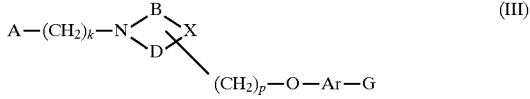

where A represents substituted or unsubstituted, single or fused, aromatic group or substituted or unsubstituted, single or fused, heterocyclic group with one or more hetero atoms selected from the group of nitrogen, oxygen and sulfur; B represents a substituted or unsubstituted linking group between N and X and B contains 1–4 carbon atoms; D represents a bond or D represents a substituted or unsubstituted linking group between N and X when D contains 1–4 carbons atoms; with the proviso that when the linking group B, D or both is substituted the substituent is not =O or =S; X represents, either a $CH_2$ group or a hetero atom selected from the group of nitrogen, sulfur and oxygen; Ar represents an optionally substituted divalent single or fused aromatic or heterocyclic group; k is an integer ranging from 1–4 and and p is an integer ranging from 0 to 4, and G represents —CHO, —$NO_2$, —$NH_2$, —CH=NHOH, —$CH_2$NHOH, —$CH_2$N(OH)$CONH_2$ or —$CH_2$CH(J) COOR, where J represents a hydroxy group, or halogen atom and R represents H or lower alkyl group.

10. A process for preparing an intermediate of formula (III)

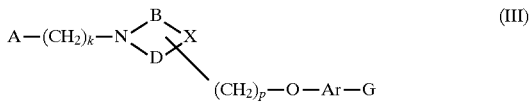

where A represents substituted or unsubstituted, single or fused, aromatic group or substituted or unsubstituted, single or fused, heterocyclic group with one or more hetero atoms selected from the group of nitrogen, oxygen and sulfur; B represents a substituted or unsubstituted linking group between N and X and B contains 1–4 carbon atoms; D represents a bond or D represents a substituted or unsubstituted linking group between N and X when D contains 1–4 carbons atoms; with the proviso that when the linking group B, D or both is substituted the substituent is not =O or =S; X represents, either a $CH_2$ group or a hetero atom selected from the group of nitrogen, sulfur and oxygen; Ar represents an optionally substituted divalent single or fused aromatic or heterocyclic group; k is an integer ranging from 1–4 and and p is an integer ranging from 0 to 4,0 and G represents —CHO, or $NO_2$ which comprises:

a) reacting the compound of the formula (IV),

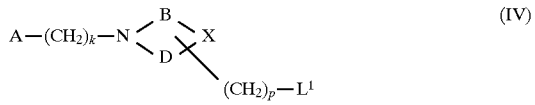
(IV)

wherein, A, B, D, X, k and p are as defined above and $L^1$ is a halogen atom or a leaving group with a compound of the formula (V)

HO—Ar—G     (V)

where G is a CHO or a $NO_2$ group and Ar is as defined above;

b) reacting a compound of formula (VI)

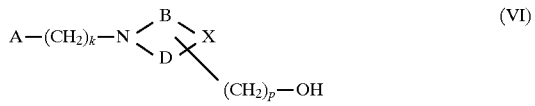
(VI)

where A, B, D, X, k and p are as defined above with a compound of formula (VII)

$L^2$—Ar—G     (VII)

where G is a CHO or $NO_2$ group and Ar is as defined above and $L^2$ represents a halogen atom;

c) reacting a compound of formula (VI)

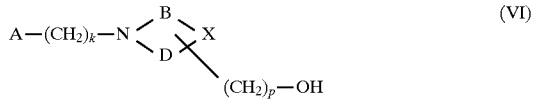
(VI)

where A, B, D, X, k and p are as defined above with a compound of formula (V)

HO—Ar—G     (V)

where G is a CHO or $NO_2$ group and Ar as defined above;

d) reacting a compound of formula (VIII)

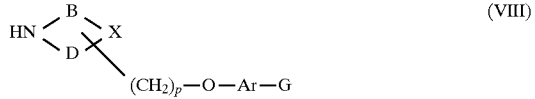
(VIII)

where B, D, X, Ar, k and p are as defined above, with a compound of formula (IX)

A—$(CH_2)_k$—$L^1$     (IX)

where A, and k are as defined above and $L^1$ is as defined in (a) above.

11. A process for the preparation of novel azolidinedione derivatives of formula (I), their tautomeric forms, their stereoisomers, their polymorphs, their pharmaceutically acceptable salts and their pharmaceutically acceptable solvates wherein $R^1$ represents hydrogen, Y represents CH group and Z represents a sulfur or oxygen atom and where A represents, substituted or unsubstituted, single or fused, aromatic group or substituted or unsubstituted, single or fused, heterocyclic group with one or more hetero atoms selected from the group of nitrogen, oxygen and sulfur; B represents a substituted or unsubstituted linking group between N and X and B contains 1–4 carbon atoms; D represents a bond or D represents a substituted or unsubstituted linking group between N and X when D contains 1–4 carbons atoms; with the proviso that when the linking group B, D or both is substituted the substituent is not =O or =S; X represents, either a $CH_2$ group or a hetero atom selected from the group of nitrogen, sulfur and oxygen; Ar represents an optionally substituted divalent single or fused aromatic or heterocyclic group; k is an integer ranging from 1–4 and and p is an integer ranging from 0 to 4, which comprises:

a) i) reacting the compound of formula (III)

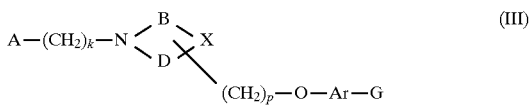
(III)

where G is a CHO group with 2,4-thiazolidinedione or 2,4-oxazolidinedione to yield a compound of formula (XII)

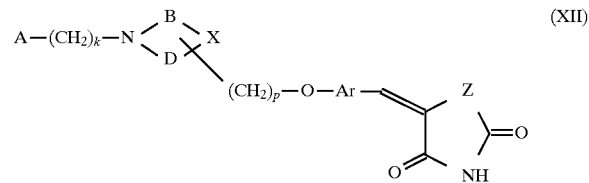
(XII)

where A, B, D, X, Ar, k, p and Z are as defined above and removing the water formed during the reaction;

ii) reducing the compound of formula (XII) obtained in step (i) above to obtain a compound of formula (XIII)

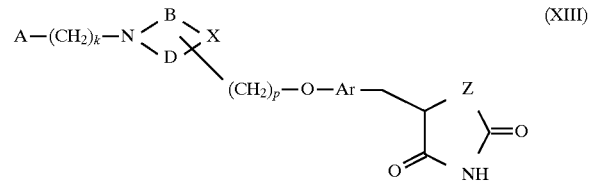
(XIII)

where A, B, D, X, Ar, k, p and Z are as defined above;

b) a process for the preparation of compound of formula (I) which comprises reacting a compound of formula (IV)

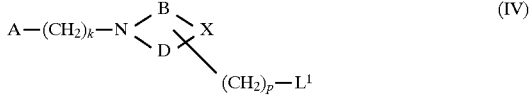
(IV)

where A, B, D, X, k and p are as defined above and $L^1$ is halogen atom or a leaving group, with a compound of formula (XIV)

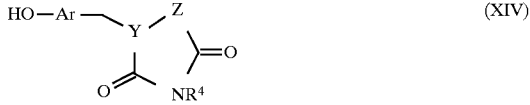
(XIV)

where Y, Z and Ar are as defined above and R4 is hydrogen or a nitrogen protecting group which is removed after the reaction;

c) a process for the preparation of compound of formula (I) which comprises reacting a compound of formula (VI)

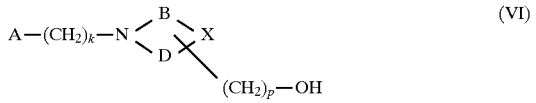

where A, B, D, X, k and p are as defined above with a compound of formula (XIV)

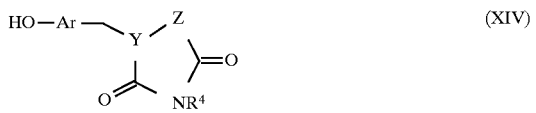

where Y, Z and Ar are as defined above and $R^4$ is hydrogen or a nitrogen protecting group, which is removed after the reaction; or d) a process for the preparation of compound of formula (I), which comprises reacting compound of formula (XV)

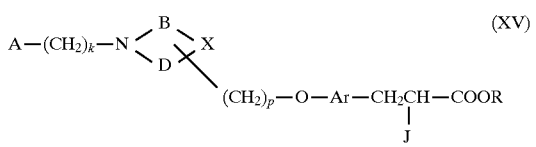

where A, B, D, X, k, p and Ar are as defined above, J is a halogen atom or a hydroxy group and R is a lower alkyl group, with thiourea when J is a halogen atom, or urea when J is a hydroxy group followed by treatment with an acid.

12. A pharmaceutical composition which comprises a compound of formula (I)

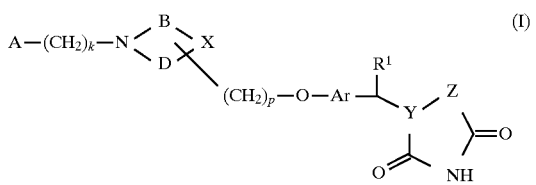

as defined in claim 1 and pharmaceutically acceptable carrier, diluent, excipient or solvate.

13. A pharmaceutical composition as claimed in claim 12, in the form of a tablet, capsule, powder, syrup, solution or suspension.

14. A pharmaceutical composition which comprises, a compound according to claim 9, as an effective ingredient and a pharmaceutically acceptable carrier, diluent or excipient.

15. A method of preventing or treating diseases in which insulin resistance is the underlying pathophysiological mechanism comprising administering a compound of formula (I) as defined in claim 1, and a pharmaceutically acceptable carrier, diluent or excipient to a patient in need thereof.

16. A method according to claim 15, wherein the disease is type II diabetes, impaired glucose tolerance, dyslipidaemia, hypertension, coronary heart disease, cardiovascular disorders, atherosclerosis, insulin resistance associated with obesity and psoriasis, diabetic complications, polycystic ovarian syndrome (PCOS), renal diseases, diabetic nephropathy, glomerulonephritis, glomerular sclerosis, nephrotic syndrome, hypertensive nephrosclerosis, endstage renal diseases, microalbuminuria, or eating disorders.

17. A method of reducing blood glucose, triglyceride or free fatty acids comprising administering to a mammal in need of reduction of blood glucose, triglyceride or free fatty acids one effective amount of a compound of formula (I) as defined in claim 1 and a pharmaceutically acceptable carrier diluent or solvate.

18. A compound according to claim 1, which is selected from the group consisting of the following compounds:

5-[4-[N-(6-benzyloxy-2,5,7,8-tetramethylchroman-2-ylmethyl)-(2S)-pyrrolidine-2-methoxyl]phenyl methylene] thiazolidine-2,4-dione and its salts;

5-[4-[N-(6-benzyloxy-2,5,7,8-tetramethylchroman-2-ylmethyl)-(2R)-pyrrolidine-2-methoxyl]phenyl methylene] thiazolidine-2,4-dione, and its salts;

5-[4-[N-(6-benzyloxy-2,5,7,8-tetramethylchroman-2-ylmethyl)-(2S)-pyrrolidine-2-methoxy]phenyl methyl] thiazolidine-2,4-dione;

5-[4-[N-(6-benzyloxy-2,5,7,8-tetramethylchroman-2-ylmethyl)-(2R)-pyrrolidine-2-methoxy]phenyl methyl] thiazolidine-2,4-dione and its salts;

5-[4-[N-(6-benzyloxy-2,5,7,8-tetramethylchroman-2-ylmethyl)-(2S)-pyrrolidine-2-methoxy]phenyl methyl] thiazolidine-2,4-dione sodium salt;

5-[4-[N-(6-benzyloxy-2,5,7,8-tetramethylchroman-2-ylmethyl)-(2S)-pyrrolidine-2-methoxy]phenyl methyl] thiazolidine-2,4-dione maleic acid salt;

5-[4-[N-(6-benzyloxy-2,5,7,8-tetramethylchroman-2-ylmethyl)-(2S)-pyrrolidine-2-methoxy]phenyl methyl] thiazolidine-2,4-dione hydrochloride salt;

5-[4-[N-(6-hydroxy-2,5,7,8-tetramethylchroman-2-ylmethyl)-(2S)-pyrrolidine-2-methoxy]phenyl methyl] thiazolidine-2,4-dione;

5-[4-[N-(6-hydroxy-2,5,7,8-tetramethylchroman-2-ylmethyl)-(2R)-pyrrolidine-2-methoxy]phenyl methyl] thiazolidine-2,4-dione, and its salts;

5-[4-[N-(6-hydroxy-2,5,7,8-tetramethylchroman-2-ylmethyl)-(2S)-pyrrolidine-2-methoxy]phenyl methyl] thiazolidine-2,4-dione sodium salt;

5-[4-[N-(6-hydroxy-2,5,7,8-tetramethylchroman-2-ylmethyl)-(2S)-pyrrolidine-2-methoxy]phenyl methyl] thiazolidine-2,4-dione maleic acid salt;

5-[4-[N-(6-hydroxy-2,5,7,8-tetramethylchroman-2-ylmethyl)-(2S)-pyrrolidine-2-methoxy]phenyl methyl] thiazolidine-2,4-dione hydrochloride salt;

5-[4-[N-(6-hydroxy-2,5,7,8-tetramethylchroman-2-ylmethyl)-(2S)-pyrrolidine-2-methoxy]phenyl methylene]thiazolidine-2,4-dione;

5-[4-[N-(6-hydroxy-2,5,7,8-tetramethylchroman-2-ylmethyl)-(2R)-pyrrolidine-2-methoxy]phenyl methylene]thiazolidine-2,4-dione and its salts;

5-[4-[N-(2,3-dihydro-5-benzyloxy-2,2,4,6,7-pentamethylbenzofuran-3-ylmethyl)-(2S)-pyrrolidine-2-methoxy]phenyl methylene]thiazolidine-2,4-dione;

5-[4-[N-(2,3-dihydro-5-benzyloxy-2,2,4,6,7-pentamethylbenzofuran-3-ylmethyl)-(2R)-pyrrolidine-2-methoxy]phenyl methylene]thiazolidine-2,4-dione and its salts;

5-[4-[N-(2,3-dihydro-5-benzyloxy-2,2,4,6,7-pentamethylbenzofuran-3-ylmethyl)-(2S)-pyrrolidine-2-methoxy]phenyl methylene]thiazolidine-2,4-dione maleic acid salt;

5-[4-[N-(2,3-dihydro-5-benzyloxy-2,2,4,6,7-pentamethylbenzofuran-3-ylmethyl)-(2S)-pyrrolidine-2-methoxy]phenyl methylene]thiazolidine-2,4-dione hydrochloride salt;

5-[4-[N-(2,3-dihydro-5-benzyloxy-2,2,4,6,7-pentamethylbenzofuran-3-ylmethyl)-(2S)-pyrrolidine-2-methoxy] phenyl methyl]thiazolidine-2,4-dione;

5-[4-[N-(2,3-dihydro-5-benzyloxy-2,2,4,6,7-pentamethylbenzofuran-3-ylmethyl)-(2R)-pyrrolidine-2-methoxy] phenyl methyl]thiazolidine-2,4-dione and its salts;

5-[4-[N-(2,3-dihydro-5-benzyloxy-2,2,4,6,7-pentamethylbenzofuran-3-ylmethyl)-(2S)-pyrrolidine-2-methoxy]phenyl methyl]thiazolidine-2,4-dione maleic acid salt;

5-[4-[N-(2,3-dihydro-5-benzyloxy-2,2,4,6,7-pentamethylbenzofuran-3-ylmethyl)-(2S)-pyrrolidine-2-methoxy]phenyl methyl]thiazolidine-2,4-dione hydrochloride salt;

5-[4-[N-(2,3-dihydro-5-hydroxy-2,2,4,6,7-pentamethylbenzofuran-3-ylmethyl)-(2S)-pyrrolidine-2-methoxy]phenyl methyl]thiazolidine-2,4-dione;

5-[4-[N-(2,3-dihydro-5-hydroxy-2,2,4,6,7-pentamethylbenzofuran-3-ylmethyl)-(2R)-pyrrolidine-2-methoxy]phenyl methyl]thiazolidine-2,4-dione and its salts;

5-[4-[N-(2,3-dihydro-5-hydroxy-2,2,4,6,7-pentamethylbenzofuran-3-ylmethyl)-(2S)-pyrrolidine-2-methoxy]phenyl methyl]thiazolidine-2,4-dione hydrochloride salt;

5-[4-[N-(2,3-dihydro-5-hydroxy-2,2,4,6,7-pentamethylbenzofuran-3-ylmethyl)-(2S)-pyrrolidine-2-methoxy]phenyl methylene]thiazolidine-2,4-dione;

5-[4-[N-(2,3-dihydro-5-hydroxy-2,2,4,6,7-pentamethylbenzofuran-3-ylmethyl)-(2R)-pyrrolidine-2-methoxy]phenyl methylene]thiazolidine-2,4-dione and its salts;

5-[4-[N-(5-benzyloxy-2-methylbenzofuran-3-ylmethyl)-(2S)-pyrrolidine-2-methoxy]phenyl methylene]thiazolidine-2,4-dione;

5-[4-[N-(5-benzyloxy-2-methylbenzofuran-3-ylmethyl)-(2S)-pyrrolidine-2-methoxy]phenyl methylene]thiazolidine-2,4-dione sodium salt, and 5-[4-[N-(5-benzyloxy-2-methylbenzofuran-3-ylmethyl)-(2S)-pyrrolidine-2-methoxy]phenyl methyl]thiazolidine-2,4-dione;

a polymorphic form 1 of 5-[4-[N-[(2RS)-6-Benzyloxy-2,5,7,8-tetramethylchroman-2-ylmethyl]-(2S)-pyrrolidine-2-methoxy]phenyl methylene]thiazolidine-2,4-dione characterized by mp of about 186.6° C., and $^1$H NMR (CDCl$_3$, 200 MHz): δ 1.21, 1.26 (2s, 3H), 1.5–2.05 (m, 6H), 2.08–2.22 (6s, 9H), 2.35–3.15 (m, 6H), 3.4 (m, 1H), 3.8 (m, 1H), 4.0 (m, 1H), 4.7 (s, 2H), 6.95 (m, 2H), 7.3–7.6 (m, 7H), 7.8 (s, 1H);

a polymorphic form 2 of 5-[4-[N-[(2RS)-6-Benzyloxy-2,5,7,8-tetramethylchroman-2-ylmethyl]-(2S)-pyrrolidine-2-methoxy]phenyl methylene]thiazolidine-2,4-dione characterized by mp of about 88° C., and $^1$H NMR (CDCl$_3$, 200 MHz): δ 1.21, 1.26 (2s, 3H), 1.5–2.05 (m, 6H), 2.08–2.22 (6s, 9H), 2.35–3.15 (m, 6H), 3.4 (m, 1H), 3.8 (m, 1H), 4.0 (m, 1H), 4.7 (s, 2H), 6.95 (m, 2H), 7.3–7.6 (m, 7H), 7.8 (s, 1H); and a polymorphic form 3 of 5-[4-[N-[(2RS)-6-Benzyloxy-2,5,7,8-tetramethylchroman-2-ylmethyl]-(2S)-pyrrolidine-2-methoxy]phenyl methylene]thiazolidine-2,4-dione characterized by mp of about 86° C.; and $[\alpha]_D^{24}$=−17.3 (c, 1.0, CDCl$_3$) and $^1$H NMR (CDCl$_3$, 200 MHz): δ 1.21, 1.26 (2s, 3H), 1.5–2.05 (m, 6H), 2.08–2.22 (6s, 9H), 2.35–3.15 (m, 6H), 3.4 (m, 1H), 3.8 (m, 1H), 4.0 (m, 1H), 4.7 (s, 2H), 6.95 (m, 2H), 7.3–7.6 (m, 7H), 7.8 (s, 1H).

19. A pharmaceutical composition which comprises a compound of claim 18 and a pharmaceutically acceptable carrier, diluents, excipient or solvate.

* * * * *

UNITED STATES PATENT AND TRADEMARK OFFICE
CERTIFICATE OF CORRECTION

PATENT NO. : 5,889,032
DATED : March 30, 1999
INVENTOR(S) : Lohray et al.

It is certified that error appears in the above-identified patent and that said Letters Patent is hereby corrected as shown below:

On title page, item 30, "821" should be -- 721--.

Signed and Sealed this

Eleventh Day of January, 2000

Attest:

Q. TODD DICKINSON

*Attesting Officer*   *Acting Commissioner of Patents and Trademarks*

UNITED STATES PATENT AND TRADEMARK OFFICE
CERTIFICATE OF CORRECTION

PATENT NO. : 5,889,032

DATED : March 30, 1999

INVENTOR(S) : Vidya Bhushan LOHRAY, et al.

Page 1 of 2

It is certified that error appears in the above-identified patent and that said Letters Patent is hereby corrected as shown below:

| | |
|---|---|
| Column 10, line 48, | "]" should read -- ) --. |
| Column 10, line 49, | ")" should read -- ] --. |
| Column 10, line 51, | "]" should read -- ) --. |
| Column 10, line 52, | ")" should read --] --. |
| Column 11, line 28, | "methoxyphenyl" should read -- methoxy ] phenyl --. |
| Column 12, line 5, | after "thereof" insert a period -- . --. |
| Column 17, line 27, | "$R^6$" should read -- $R^b$ --. |
| Column 21, line 17, | methanesulphgnate" should read -- methanesulphonate --. |
| Column 25, line 65, | "31" should read -- 3H --. |
| Column 26, line 26, | after "Hz" insert -- , 2H --. |
| Column 28, line 43, | "Benzyloy" should read -- Benzyloxy --. |
| Column 29, line 16, | "6.6" should -- 8.6 --. |

UNITED STATES PATENT AND TRADEMARK OFFICE
CERTIFICATE OF CORRECTION

PATENT NO. : 5,889,032
DATED : March 30, 1999
INVENTOR(S) : Vidya Bhushan Lohray, et al It is certified that error appears in the above-identified patent and that said Letters Patent is hereby corrected as shown below:

| | |
|---|---|
| Column 29, line 24, | "Hhhz" should read -- Hz --. |
| Column 29, line 46, | "ymethyll" should read -- ymethyl] --. |
| Column 32, line 48, | "Benzyloy" should read -- Benzyloxy --. |
| Column 33, line 4, | "8Hz" should read -- 9 Hz --. |
| Column 33, line 11, | "methyloxylnitrobenzene" should read -- methloxy]nitrobenzene --. |
| Column 34, line 3, | "Benzyloy" should read -- Benzyloxy --. |
| Column 34, line 44, | "41" should read -- 4H --. |
| Column 35, line 23, | "ymethyll" should read --ymethyl] --. |
| Column 41, line 65, | "Benzyloy" should read -- Benzyloxy --. |
| Column 54, line 60, | "-" should read -- = - --. |
| Column 65, line 6, | after "4," delete "0". |

Signed and Sealed this

Fifth Day of September, 2000

Attest:

Q. TODD DICKINSON

*Attesting Officer*  *Director of Patents and Trademarks*